United States Patent
Borody

(10) Patent No.: US 11,857,617 B2
(45) Date of Patent: Jan. 2, 2024

(54) METHODS FOR TREATING, AMELIORATING OR PREVENTING INFECTIONS USING DRUG AND VACCINATION COMBINATION TREATMENT

(71) Applicant: TOPELIA AUST LIMITED (652 771 670), Five Dock (AU)

(72) Inventor: Thomas Julius Borody, Five Dock (AU)

(73) Assignee: TOPELIA AUST LIMITED (652 771 670), Five Dock (AU)

(\*) Notice: Subject to any disclaimer, the term of this patent is extended or adjusted under 35 U.S.C. 154(b) by 0 days.

(21) Appl. No.: 17/525,775

(22) Filed: Nov. 12, 2021

(65) Prior Publication Data
US 2022/0370589 A1 Nov. 24, 2022

Related U.S. Application Data

(60) Provisional application No. 63/273,069, filed on Oct. 28, 2021, provisional application No. 63/253,813, filed on Oct. 8, 2021, provisional application No. 63/241,485, filed on Sep. 7, 2021, provisional application No. 63/223,427, filed on Jul. 19, 2021, provisional application No. 63/214,997, filed on Jun. 25, 2021, provisional application No. 63/188,311, filed on May 13, 2021, provisional application No. 63/186,660, filed on May 10, 2021.

(51) Int. Cl.
| | |
|---|---|
| *A61K 39/12* | (2006.01) |
| *A61K 45/06* | (2006.01) |
| *A61K 31/166* | (2006.01) |
| *A61P 31/14* | (2006.01) |
| *C12N 7/00* | (2006.01) |
| *A61K 39/00* | (2006.01) |

(52) U.S. Cl.
CPC ............ *A61K 39/12* (2013.01); *A61K 31/166* (2013.01); *A61K 45/06* (2013.01); *A61P 31/14* (2018.01); *C12N 7/00* (2013.01); *A61K 2039/545* (2013.01)

(58) Field of Classification Search
None
See application file for complete search history.

(56) References Cited

U.S. PATENT DOCUMENTS

| 11,124,497 B1 | 9/2021 | Arnold et al. |
| 2021/0355111 A1 | 11/2021 | Arnold et al. |
| 2021/0361688 A1 | 11/2021 | Riveros |

FOREIGN PATENT DOCUMENTS

| WO | 2021221043 A1 | 4/2021 |
| WO | 2021207632 A1 | 10/2021 |
| WO | 2021212183 A1 | 10/2021 |
| WO | 2021231872 A1 | 11/2021 |
| WO | WO-2021231872 A1 * | 11/2021 |
| WO | 2021250648 A1 | 12/2021 |

OTHER PUBLICATIONS

Tanne BMJ 2020;371:m4799 (Year: 2020).*
Carter—https://www.aidsmap.com/news/oct-2009/50mg-ritonavir-may-be-effective-booster-some-protease-inhibitors (Year: 2009).*
Fiona Mitchell www.thelancet.com/diabetes-endocrinology vol. 8 (Year: 2020).*
Pal et al. Biological Trace Element Research (2021) 199:2882-2892 (Year: 2021).*
Ramasamy et al., The Lancet vol. 396, Issue 10267, pp. 1979-1993 (Year: 2020).*
Kyriakidis, N.C., López-Cortés, A., González, E.V. et al. SARS-CoV-2 vaccines strategies: a comprehensive review of phase 3 candidates. npj Vaccines 6, 28 (2021). (Year: 2021).*
Daniel Echeverría-Esnal, et al., Azithromycin in the treatment of COVID-19: a review, Expert Review of Anti-infective Therapy, 19:2, 147-1636 (Year: 2021).*
Mullard Nature Revs Drug Disc, vol. 16, p. 305 (Year: 2017).*
Xu J, et al., Lessons learnt from hydroxychloroquine/azithromycin in treatment of COVID-19. Eur Respir J 2022; 59: 2102002 (Year: 2022).*
Kumar et al., Antimicrob Agents Chemother. Jan. 18, 2022;66(1):e0154321. doi: 10.1128/AAC.01543-21. Epub Oct. 11, 2021 (Year: 2022).*

(Continued)

*Primary Examiner* — Shanon A. Foley
*Assistant Examiner* — Myron G Hill
(74) *Attorney, Agent, or Firm* — Greer, Burns & Crain, LTD.; Gregory P. Einhorn

(57) ABSTRACT

In alternative embodiments, provided are methods for treating, ameliorating, decreasing the chances of having any adverse effects from, decreasing the severity of adverse effects from, or preventing an infection by administration of an antibiotic and/or an anti-viral drugs and a vaccine directed to a causative agent of the infection and/or an attenuated and/or a live, viable or infectious causative agent of the infection. In alternative embodiments, the infection is bacterial or viral. In alternative embodiments, the viral infection is a coronavirus infection such a Covid-19 infection. In alternative embodiments, methods as provide herein prevent or decrease the prevalence or severity of "vaccine breakthrough infections" after vaccination, where external mutants of COVID-19 infect patients in spite of the fact that they have undergone immunization, for example, to prevent a mutant or variant COVID-19 infection. In alternative embodiments, an antiviral combination administered in coordination with a vaccine comprises PF-07321332 or PAXLOVID™ and/or ritonavir, or ivermectin, doxycycline and a zinc or a zinc salt. In alternative embodiments, methods as provided herein are used to prevent in vivo mutations of such mutant infectious agent to enhance the efficacy of an administered vaccination; in other words, methods as provided herein are used to prevent in vivo replication of an acquired viral mutant or variant infectious agent, and thus also prevents ongoing mutations of the viral infectious agent because using the combination antiviral co-therapy where there is no replication of infectious agent and so there is no possible further mutation of the infectious agent.

17 Claims, No Drawings

(56) References Cited

OTHER PUBLICATIONS

Pandey, et al.,Ivermectin in COVID-19: What do we know?, Diabetes & Metabolic Syndrome: Clinical Research & Reviews, vol. 14, Issue 6, 2020, pp. 1921-1922 (Year: 2020).*

Hazan et al., "Effectiveness of ivermectin-based multidrug therapy in severely hypoxic, ambulatory COVID-19 patients" Future Microbiol., Feb. 9, 2022, Epub.

Borody et al (Oct. 19, 2021) Trial Site News article entitled Combination Therapy For COVID-19 Based on Ivermectin in an Australian Population.

Stone et al (Nov. 9, 2021) Research Square article, entitled "Rapid increase of SpO2 on room air for 34 severe COVID-19 patients after ivermectin-based combination treatment: 55-62% normalization within 12-24 hours".

Hazan et al article (Feb. 9, 2022) entitled "Effectiveness of ivermectin-based multidrug therapy in severely hypoxic, ambulatory COVID-19 patients", Future Microbiol./ Future Medicine.

* cited by examiner

METHODS FOR TREATING, AMELIORATING OR PREVENTING INFECTIONS USING DRUG AND VACCINATION COMBINATION TREATMENT

RELATED APPLICATIONS

This U.S. Utility Patent application claims the benefit of priority under 35 U.S.C. § 119(e) of U.S. Provisional Application Serial No. (USSN) 63/186,660, filed May 10, 2021; U.S. Ser. No. 63/188,311, May 13, 2021; U.S. Ser. No. 63/214,997, Jun. 25, 2021; USSN 63/223,427, Jul. 19, 2021; U.S. Ser. No. 63/241,485 filed Sep. 7, 2021; U.S. Ser. No. 63/253,813 filed Oct. 8, 2021; and, U.S. Ser. No. 63/273,069, filed Oct. 28, 2021. The aforementioned applications are expressly incorporated herein by reference in its entirety and for all purposes.

TECHNICAL FIELD

This invention generally relates to medicine and the medical treatment of infections with vaccines, antibiotics and anti-viral drugs. In alternative embodiments, provided are methods for treating, ameliorating, decreasing the chances of having any adverse effects from, decreasing the severity of adverse effects from, or preventing an infection by administration of an antibiotic and/or an anti-viral drugs and a vaccine directed to a causative agent of the infection and/or an inactivated or attenuated causative agent of the infection, or a live, viable or infectious causative agent of the infection. In alternative embodiments, the infection is bacterial, parasitic or viral. In alternative embodiments, the viral infection is a coronavirus infection such a Covid-19 or Covid-19 variant infection. In alternative embodiments, methods as provided herein prevent or decrease the prevalence or severity of "vaccine breakthrough infections" after vaccination, where mutants of the infection's causative agent develop and infect patients in spite of the fact that they have undergone immunization, for example, to prevent a Covid-19 infection. In alternative embodiments, methods as provided herein are used to prevent in vivo mutations of an infectious agent to enhance to efficacy of an administered vaccination; in other word, methods as provided herein are used to prevent in vivo replication of a viral infectious agent, and thus also prevents mutations of the viral infectious agent because where there is no replication of infectious agent there is no mutation of infectious agent. In alternative embodiments, methods comprising administration of a combination of an antiviral medication, drug or treatment such as PF-07321332 or PAXLOVID™ and/or ritonavir and a vaccine prevents acquisition of externally mutated viruses infecting the vaccinated person, as well as preventing replication in those possessing less effective neutralising antibodies to the mutants.

BACKGROUND

The process of immunization attempts to create immunity to prevent acquisition of the new coronavirus or viruses. However, there is ongoing mutation occurring in the surrounding population because of ongoing replication of viruses. Hence, "vaccine breakthrough" infections are becoming reported, for example, see Hacisuleyman et al., New Eng J Med, Apr. 21, 2021. If the vaccine creates immunity to only the strains it was created for, it may permit 'reinfection' with Covid-19 of a mutant strain inhaled by the immunized person. This is termed "Vaccine breakthrough'. Within the immunized person replication of an external infectious mutant can take place because the vaccine alone is inadequate to control the mutant replicating and the mutant strain may further mutate in this seemingly safely immunized subject.

With COVID-19, there has been a rush into development of vaccines that could prevent the disease. However, the nature of this infection, being an intracellular RNA type of virus, does not result in an easy development of a vaccine. There are vaccines which work, for example, small pox, tetanus, polio, or measles, and there are conditions where vaccines are of little use, for example, hepatitis C, human immunodeficiency virus (HIV) infection and tuberculosis (TB), and then there are vaccines which only give partial immunization and for a short period of time, such as for example influenza virus immunization and more recently malaria immunization attempts.

Currently used mRNA vaccines as well as non-mRNA vaccines are manufactured by different companies such as Pfizer, AstraZeneca, Moderna, Johnson and Johnson (Janssen), Sputnik V, NovaVax, Sinovac, Sinopharm, Biological E, Valneva, EpiVac Corona, Convidiciae, Covaxin and others. All have been subject to various local side effects such as a swollen arm, systemic side effects such as fever, aches and pains, overwhelming feeling of doom, discomfort, profound tiredness and other symptoms. A small percentage of patients develop thrombocytopenia and clotting which is reminiscent of disseminated intravascular coagulation as described by some, as well as neurologic, dermatologic, cardiac and other adverse effects.

The preventative success of mRNA vaccines has been reported to be up to 90% or more. However, in real life experience data in some countries has shown results of 50% to 90% efficacy. Some of these reduced efficacy levels may be due to mutants being present in that population. Unless vaccine manufacturers can predict the development of specific mutations, which is virtually impossible, the vaccine market will always suffer from such reduced efficacy in various regions of the world.

Because of the ongoing mutations around the world of COVID-19, there are multiple strains, including a current India strain, which has caused super-infections in patients who have been immunized, i.e., the so-called vaccine breakthrough phenomenon. The B.1.617 variant of the Covid-19, known more commonly as the double mutant strain, was first detected in India in October 2020. As the name suggests, the strain involves two variants of the virus. The E484Q mutation has characteristics of a previously detected variant—the E484K—which was seen in the fast-spreading Brazilian and South African variants, making it highly transmissible. The L452R mutation, on the other hand, helps the virus evade the body's immune response. The double mutation strain was subsequently named B.1.617

Yet it is clear that the virus had to replicate to mutate. Hence the adage "if it cannot replicate it cannot mutate". Hence, one simple solution to the problem of imperfect vaccine disease prevention is not a bigger and better vaccine or multiple vaccinations because we will never keep up with the mutations. The best solution may well be prevention of mutations. Yet it is clear that the virus had to replicate to mutate. And subsequently replicate in the immunized person. Hence the adage "if it cannot replicate it cannot mutate".

SUMMARY

In alternative embodiments, provided are methods for treating, ameliorating, decreasing the chances of having any adverse effects from, decreasing the severity of adverse effects from, or preventing an infection, comprising administering to a subject or an individual in need thereof, wherein optionally the individual in need thereof is a human or an animal:

(a) at least one antibiotic and/or anti-viral drug capable of killing a causative agent of the infection, or completely or partially inhibiting the ability of the causative agent of the infection to replicate or become infectious or cause pathology in the subject or the individual in need thereof; and, (b) (i) at least one dose of a vaccine directed to the causative agent of the infection upon entry into the vaccinated subject or individual in need thereof, wherein the vaccine is capable of initiating an immune response in the individual that can substantially or partially kill or neutralize a causative agent of the infection, or the vaccine can completely, substantially or partially inhibit the ability of the causative agent of the infection to replicate, or be infectious, or cause pathology, in the subject or the individual in need thereof, and/or (ii) an inactivated or attenuated agent of the infection, or a live, viable or infectious causative agent of the infection, wherein optionally the live causative agent of the infection is a completely or partially attenuated version of the causative agent, wherein at least one dosage of the at least one antibiotic and/or anti-viral drug is administered 1, 2, 3, 4, 5, 6, 7, 8, 9, 10, 11, 12, 13 or 14 or more days before, or on the day of, a first dose of the at least one of a plurality of dosages of the vaccine is administered, or a dose of the inactivated, attenuated, or the live, viable or infectious causative agent of the infection.

In alternative embodiments, the causative agent of the infection is or comprises a bacteria, protozoan or a virus, or the causative agent of the infection is or comprises the causative agent of:

a viral infection, optionally a coronavirus, a virus that causes a common cold, an influenza virus (optionally an influenza A, B or C), a hepatitis virus, a respiratory syncytial virus (RSV), a Paramyxoviridae or measles virus, a Paramyxovirus or mumps virus, a Herpes simplex virus (HSV), a Cytomegalovirus (CMV), a Rubivirus or rubella virus, an Enterovirus, a viral meningitis, a rhinovirus, a human immunodeficiency virus (HIV), a varicella-zoster or chickenpox virus, an Orthopoxvirus or variola or smallpox virus, an Epstein-Barr virus (EBV), an Adenovirus, a Hantavirus, a Flaviviridae or Dengue virus, a Zika virus, or a chikungunya virus infection, a coronavirus infection, optionally a COVID-19 or a COVID-19 variant infection, or a Middle East respiratory syndrome virus (MERS-CoV) infection;

malaria caused by a parasite of the genus *Plasmodium* (optionally *P. vivax, P. falciparum, P. malariae, P. ovale*, or *P. knowlesi*);

dengue fever or dengue shock syndrome caused by a virus of the Flaviviridae family or a dengue virus;

a Flaviviridae family virus infection or a hepatitis or a hepatocellular carcinoma associated with viral hepatitis caused by a virus of the Flaviviridae family or a virus of the genus Hepacivirus or Hepacivirus C virus or hepatitis C;

filariasis, leprosy or streptocerciasis or an infection caused by a parasite of the superfamily Filarioidea (optionally *Brugia malayi, Brugia timori, Wuchereria bancrofti, Loa loa Mansonella streptocerca, Mansonella ozzardi*, or *Mansonella perstans*);

leprosy or an infection caused by a parasite of the genus *Mycobacterium* (optionally *M. leprae* or M lepromatosis);

river blindness or onchocerciasis caused by a parasitic worm or a parasite of the genus *Onchocerca* (optionally *O. volvulus*);

a hookworm or a roundworm infection caused by a parasite of the genus *Ancylostoma* (optionally *A. duodenale* or *A. ceylanicum*) or Necator (optionally *N. americanus*);

trichuriasis or a whipworm infection caused by a parasite of the genus *Trichuris* (optionally *T. trichiura*); roundworm or an *Ascaris* infection that is caused by *Ascaris lumbricoides;* scabies or a mite-carried infection caused by the parasite of the genus *Sarcoptes* (optionally *S. scabiei*);

typhus or an infection caused by a lice or a parasite of the order Phthiraptera (optionally *Pediculus humanus* capitis);

enterobiasis or an infection caused by a pinworm or a parasite of the genus *Enterobius* (optionally *E. vermicularis*); and/or pulicosis or an infection caused by a flea or an insect of the order Siphonaptera or of the genus *Pulex* (optionally *P. irritans*).

In alternative embodiments, the virus is an influenza virus or a coronavirus, optionally a COVID-19 virus.

In alternative embodiments, the at least one antibiotic and/or anti-viral drug comprises: an avermectin class drug (optionally ivermectin) alone; a combination of an avermectin class drug and an antibiotic, or a combination of an ivermectin and an antibiotic or an antiviral drug or therapeutic, optionally a combination of an avermectin class drug, an antibiotic and zinc or a zinc salt, or a combination of ivermectin and an antibiotic and zinc or a zinc salt.

In alternative embodiments, the avermectin class drug comprises: ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin. In alternative embodiments, the avermectin class drug is administered with a synthetic nucleoside analog or derivative, or N4-hydroxycytidine, or a prodrug of N4-hydroxycytidine, optionally molnuvpiravir (Merck), or favipiravir (also known as T-705 or AVIGAN™, or favilavir, Toyama Chemical, Fujifilm, Japan, or FABIFLU™, Glenmark Pharmaceuticals).

In alternative embodiments, the antibiotic comprises an antibacterial antibiotic or a macrolide drug, wherein optionally the macrolide drug comprises azithromycin, optionally dosaged at between about 50 mg to about 2000 mg per dose or per day (optionally, ZITHROMAX™, or AZITHROCIN™, optionally an oral extended- or delayed-release formulation of azithromycin, or ZMAX™), clarithromycin (optionally, BIAXIN™), erythromycin (optionally, ERYTHROCIN™), or fidaxomicin (optionally, DIFICID™ or DIFICLIR™), troleandomycin (optionally, TEKMISIN™), tylosin (optionally, TYLOCINE™ or TYLAN™), solithromycin (optionally, SOLITHERA™), oleandomycin (or SIGMAMYCINE™), midecamycin, roxithromycin, kitasamycin or turimycin, josamycin, carbomycin or magnamycin, and/or spiramycin, and optionally the antibacterial antibiotic comprises a tetracycline class drug, a glycylcycline or a fluorocycline class drug, or an analogue thereof, and optionally the tetracycline, glycylcycline or fluorocycline drug or analogue thereof comprises or is: tetracycline or SUMYCIN™; chlortetracycline or AUREOMYCIN™; oxytetracycline; demeclocycline or DECLOMYCIN™, DECLOSTATIN™, LEDERMYCIN™, BIOTERCICLIN™, DEGANOL™, DETECLO™, DETRAVIS™, MECICLIN™, MEXOCINE™, CLORTETRIN™; lymecycline; meclocycline; metacycline; minocycline or MINOCIN™; rolitetracycline; doxycycline, or DORYX™, DOXYHEXA™, DOXYLIN™; tigecycline or TYGACIL™; eravacycline or XERAVA™; sarecycline or SEYSARA™ omadacycline or NUZYRA™; or any combination thereof.

In alternative embodiments, the at least one antibiotic and/or anti-viral drug comprises a combination of ivermectin and doxycycline (optionally DORYX™, DOXYHEXA™, DOXYLIN™), optionally a combination of ivermectin, doxycycline and zinc or a zinc salt.

In alternative embodiments, the at least one antibiotic and/or anti-viral drug comprises a combination of ivermectin and azithromycin (optionally, ZITHROMAX™, or AZITHROCIN™, optionally an oral extended-release formulation of azithromycin, or ZMAX™), optionally a combination of ivermectin, azithromycin and zinc or a zinc salt.

In alternative embodiments, the at least one antibiotic and/or anti-viral drug comprises a combination of hydroxychloroquine (optionally, PLAQUENIL™) and azithromycin (optionally, ZITHROMAX™, or AZITHROCIN™, optionally an oral extended-release formulation of azithromycin, or ZMAX™), optionally a combination of hydroxychloroquine, azithromycin and zinc or a zinc salt.

In alternative embodiments, the at least one antibiotic and/or anti-viral drug further comprises administration of a vitamin, optionally vitamin D and/or vitamin C.

In alternative embodiments, the zinc comprises: zinc sulphate, zinc acetate, zinc gluconate or zinc picolinate or a zinc salt.

In alternative embodiments, on the day of administration of, or at least one day after the first dose of: (a) the attenuated and/or the live, viable or infectious causative agent of the infection, and/or (b) the vaccine, is given, the individual in need thereof is administered more of the at least one antibiotic and/or anti-viral drug, or a different combination of an least one antibiotic and/or anti-viral drug, or a different dosage of the at least one antibiotic and/or anti-viral drug.

In alternative embodiments, the individual in need thereof is administered more of the at least one antibiotic and/or anti-viral drug, or a different combination of an least one antibiotic and/or anti-viral drug, or a different dosage of the at least one antibiotic and/or anti-viral drug on day zero (the day of administration), or day 1, 2, 3, 4, 5, 6, 7, 8, 9, 10, 11, 12, 13 or 14 after administration of the first dosage of the vaccine and/or the attenuated and/or the live, viable or infectious causative agent of the infection.

In alternative embodiments, a booster, or at least one second or follow-up administration of: at least one dosage of a vaccine and/or an attenuated and/or a live, viable or infectious causative agent of the infection, is given between about 1 week to one year (or between about two weeks to 9 months, or between about three weeks to 8 months, or between about one month to 7 months, or about 3, 4, 5, or 6 months) after the first administration of the at least one vaccine and/or the attenuated and/or the live, viable or infectious causative agent of the infection, and optionally, wherein on day zero, or at least one day, or about two days, after, administration of the second or additional or booster dose of the vaccine, and/or the attenuated and/or the live, viable or infectious causative agent of the infection, is given, the individual in need thereof is administered more of the at least one antibiotic and/or anti-viral drug, or a different combination of an least one antibiotic and/or anti-viral drug, or a different dosage of the at least one antibiotic and/or anti-viral drug.

In alternative embodiments, the individual in need thereof is administered more of the at least one antibiotic and/or anti-viral drug, or a different combination of an least one antibiotic and/or anti-viral drug, or a different dosage of the at least one antibiotic and/or anti-viral drug on day 1, 2, 3, 4, 5, 6, 7, 8, 9, 10, 11, 12, 13 or 14 after administration of the second or additional or booster dose of the vaccine and/or the attenuated and/or the live, viable or infectious causative agent of the infection.

In alternative embodiments, the at least one antibiotic and/or anti-viral drug is repeatedly administered about every 1, 2, 3, 4, 5, 6, 7, 8, 9, 10, 11, 12, 13 or 14 or more days for one or several weeks (optionally, 2, 3, 4, 5, or 6 weeks) until plasma ivermectin is detectable.

In alternative embodiments, the vaccine is: a nucleic acid-based vaccine, optionally an RNA vaccine or a DNA vaccine; a peptide or polypeptide-based vaccine; or, the vaccine comprises an inactivated virus.

In alternative embodiments, the anti-bacterial and/or anti-viral drug or drug combination, or the attenuated and/or the live, viable or infectious causative agent of the infection, or the vaccine, is administered orally or by inhalation, or the the anti-bacterial and/or anti-viral drug or drug combination or the attenuated and/or the live, viable or infectious causative agent of the infection is administered by inclusion in a liquid (optionally to be administered as a drink or in drops such as nasal drops or in a mist), a tablet, a capsule, a gel, a geltab, a powder, a lozenge, an aerosol, spray, or mist formulation that is inhaled or administered nasally or orally (optionally, by a puffer or a nebulizer), or is formulated in a liquid (optionally the liquid is a sterile saline) solution which is ingested or gargled by the individual in need thereof.

In alternative embodiments, the attenuated and/or the live, viable or infectious causative agent of the infection is administered in unit dosages of between about 10 to 50 trillion infectious units or particles, or between about one infectious unit or particle to 10, 20 or 30 billion infection units or particles.

In alternative embodiments, after the first administration of (a) the attenuated and/or the live, viable or infectious causative agent of the infection, and/or (b) the vaccine, the IgM, IgG and/or IgA levels in the individual in need thereof is tested and measured (qualitatively and/or quantitatively), and optionally if levels of the measured IgM, IgG and/or IgA are low, a second or additional dosage or administration of the (a) the attenuated and/or the live, viable or infectious causative agent of the infection, and/or (b) the vaccine, is given, and optionally levels of the measured IgM, IgG and/or IgA are measured at between about 7 to 21 days, or at 14 and 20 days, after the first administration.

In alternative embodiments, the individual in need thereof is a human or an animal, and optionally the animal is a domestic, farm or zoo animal.

In alternative embodiments, the methods comprise administering in coordination with (optionally before, at the time of and/or after vaccination of and/or administration of the attenuated and/or the live, viable or infectious causative agent of the infection) the anti-microbial (optionally antiviral) vaccine and/or the attenuated and/or the live, viable or infectious causative agent of the infection, a therapeutic combination of drugs or a single drug, an antisera or an antibody, a pharmaceutical dosage form, a drug delivery device, or a product of manufacture, comprising:

(a) a thiazolide class drug, optionally nitazoxanide (or ALINIA™, NIZONIDE™) or tizoxanide (or 2-Hydroxy-N-(5-nitro-2-thiazolyl)benzamide);

(b) molnupiravir, optionally co-administered with and/or formulated with an avermectin class drug (optionally ivermectin), an antibiotic (optionally doxycycline or azithromycin) and/or zinc, or co-administered with and/or formulated with ivermectin, hydroxychloroquine, an antibiotic (optionally doxycycline or azithromycin) and/or zinc;

(c) opaganib or YELIVA™, or opaganib or YELIVA™ and oral and/or inhaled or aerosol chloroquine (or ARALEN™), chloroquine phosphate, chloroquine diphosphate, amodiaquine (or AMDAQUINE™, AMOBIN™) and/or hydroxychloroquine (optionally, PLAQUENIL™), wherein optionally each or both of the opaganib and the chloroquine (or ARALEN™), chloroquine phosphate, chloroquine diphosphate and/or hydroxychloroquine (optionally, PLAQUENIL™) are in or formulated as a formulation for inhalation, for example, formulated as an aerosol, spray, mist, liquid or powder, or each or both are formulated for oral, intramuscular or intravenous administration, wherein optionally the opaganib is administered at a dosage of QD (once a day), bid (twice a day) or tid (three times a day) at a dosage of between about 100 to 600 mg per day or per dosage, or at about 100, 200, 300, 400, 500 or 600 mg per day or per dosage, and optionally the opaganib, or YELIVA™ is also administered or formulated with an antibiotic (optionally azithromycin or doxycycline), ivermectin (optionally at 12 mg ivermectin, optionally administered on days 1, 3, 6 and 8), hydroxychloroquine (optionally, PLAQUENIL™) and/or zinc (optionally zinc sulfate, optionally at (50 mg daily, or any zinc salt);

(d) lopinavir, ritonavir (or NORVIR™) and oseltamivir (optionally, TAMIFLU™), and/or zanamivir (or RELENZA™);

(e) lopinavir combined (formulated) with ritonavir (or NORVIR™), or KALETRA™, ALTERA™, ALUVIA™, KALMELTREX, LOPIMUNE™ or LOPINAVIR™, and/or zanamivir (or RELENZA™), or lopinavir and ritonavir separately formulated;

(f) lopinavir combined (formulated) with ritonavir (or NORVIR™) (or KALETRA™, ALTERA™, ALUVIA™, KALMELTREX, LOPIMUNE™ or LOPINAVIR™), or lopinavir and ritonavir (or NORVIR™), and oseltamivir (optionally, TAMIFLU™), and/or zanamivir (or RELENZA™), optionally also with inhaled or aerosol formulations or versions of chloroquine (or ARALEN™) amodiaquine (or AMDAQUINE™, AMOBIN™), chloroquine phosphate, and/or oral chloroquine (or ARALEN™), chloroquine phosphate, chloroquine diphosphate and/or hydroxychloroquine (optionally, PLAQUENIL™) simultaneously;

(g) lopinavir, ritonavir (or NORVIR™), amodiaquine (or AMDAQUINE™, AMOBIN™), chloroquine and oseltamivir (or TAMIFLU™); wherein optionally the chloroquine comprises inhaled or aerosol chloroquine (or ARALEN™), chloroquine phosphate, chloroquine diphosphate and/or hydroxychloroquine (optionally, PLAQUENIL™) and/or oral chloroquine (or ARALEN™), chloroquine phosphate, chloroquine diphosphate and/or hydroxychloroquine (optionally, PLAQUENIL™) simultaneously;

(h) lopinavir and oseltamivir (optionally, TAMIFLU™), and/or zanamivir (or RELENZA™);

(i) ritonavir (or NORVIR™) and oseltamivir (optionally, TAMIFLU™), and/or zanamivir (or RELENZA™);

(j) remdesivir (optionally, GS-5734™, Gilead Sciences) alone, or oseltamivir (optionally, TAMIFLU™) and remdesivir (optionally, GS-5734™, Gilead Sciences), and optionally the remdesivir is an oral formulation and/or an inhaled or aerosol remdesivir formulation;

(k) oseltamivir (optionally, TAMIFLU™) and efavirenz (optionally, SUSTIVA™), and/or zanamivir (or RELENZA™);

(l) oseltamivir (optionally, TAMIFLU™) and nevirapine (or the combination efavirenz with emtricitabine and tenofovir, or ATRIPLA™);

(m) oseltamivir (or TAMIFLU™) and amprenavir (optionally, AGENERASE™);

(n) oseltamivir (optionally, TAMIFLU™) and nelfinavir (optionally, VIRACEPT™);

(o) a thiazolide class drug, optionally nitazoxanide (optionally ALINIA™ NIZONIDE™) or tizoxanide (or 2-Hydroxy-N-(5-nitro-2-thiazolyl)benzamide), with or in combination with any of (a) to (hh), or any drug or drug combination as provided herein, optionally a thiazolide class drug, optionally nitazoxanide, with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin; or a thiazolide class drug (optionally, nitazoxanide or tizoxanide) and oseltamivir (or TAMIFLU™), and optionally the thiazolide class drug (optionally, nitazoxanide or tizoxanide) is formulated or administered with ribavirin or tribavirin (or COPEGUS™, REBETOL™, or VIRAZOLE™), and an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin;

(p) plitidepsin (also known as dehydrodidemnin B), or APLIDIN™ (PharmaMar, S. A.);

(q) an inhibitor or S-phase kinase-associated protein 2 (SKP2), or dioscin, or niclosamide, or NICLOCIDE™, FENASAL™, or PHENASAL™;

(r) ribavirin or tribavirin (or COPEGUS™, REBETOL™, or VIRAZOLE™) interferon beta 1b, or a combination of ribavirin and interferon beta, or a combination of lopinavir and ritonavir (or NORVIR™) and interferon-beta-1b;

(s) abacavir, acyclovir, or optionally ACICLOVIR™, adefovir, amantadine, ampligen, amprenavir (optionally, AGENERASE™), aprepitant, umifenovir (or ARBIDOL™), atazanavir, atripla, balavir, baloxavir marboxil (XOFLUZA™) bepotastine, bevirimat, bictegravir, a combination of bictegravir and emtricitabine and tenofovir alafenamide (or BIKTARVY™), brilacidin, bivalirudin (or BIVALITROBAN™), cidofovir, caspofungin, lamivudine and zidovudine (optionally, COMBVIR™), cobicstat, colisitin, cocaine, darunavir, delavirdine, descovy, didanosine, docosanol, dolutegravir, ecoliever, edoxudine, efavirenz (optionally, SUSTIVA™), elvitegravir, emtricitabine, enfuvirtide, entecavir, epirubicin, epoprostenol, etravirine, famciclovir, fomivirsen, fosamprenavi, foscarnet, fosfonet, galidesivir, ibacitabine, icatibant, idoxuridine, ifenprodil, imiquimod, imunovir, indinavir, inosine, an interferon (optionally interferon type I, interferon type II and/or interferon type III), lamivudine (or EPIVIR™, ZEFFIX™), lopinavir, loviride, ledipasvir, leronlimab, maraviroc, methisazone, moroxydine, nelfinavir, nevirapine, nexavir, nitazoxanide (optionally ALINIA™, NIZONIDE™), norvir, a nucleoside analogue or derivative (optionally brincidofovir (or TEMBEXA™), didanosine (or VIDEX™), favipiravir (also known as T-705 or AVIGAN™, or favilavir, Toyama Chemical, Fujifilm, Japan, or FABIFLU™, Glenmark Pharmaceuticals), vidarabine, galidesivir (optionally, BCX4430, IMMUCILLIN-A™), remdesivir (optionally, GS-5734™, Gilead Sciences), cytarabine, gemcitabine, emtricitabine, lamivudine, zalcitabine, abacavir, acyclovir, entecavir, stavudine, telbivudine, zidovudine, idoxuridine and/or trifluridine or any combination thereof), oseltamivir (or TAMIFLU™), peginterferon alfa-2a, penciclovir, peramivir (optionally, RAPIVAB™), perfenazine, pleconaril, plurifloxacin, podophyllotoxin, pyramidine, raltegravir, rifampicin, ribavirin or tribavirin (or COPEGUS™, REBETOL™, or VIRAZOLE™), rilpivirine, rimantadine, ritonavir (or NORVIR™) saquinavir, sofosbuvir, stavudine, telaprevir, tegobuv, tenofovir alafenamide, tenofovir disoproxil, tenofovir, tipranavir, trifluridine, trizivir, tromantadine, truvada, valaciclovir (optionally, VALTREX™), valganciclovir, valrubicin, vapreotide, vicriviroc, vidarabine, viramidine, velpatasvir, vivecon, zalcitabine, zanamivir (optionally, RELENZA™), zidovudine, an immunosuppressive drug (optionally tocilizumab or atlizumab, or ACTEMRA™, or ROACTEMRA™) or any combination thereof;

(t) a mucolytic therapy or drug, optionally acetylcysteine, ambroxol, bromhexine (or BISOLVON™), carbocisteine, erdosteine, mecysteine or dornase alfa, or an expectorant, optionally guaifenesin;

(u) a viral, or a coronavirus or a COVID-19, protease inhibitor, optionally ASC09 (CAS registry no. 1000287-05-7) (Janssen Research and Development, LLC), ritonavir (or NORVIR™) or ASC09 and ritonavir, or a JAK1/2 inhibitor (optionally baricitinib), optionally compound 11r (University of Lubeck, Germany, see optionally, Zhang et al J. Med Chem 2020, Feb. 11, 2020), or darunavir, cobicstat or darunavir and cobicstat;

(v) an angiotensin-converting enzyme 2 (ACE2) inhibitor, optionally to block the site of viral spike protein interaction for anti-SARS-CoV-2 infection control;

(w) an anti-vascular endothelial growth factor (VEGF) (optionally VEGF-A) drug or antibody, optionally bevacizumab;

(x) a protease inhibitor, optionally danoprevir, optionally a serine protease inhibitor, optionally camostat or narlaprevir (optionally ARLANSA™);

(y) anti-PD-1 checkpoint inhibitor, optionally camrelizumab;

(z) a compound or antibody capable of binding complement factor C5 and blocking membrane attack complex formation, optionally eculizumab;

(aa) a cathepsin inhibitor, optionally a cathepsin K, B or L inhibitor, optionally relacatib;

(bb) thalidomide, or thalidomide and glucocorticoid (optionally low-dose glucocorticoid), or and thalidomide and celecoxib;

(cc) an antibacterial antibiotic or a macrolide drug, wherein optionally the macrolide drug comprises azithromycin, optionally dosaged at between about 50 mg to about 2000 mg per dose or per day (optionally, ZITHROMAX™, or AZITHROCIN™, optionally an oral extended- or delayed-release formulation of azithromycin, or ZMAX™), clarithromycin (optionally, BIAXIN™), erythromycin (optionally, ERYTHROCIN™), or fidaxomicin (optionally, DIFICID™ or DIFICLIR™), troleandomycin (optionally, TEKMISIN™), tylosin (optionally, TYLOCINE™ or TYLAN™), solithromycin (optionally, SOLITHERA™), oleandomycin (or SIGMAMYCINE™), midecamycin, roxithromycin, kitasamycin or turimycin, josamycin, carbomycin or magnamycin, and/or spiramycin, and optionally the antibacterial antibiotic comprises a tetracycline class drug, a glycylcycline or a fluorocycline class drug, or an analogue thereof, and optionally the tetracycline, glycylcycline or fluorocycline drug or analogue thereof comprises or is: tetracycline or SUMYCIN™; chlortetracycline or AUREOMYCIN™; oxytetracycline; demeclocycline or DECLOMYCIN™, DECLOSTATIN™, LEDERMYCIN™, BIOTERCICLIN™, DEGANOL™, DETECLO™, DETRAVIS™, MECICLIN™, MEXOCINE™, CLORTETRIN™; lymecycline; meclocycline; metacycline; minocycline or MINOCIN™; rolitetracycline; doxycycline, or DORYX™, DOXYHEXA™, DOXYLIN™; tigecycline or TYGACIL™; eravacycline or XERAVA™; sarecycline or SEYSARA™; omadacycline or NUZYRA™; or any combination thereof, and optionally the antibacterial antibiotic or macrolide drug, optionally azithromycin (or ZMAX™), is administered in combination with, and/or is combined with, chloroquine (or ARALEN™), amodiaquine (or AMDAQUINE™, AMOBIN™), chloroquine phosphate, chloroquine diphosphate and/or hydroxychloroquine (optionally, PLAQUENIL™), and the combination is administered commencing on the first, second, third, fourth, fifth, sixth, seventh, eighth, ninth and/or tenth day of therapy, or is administered for 1, 2, 3, 4, 5, 6, 7, 8, 9, 10 or up to 20 or more days, or for between about 1 to 21 days or longer, or is administered until within 1, 2, 3, 4, 5, 6, 7, 8, 9, 10 or up to 20 or more days of ending the therapy for treating, preventing, ameliorating, slowing the progress of, decreasing the severity of or preventing the coronavirus infection, and optionally the chloroquine (or ARALEN™), chloroquine phosphate, amodiaquine (or AMDAQUINE™, AMOBIN™), chloroquine diphosphate and/or hydroxychloroquine (optionally, PLAQUENIL™) is administered the entire length of the treatment but the azithromycin, optionally dosaged at between about 50 mg to about 2000 mg per dose or per day (optionally, ZITHROMAX™, or AZITHROCIN™, optionally an oral extended-release formulation of azithromycin, or ZMAX™) administration is halted or ceased after two, three, four, five or six days after treatment is commenced, and optionally the azithromycin administration is replaced by a tetracycline class drug, and optionally the tetracycline class drug comprises doxycycline, or DORYX™, DOXYHEXA™, DOXYLIN™ administration, and optionally the antibacterial antibiotic, optionally azithromycin (optionally, ZITHROMAX™, or AZITHROCIN™, optionally dosaged at between about 50 mg to about 2000 mg per dose or per day, and optionally an oral extended-release formulation of azithromycin, or ZMAX™), is administered or formulated with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and/or cholecalciferol (vitamin D3) or calcifediol, and optionally the antibacterial antibiotic comprises an antimycobacterial drug, and optionally the antimycobacterial drug comprises clofazimine (optionally LAMPRENE™);

(dd) an avermectin class drug such as ivermectin (optionally STROMECTOL™, SOOLANTRA™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, optionally dosaged and/or administered at about 5 microgram/kg to about 1 gram (g) per day, optionally formulated or administered at about 1 to 10, 12, 15, 20, 30, 40, 50, 60, 70, 80, 100, 120, 140, 160, 180, 200, 220 or 240 mg per day, or between about 1 to 240 mg per day, or between about 3 to 240 mg per day, optionally formulated or administered with an antibiotic (optionally azithromycin, minocycline, amoxicillin, niclosamide, nitazoxanide, hydroxychloroquine or doxycycline, and optionally the doxycycline is at between about 25 to 600 mg per dose or per day, or at about 100 mg per dose or per day, and optionally the azithromycin is at between about 50 mg to 2000 mg per dose or per day), optionally as a single or a divided dose, and optionally formulated and administered as an inhalant or a mist (optionally using a nebulizer, nasal spray or equivalent), optionally formulated as an aerosol, spray, mist, liquid or powder, optionally formulated as an aerosol, spray, mist, liquid or powder, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is formulated with and/or administered with chloroquine (or ARALEN™), chloroquine phosphate, chloroquine diphosphate and/or hydroxychloroquine (optionally, PLAQUENIL™) with or without zinc (optionally a zinc sulphate, acetate, gluconate or picolinate or any zinc salt), and optionally this combination is administered weekly, or every two week, or one every 5 to 28 days, as a prophylactic, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered alone in the morning (AM), and an antibiotic (optionally doxycycline) and/or a chloroquine (optionally, ARALEN™), chloroquine phosphate, chloroquine diphosphate and/or hydroxychloroquine (optionally, PLAQUENIL™) is administered in the afternoon and/or evening, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered alone for 1, 2, 3, 4, 5, 6, 7, 8, 9, 10 or up to 20 or more days, followed by administration of an antibiotic (optionally doxycycline) for a corresponding period of days, and optionally repeating the cycle of dosaging, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is formulated or administered with:

(i) at least one antibiotic (wherein optionally the antibiotic is doxycycline(optionally, DORYX™, DOXYHEXA™, DOXYLIN™) (optionally formulated or administered at a dosage of between about 25 mg to 600 mg per dose or per day), or azithromycin (optionally, ZITHROMAX™, or AZITHROCIN™, optionally dosaged at between about 50 mg to about 2000 mg per dose or per day, optionally an oral extended-release formulation of azithromycin, or ZMAX™) (optionally formulated or administered at a dosage of between an about 50 mg to 2000 mg);

(ii) chloroquine (or ARALEN™), chloroquine phosphate, chloroquine diphosphate and/or hydroxychloroquine (optionally, PLAQUENIL™) (optionally formulated or administered at a dosage of between an about 10 mg to 2000 mg per day);

(iii) a zinc (optionally a zinc sulphate, acetate, gluconate or picolinate or any zinc salt) optionally formulated or administered at a dosage of between about 1 mg to 250 mg; and/or (iv) at least one vitamin, and optionally the at least one vitamin comprises: vitamin C optionally formulated or administered at a dosage of between about 500 to 5000 units (U) per dose, and/or Vitamin D (or cholecalciferol) optionally formulated or administered at a dosage of between about 3,000 to 100,000 units per day, or between about 10,000 to 50,000 units a day, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered or formulated alone or in combination with any of the above (i) to (iv) (for example, at least one antibiotic, chloroquine (or ARALEN™) chloroquine phosphate, chloroquine diphosphate and/or hydroxychloroquine (optionally, PLAQUENIL™), zinc or any zinc salt and/or at least one vitamin are formulated (and administered) as oral formulations (for example, as tablets, capsules, powders, gels or geltabs), injectable formulations, powders (for example, for inhalation or for addition to an ingestible liquid) or liquids (for example, for ingestion, infusion or injection);

(ee) chloroquine (or ARALEN™), chloroquine phosphate, chloroquine diphosphate and/or hydroxychloroquine (optionally, PLAQUENIL™) alone or with (or formulated with) or in combination with any of (a) to (bb), or chloroquine, chloroquine phosphate, chloroquine diphosphate and/or hydroxychloroquine (optionally, PLAQUENIL™) and oseltamivir (or TAMIFLU™);

(ff) chloroquine (optionally, ARALEN™), chloroquine phosphate, chloroquine diphosphate and/or hydroxychloroquine (optionally, PLAQUENIL™) alone or with:
  (i) an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, optionally at a dosage of between about 3 to 340 mg per day, or about 6 mg to 60 mg, or about 10 mg to 80 mg dosages, or about 12 to 50 mg dosages;
  (ii) vitamin D, vitamin D2 (or ergocalciferol), vitamin D3 (or cholecalciferol) optionally at a dosage of between about 3,000 to 100,000 units per day, or between about 10,000 to 50,000 units a day, and/or
  (iii) with (i) and (ii) and zinc (optionally a zinc sulphate, acetate, gluconate or picolinate or any zinc salt) optionally at a dosage of between about 1 mg to 250 mg, or (iv) the combination of (iii) also with a tetracycline class drug, wherein optionally the tetracycline class drug comprises doxycycline, or DORYX™, DOXYHEXA™, DOXYLIN™, optionally dosages at between about 25 mg to 600 mg per day or per dose, optionally between about 100 mg to 500 mg, or a between about 200 mg to 400 mg per dose or per day;

(gg) colchicine, or COLCRYS™, MITIGARE™, optionally administered or dosaged at between about 0.5 mg to 20 mg, or about 1 mg to 15 mg, or about 3 mg to 10 mg, or about 4 mg to 6 mg, per day for a period of between about 7 and 21 days, or about 14 days, and optionally also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily);

(hh) a corticosteroid or glucocorticoid class drug such as ciclesonide (or ALVESCO™, OMNARIS™, OMNIAIR™, ZETONNA™ or ALVESCO™) budesonide (optionally RHINOCORT™ or PULMICORT™), prednisolone (or ORAPRED™), methylprednisolone, prednisone (or DELTASONE™ or ORASONE™) or hydrocortisone (or CORTEF™), or a selective estrogen receptor modulator (SERM), or toremifene (or FARESTON™), or clomifene or clomiphene (or CLOMID™, SEROPHENE™), wherein optionally the corticosteroid or glucocorticoid class drug (optionally ciclesonide) is inhaled;

and optionally the corticosteroid class drug (for example budesonide) is administered by inhalation, for example, in a nebulized form, for example, between about 1 mg to 12 mg per day of budesonide is administered by inhalation, or between about 6 to 80 mg per day of prednisolone is administered orally, or between about 6 to 100 mg per day of prednisone is administered orally, or between about 30 to 400 mg per day of hydrocortisone is administered orally, and optionally the corticosteroid class drug is formulated as a powder or for administration in an inhaler or by nasal spray, or for rectal administration, and optionally the corticosteroid class drug (for example, budesonide) is administered together with or in combination with 10 mg to 80 mg, an antibiotic (optionally azithromycin or a tetracycline class drug, wherein optionally the tetracycline class drug comprises doxycycline, or DORYX™, DOXYHEXA™, DOXYLIN™, zinc or any zinc salt and/or a vitamin (optionally vitamin D or calcifediol, D2 (or ergocalciferol), D3 (or cholecalciferol), C, E, B12, B6);

(ii) an anti-androgen drug, and optionally the anti-androgen drug is bicalutamide, optionally CASODEX™, or dutasteride (or AVODART™), and optionally the anti-androgen drug is a nonsteroidal anti-androgen (NSAA) or an androgen receptor (AR) antagonist, and optionally the NSAA or AR antagonist comprises proxalutamide (or its developmental name GT-0918) (Suzhou Kintor Pharmaceuticals, Inc., a subsidiary of Kintor Pharmaceutical Limited), or flutamide (or niftolide, or EULEXIN™), or bicalutamide (or CASODEX™) or enzalutamide (or XTANDI™), and optionally the anti-androgen drug comprises a 5α-reductase inhibitor, and optionally the 5α-reductase inhibitor comprises finasteride (or PROSCAR™, PROPECIA™, or FINIDE™)

and optionally the anti-androgen drug, or NSAA, or proxalutamide or bicalutamide, is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin;

and optionally the anti-androgen drug, or NSAA, or bicalutamide, proxalutamide, flutamide or niftolide, bicalutamide, enzalutamide or dutasteride, is administered at dosages of about 50 to 100 mg optionally administered once, twice (BID), three times (TID) or four times a day, or is administered at dosages of about 50 to 100 mg per day, and optionally the anti-androgen drug, or NSAA, or bicalutamide, proxalutamide, flutamide or niftolide, bicalutamide, enzalutamide or dutasteride, is administered with an avermectin class drug, or ivermectin, optionally also administered with hydroxychloroquine, zinc and/or a vitamin (optionally vitamin D (optionally vitamin D2, or ergocalciferol, or Vitamin D3 or cholecalciferol, optionally administered at about 1000 to 4000 ugm/day) or vitamin C, B or A;

and optionally bicalutamide is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and optionally bicalutamide is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin;

(jj) a hydrocortisone or cortisol (optionally CORTEF™, SOLUCORTEF™), optionally hydrocortisone sodium succinate or hydrocortisone acetate or dexamethasone (optionally DEXTENZA™, OZURDEX™, NEOFORDEX™);

(kk) an alpha-ketoamide (α-ketoamide), wherein optionally the alpha-ketoamide is a structure as described by Zhang et al, J. Med. Chem. 2020, 63, 9, 4562-4578, or Meng et al Chem. Sci. (2019) vol. 10, pg 5156 (optionally the structure KAM-2), and optionally the alpha-ketoamide is formulated or administered as an inhalant or a powder or mist, and optionally formulated or administered with (optionally as an inhalant): an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin; an antibiotic (optionally azithromycin or a tetracycline class drug, wherein optionally the tetracycline class drug comprises doxycycline, or DORYX™, DOXYHEXA™, DOXYLIN™); chloroquine (or ARALEN™), chloroquine phosphate, chloroquine diphosphate and/or hydroxychloroquine (optionally, PLAQUENIL™); zinc or any zinc salt; remdesivir (optionally, GS-5734™, Gilead Sciences); oseltamivir (or TAMIFLU™); and/or, hydrocortisone; or, any combination thereof;

(ll) a compound, drug or formulation that decreases stomach acid production or decreases stomach pH, wherein optionally the compound, drug or formulation comprises famotidine, or PEPCID™, and optionally the famotidine is administered at a dosage of between about 10 to 60 mg per day, or between about 20 to 40 mg per day, and optionally the famotidine is administered is administered with: an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and/or a tetracycline tetracycline class drug, and optionally the tetracycline class drug comprises doxycycline, or DORYX™, DOXYHEXA™, DOXYLIN™;

(mm) a dendrimer, optionally astodrimer sodium (Starpharma, Melbourne, Australia);

(nn) an antihistamine class drug such as azelastine, or ASTELIN™, OPTIVAR™, ALLERGODIL™, brompheniramine, fexofenadine or ALLEGRA™ pheniramine or AVIL™, or chlorpheniramine;

(oo) a selective serotonin reuptake inhibitor (SSRI) class drug, optionally fluvoxamine, or LUVOX™, FAVERIN™, FLUVOXIN™;

(pp) a nicotinic antagonist, a dopamine agonist or a noncompetitive N-Methyl-d-aspartic acid or N-Methyl-d-aspartate (NMDA) antagonist, wherein optionally the nicotinic antagonist, dopamine agonist or noncompetitive NMDA antagonist is 1-adamantylamine or amantadine, or GOCOVRI™, SYMADINE™, SYMMETREL™, optionally administered or dosaged at between about 50 mg to 150 mg, or about 100 mg, per day for a period of between about 7 and 21 days, or about 14 days, and optionally the nicotinic antagonist, dopamine agonist or noncompetitive NMDA antagonist is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally the amantadine is formulated or administered at 100 mg per day for the first two days of treatment, which optionally can then be elevated to 100 mg twice daily, optionally for the next 10 days;

(qq) an immunosuppressive drug, wherein optionally the immunosuppressive drug comprises tocilizumab or atlizumab, or ACTEMRA™, or ROACTEMRA™, or a calcineurin inhibitor (CNI), wherein the CNI comprises ciclosporin (or cyclosporine or cyclosporin), or NEORAL™, or SANDIMMUNE™, or tacrolimus, or PROTOPIC™, or PROGRAF™, and optionally the immunosuppressive drug is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally the calcineurin inhibitor (CNI), wherein the CNI comprises ciclosporin (or cyclosporine or cyclosporin) is formulated combination of CNI (optionally cyclosporine) at a dose of 3 mg/kg (180 mg daily) together with 12 mg ivermectin once, and optionally also plus zinc 50 mg base and doxycycline 100 mg bid, optionally all for 10 days;

(rr) a protein kinase inhibitor, wherein optionally the protein kinase inhibitor is a p38 mitogen-activated protein kinase inhibitor, or ralimetinib, and optionally the protein kinase inhibitor is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily);

(ss) an anti-inflammatory therapy or at least one anti-inflammatory therapy drug, wherein optionally the anti-inflammatory therapy or drug comprises: a sphingosine kinase-2 (SK2) selective inhibitor (optionally, opaganib (optionally, YELIVA™), sirolimus, a JAK1/2/TYK2 inhibitor (optionally ruxolitinib), an anti-CD47 mAb (optionally meplazumab), a cyclooxygenase (COX) (optionally, COX2) inhibitor, a glucocorticoid (optionally a synthetic glucocorticoid, hydrocortisone, dexamethasone (or DEXTENZA™, OZURDEX™, or NEOFORDEX™) or cortisol, or CORTEF™) or ciclesonide (or ALVESCO™, OMNARIS™, OMNIAIR™, ZETONNA™ or ALVESCO™), plitidepsin or dehydrodidemnin B, or APLIDIN™, or a nonsteroidal anti-inflammatory drug (NSAID), wherein optionally the NSAID comprises indomethacin (or indomethacin) or INDOCID™ or INDOCIN™, or naproxen, or NAPROSYN™ or ALEVE™, or a cyclooxygenase inhibitor, or a COX-1 or an COX-2 inhibitor, or aspirin, or ibuprofen or ADVIL™, MOTRIN™ or NUROFEN™, or celecoxib or CELEBREX™, or parecoxib or DYNASTAT™, or etoricoxib or ARCOXIA™, and optionally the anti-inflammatory therapy or anti-inflammatory therapy drug is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally opaganib, or YELIVA™, or opaganib, or YELIVA™ administered or formulated together with an oral and/or inhaled or aerosol chloroquine (or ARALEN™), chloroquine phosphate, chloroquine diphosphate and/or hydroxychloroquine (optionally, PLAQUENIL™)

and optionally the opaganib or YELIVA™ is formulated or administered at a dosage of QD (once a day), bid (twice a day) or tid (three times a day) at a dosage of between about 100 to 600 mg per day or per dosage, or at about 100, 200, 300, 400, 500 or 600 mg per day or per dosage, and optionally the opaganib, or YELIVA™ is also administered or formulated with an antibiotic (optionally azithromycin or doxycycline), ivermectin (optionally at 12 mg ivermectin, optionally administered on days 1, 3, 6 and 8), hydroxychloroquine (optionally, PLAQUENIL™) and/or zinc or any zinc salt (optionally zinc sulfate, optionally at (50 mg daily);

(tt) a calcium channel blocker, or verapamil (or ISOPTIN™, CALAN™), or a voltage gated potassium (KCNH2) channel or a voltage gated calcium channel (CACNA2D2) blocker, or amiodarone (or CORDARONE™, NEXTERONE™);

(uu) suramin, or ANTRYPOL™, BAYER 305™, or GERMANIN™

(vv) a peroxisome proliferator-activated receptor (PPAR) agonist, wherein optionally the PPAR agonist comprises fenofibrate, or TRICOR™, FENOBRAT™, FENOGLIDE™, or LIPOFEN™, or a combination of fenofibrate and simvastatin, or CHOLIB™, optionally the PPAR agonist comprises a combination of fenofibrate and pravastatin, or PRAVAFENIX™, or the PPAR agonist comprises bezafibrate, or BEZALIP™, or combination of bezafibrate and chenodeoxycholic acid, or HEPACONDA™, or aluminium clofibrate, or alfibrate, or ciprofibrate, or clinofibrate or LIPOCLIN™, or clofibrate or ATROMID-S™, or clofibride, or gemfibrozil or LOPID™, or ronifibrate, or simfibrate or CHOLESOLVIN™, or any combination thereof, (ww) a synthetic nucleoside analog or derivative, or N4-hydroxycytidine, or a prodrug of N4-hydroxycytidine, optionally molnuvpiravir (Merck), or favipiravir (also known as T-705 or AVIGAN™, or favilavir, Toyama Chemical, Fujifilm, Japan, or FABIFLU™, Glenmark Pharmaceuticals), wherein the synthetic nucleoside analog or derivative, or N4-hydroxycytidine, or the prodrug of N4-hydroxycytidine, optionally molnuvpiravir or favipiravir, is given as between about 10 mg to 3 gm per dose, or between about 10 mg to 3 gm per day, or can be dosed either as a single dose or given one, two, three or four times a day, or is administered at 200 to 800 mg twice daily, or 200, 400, 600 or 800 mg twice daily, or at 200 to 800 mg three times a day, or at 200, 400, 600 or 800 mg three times a day, or is administered at 200 to 800 mg three times a day for between about 2 to 15 days, or for about 2, 3, 4, 5, 6, 7, 8, 9, 10, 11 or 12 days, and optionally when combined with other drugs a lower dosage is used, optionally administered at 100 or 200 mg three times a day for between about 5 to 15 days, or for about 7, 8, 9, 10, 11 or 12 days, and optionally the synthetic nucleoside analog or derivative, or N4-hydroxycytidine, or the prodrug of N4-hydroxycytidine, optionally molnuvpiravir or favipiravir, is administered with an avermectin class drug (optionally ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin), and optionally the synthetic nucleoside analog or derivative, or N4-hydroxycytidine, or the prodrug of N4-hydroxycytidine, optionally molnuvpiravir or favipiravir, is administered with an avermectin class drug (optionally ivermectin) with an antibiotic, and optionally the antibiotic comprises azithromycin, minocycline, amoxicillin, niclosamide, nitazoxanide, hydroxychloroquine or doxycycline), and optionally the synthetic nucleoside analog or derivative, avermectin class drug, and antibiotic are administered together or as separate formulations, and optionally are administered every one, two, three, four or five weeks for between about one month and one year or more;

and optionally molnuvpiravir, ivermectin and hydroxychloroquine are administered together or as separate formulations, and optionally are administered every one, two, three, four or five weeks for between about one month and one year or more;

and optionally the synthetic nucleoside analog or derivative (optionally N4-hydroxycytidine, or the prodrug of N4-hydroxycytidine, optionally molnuvpiravir or favipiravir), and antibiotic (optionally doxycycline or hydroxychloroquine) is administered with zinc (optionally a zinc sulphate, acetate, gluconate or picolinate, or zinc oxide nanoparticles, optionally at a dosage of between about 1 mg to 250 mg, or about 50 mg per day) and/or a vitamin, optionally vitamin C or D), and optionally the synthetic nucleoside analog or derivative, or N4-hydroxycytidine, or the prodrug of N4-hydroxycytidine, optionally molnuvpiravir or favipiravir, is administered with an antibiotic (optionally the antibiotic comprises azithromycin, minocycline, amoxicillin, niclosamide, nitazoxanide, hydroxychloroquine or doxycycline), optionally also administered with zinc (optionally a zinc sulphate, acetate, gluconate or picolinate, or zinc oxide nanoparticles, optionally at a dosage of between about 1 mg to 250 mg, or about 50 mg per day) and/or a vitamin, optionally vitamin C or D, and optionally any of these combinations is administered very 2, 3, 4, 5, 6, 7, 8, 9 or 10 or more days for between about 1 month and one year or more;

(xx) an antisera or an antibody or antibody or vaccine therapy for treating, preventing or ameliorating a microbial or a viral infection (optionally a coronavirus infection, optionally a COVID-19 infection) or a microbial infection (optionally a protozoan, helminthiasis, insect and/or parasitic infection), and optionally the antibody comprises a monoclonal antibody, and optionally the monoclonal antibody comprises sotrovimab (GlaxoSmithKline and Vir Biotechnology), or casirivimab, imdevimab or casirivimab and imdevimab (REGEN-COV™) (Regeneron), or bamlanivimab oretesevimab or bamlanivimab and etesevimab (Junshi Biosciences), or tocilizumab or ACTEMRA™ or ROACTEMRA™ (Hoffmann-La Roche), and optionally the vaccine comprises tozinamera or COMIRNATY™ (Pfizer), or elasomeran or SPIKEVAX™ (Moderna), or SPUTNIK V™ or Gam-COVID-Vac (Gamaleya Research Institute), or AZD1222 or COVISHIELD™ or VAXZEVRIA™ (Oxford-AstraZeneca), and optionally the antibody or antibody therapy comprises or is contained in a convalescent sera or plasma, and/or (yy) any combination of (a) to (xx), and optionally any one or several or all of (a) to (yy) with an (or formulated with or formulated as an) inhaled or aerosol formulation such as a powder or a mist or aerosol, and/or formulated with or formulated as an oral, intramuscular (IM) or intravenous (IV) formulation, wherein optionally both the inhaled (or aerosol) and the oral, IV and/or IM formulations are administered simultaneously or sequentially, and optionally the inhaled or aerosol formulation comprises chloroquine (or ARALEN™), chloroquine phosphate, chloroquine diphosphate and/or hydroxychloroquine (optionally, PLAQUENIL™) and/or oral chloroquine (or ARALEN™), chloroquine phosphate, chloroquine diphosphate and/or hydroxychloroquine (optionally, PLAQUENIL™) administered simultaneously or overlapping, and optionally the inhaled or aerosol formulation comprises an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and optionally any one or several or all of (a) to (yy), or any therapeutic combination of drugs or a drug, or a pharmaceutical dosage form as provided herein, are administered orally, intramuscularly, subcutaneously, topically, by use of an enema, intravaginally, or intravenously, or administration is by subcutaneous administration, sublingual administration, inhalation or by aerosol (optionally by inhalation of a liquid, an aerosol, a spray, a mist or a powder), by absorbable patch, by use of an implant, or by use of an enema or a suppository.

In alternative embodiments, the anti-viral drug or medication, or anti-microbial drug, is or comprises: molnupiravir, efavirenz (optionally, SUSTIVA™), tenofovir, emtricitabine and tenofovir, nevirapine (or the combination efavirenz with emtricitabine and tenofovir, or ATRIPLA™), amprenavir (optionally, AGENERASE™), nelfinavir (optionally, VIRACEPT™) and/or remdesivir (optionally, GS-5734™, Gilead Sciences), a viral RNA-dependent RNA polymerase inhibitor, optionally galidesivir, and optionally the anti-viral drug or medication is or comprises an anti-retroviral drug or drug combination, and optionally the anti-retroviral drug or drug combination comprises: darunavir and cobicistat (optionally, REZOLSTA™ or PREZCOBIX™); atazanavir (or REYATAZ™) and cobicistat (or EVOTAZ™); a nucleoside analog reverse-transcriptase inhibitor (NRTI) (optionally abacavir, or ZIAGEN™), lamivudine and dolutegravir (TRIUMEQ™); tenofovir (or disoproxil or emtricitabine) and elvitegravir and cobicistat (optionally, STRIBILD™); tenofovir (or disoproxil or emtricitabine) and elvitegravir and cobicistat (COMPLERA™ or EVIPLERA™); molnupiravir, efavirenz (optionally, SUSTIVA™), emtricitabine and tenofovir (ATRIPLA); lamivudine, nevirapine and stavudine (optionally, TRIOMUNE™); atazanavir (or REYATAZ™) and cobicistat (optionally, EVOTAZ™); lamivudine and raltegravir (optionally, DUTREBIS™); lamivudine and dolutegravir (or DOVATO™); doravirine, lamivudine and tenofovir (optionally, DELSTRIGO™); or lamivudine, zidovudine and nevirapine (optionally, CUOVIR-N™);

and optionally the additional anti-viral drug or medication, or anti-microbial drug, is formulated with the chloroquine (optionally, ARALEN™), chloroquine phosphate, chloroquine diphosphate, hydroxychloroquine (optionally, PLAQUENIL™), lopinavir, ritonavir (or NORVIR™) and/or oseltamivir or is formulated separately from the chloroquine (optionally, ARALEN™), chloroquine phosphate, chloroquine diphosphate, hydroxychloroquine (optionally, PLAQUENIL™), lopinavir, ritonavir (or NORVIR™) and/or oseltamivir, and optionally the anti-viral drug or medication, or anti-microbial drug, or palliative agent comprises or further comprises: magnesium (Mg, optionally administer intravenously (IV) to maintain a blood concentration of between about 2.0 and 2.4 mmol/1); zinc or any zinc salt (optionally a zinc sulphate, acetate, gluconate or picolinate, optionally administered at about 75 to 100 mg/day or at a dosage of between about 1 mg to 250 mg); at least one vitamin, wherein optionally the at least one vitamin comprises vitamin K, vitamin D or calcifediol (optionally D2 (or ergocalciferol) or Vitamin D3 or cholecalciferol), optionally administered at about 1000 to 4000 ugm/day), vitamin B6 (or pyridoxine), vitamin B12, vitamin E, and/or vitamin C (optionally administered at 500 mg bid); a flavonoid, plant flavonol or quercetin optionally administered at between about 250 to 500 mg bid; atorvastatin, or LIPITOR™, SORTIS™ (optionally administered at between about 40 mg/day to 80 mg/day); or, melatonin, or CIRCADIN™, SLENYTO™ (optionally between about 6 to 12 mg a day, optionally, at night), any of which are optionally given enterally or parenterally.

In alternative embodiments, provided are kits comprising a vaccine and/or an attenuated and/or live causative agent of infection, and at least one antibiotic and/or anti-viral drug capable of killing a causative agent of the infection, or completely or partially inhibiting the ability of the causative agent of the infection to replicate or become infectious or cause pathology in an individual, as described herein or used in any method as provided herein, wherein optionally the kit comprises instructions for practicing a method as provided herein.

In alternative embodiments of methods and kits as provided herein, the (i) 1R,2S,5S)-N-[(1S)-1-cyano-2-[(3S)-2-oxopyrrolidin-3-yl]ethyl]-3-[(2S)-3,3-dimethyl-2-(2,2,2-trifluoroacetamido)butanoyl]-6,6-dimethyl-3-azabicyclo[3.1.0]

hexane-2-carboxamide, or a compound having the following structure and molecular weight:

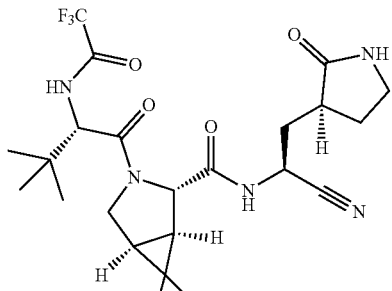

PF-07321332

C23H32F3N5O4 FW: 499.527 or stereoisomer, or enantiomer, or deuterated version thereof, and (ii) ritonavir, are formulated together, or separately, and optionally are formulated together or separately in or as a liquid (optionally to be administered as a drink or in drops, optionally as nasal drops or in a mist), a tablet, a capsule, a gel, a geltab, a powder, a lozenge, an aerosol or spray.

In alternative embodiments of methods and kits as provided herein, the anti-viral drug combination is formulated in or as a pharmaceutical dosage form, optionally formulated to be administered orally, intramuscularly, subcutaneously, topically, by use of an enema, intravaginally, or intravenously, or formulated for subcutaneous administration, sublingual administration, inhalation or by aerosol (optionally by inhalation of a liquid, an aerosol, a spray, a mist or a powder), by absorbable patch, by use of an implant, or by use of an enema or a suppository.

In alternative embodiments of methods and kits as provided herein, the (a) 1R,2S,5S)-N-[(1S)-1-cyano-2-[(3S)-2-oxopyrrolidin-3-yl]ethyl]-3-[(2S)-3,3-dimethyl-2-(2,2,2-trifluoroacetamido)butanoyl]-6,6-dimethyl-3-azabicyclo[3.1.0]hexane-2-carboxamide, or a compound having the following structure and molecular weight:

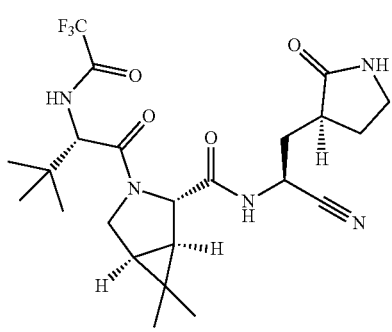

PF-07321332

C23H32F3N5O4 FW: 499.527 or stereoisomer, or enantiomer, or deuterated version thereof, and/or (b) ritonavir, is or are administered:

(a) at a dosage of QD (once a day), bid (twice a day) or tid (three times a day) at a dosage of between about 100 to 600 mg per day or per dosage, or at about 100, 200, 300, 400, 500 or 600 mg per day or per dosage, or (b) at a dosage of between about 10 mg to 3 gm per dose, or between about 10 mg to 3 gm per day, or 12 mg or 3 mg/kg orally twice daily, or 125 mg orally twice daily or 520 mg/130 mg solution twice per day (optionally administered with efavirenz, fosamprenavir, nelfinavir, or nevirapine), or (c) is dosed either as a single dose or given one, two, three or four times a day, or (d) at 200 to 800 mg twice daily, or 200, 400, 600 or 800 mg twice daily, or at 200 to 800 mg three times a day, or at 200, 400, 600 or 800 mg three times a day, or is administered at 200 to 800 mg three times a day for between about 2 to 15 days, or for about 2, 3, 4, 5, 6, 7, 8, 9, 10, 11 or 12 days, (e) for pediatric patients dosage at 16 mg or 4 mg/kg orally twice daily, or (f) when combined with other drugs a lower dosage, optionally administered at 100 or 200 mg three times a day for between about 5 to 15 days, or for about 7, 8, 9, 10, 11 or 12 days.

The details of one or more exemplary embodiments of the invention are set forth in the description below. Other features, objects, and advantages of the invention will be apparent from the description, and from the claims.

All publications, patents, patent applications cited herein are hereby expressly incorporated by reference in their entireties for all purposes.

DETAILED DESCRIPTION

In alternative embodiments, provided are methods for treating, ameliorating, decreasing the chances of having any adverse effects from, decreasing the severity of adverse effects from, or preventing an infection in an individual in need thereof, including humans and animals, by administration of an antibiotic and/or an anti-viral drugs and a vaccine directed to a causative agent of the infection, and/or an inactivated or attenuated causative agent of the infection, or the live, viable or infectious causative agent of the infection. In alternative embodiments, the infection (or causative agent of the infection) is parasitic, bacterial or viral. In alternative embodiments, the viral infection is a coronavirus infection such a Covid-19 infection.

In alternative embodiments, methods as provide herein prevent or decrease the prevalence or severity of "vaccine breakthrough infections" after vaccination, where external mutants of the infection's causative agent develop and infect or re-infect patients in spite of the fact that they have undergone immunization, for example, to prevent a Covid-19 infection. Thus, in alternative embodiments, methods as provided herein comprise combining an effective anti-microbial (for example anti-viral) treatment (for example, a drug or a mixture of drugs or other therapeutics) with an anti-microbial vaccine to prevent in vivo mutations (and thus also prevent a vaccine breakthrough infection) of an infectious agent such as virus, for example, a coronavirus such as COVID-19 or variant thereof.

In alternative embodiments, methods as provide herein provide a solution to the problem of imperfect vaccine disease prevention, where a bigger and/or better vaccine or multiple vaccinations are ineffective because science will never keep up with the continuing viral mutations. In alternative embodiments, methods as provide herein prevent replication of newly-inhaled mutants in the already vaccinated or 'about to be vaccinated' population.

In alternative embodiments, methods as provide herein comprise an added anti-replication method of treatment in addition to vaccination to protect the immunized population from mutants entering, replicating, and further mutating in the immunized population. In alternative embodiments, methods as provide herein prevent replication and thus prevent an ongoing viral mutation, a method utilized by the mutant to escape neutralizing antibodies and destruction. No replication, no mutation.

In alternative embodiments, methods as provide herein comprise combining an effective anti-microbial (for example anti-viral) treatment (for example, a drug or a mixture of drugs or other therapeutics) with an anti-microbial vaccine such as a DNA vaccine such as an adenovirus-based vaccine, an mRNA vaccine, a peptide-based vaccine, an inactivated pathogen-based vaccine, and/or an vaccine manufactured by:

Sanofi (optionally VAT00002 or VAT00008),
GlaxoSmithKline,
Takeda Pharmaceutical (optionally TAK-019),
Pfizer (optionally tozinamera or COMIRNATY™),
Moderna (optionally elasomeran or SPIKEVAX™)
Novavax (optionally vaccine to SARS VLPs S protein and influenza M1 protein),
CanSino Biologics,
Inovio,
Sinovac,
BioNTech,
Johnson and Johnson,
Valneva (France) and Dynavax Technologies (optionally VLA2001 and VLA2101),
Sinopharm (or China National Pharmaceutical Group Corporation),
Emergent BioSolutions (optionally human polyclonal hyperimmune serum with antibodies to SARS-CoV-2),
Bharat Biotech (optionally COVAXIN®),
The Rockefeller University (optionally vaccine toMVA S alone, or MVA-S prime and Ad5-S boost),
Helmholtz Centre for Infection Research; Technical University Munich; German Center for Environmental Health (optionally vaccine to NC protein add-mixed with MALP-2 by intranasal route and boosting with MVA-NC by intramuscular route),
University of Manitoba; University of Pennsylvania School of Medicine; Southern Research Institute; Fox Chase Cancer Institute (optionally vaccine to Heterologous Adenoviral prime boost AdHu5 s AdC7-nS),
University of North Carolina at Chapel Hill, USA (optionally vaccine to VEEV replicon particles expressing the SARS-CoV S),
National Institute of Infectious Diseases, Japan (optionally vaccine to recombinant D1 expressing S protein),
Beijing Institute of Genomics, China (optionally vaccine to Recombinant trunctuated S—N fusion protein),
Saitama Medical University; Josai University; Nippon Oil and Fat Corporation; National Institute of Infectious Diseases, Japan (optionally vaccine to recombinant peptide N223 on liposomes),
Chinese Center for Disease Control and Prevention; Canadian Science Centre for Human and Animal Health (optionally vaccine to Recombinant TM-truncated S protein),
HKU-Pasteur Research Centre; The University of Hong Kong; National Institutes of Health; Centers for Disease (optionally vaccine to Trimeric Spike protein),
Sun Yat-sen University, China (optionally vaccine to SARS S DNA prime and HLAA*0201 restricted peptides boost vaccine),
State Key Laboratory of Virology; Graduate University of Chinese Academy of Sciences (optionally vaccine to or as a 3a DNA vaccine),
Institute of ImmunoBiology, Shanghai Medical College of Fudan University, China (optionally vaccine to DNA prime—protein S437-459 and M1-20),
CNB-CSIC; University of Iowa (optionally vaccine to rSARSCoV-E),
International Vaccine Institute (IVI) (optionally vaccine to recombinant adenovirus expressing truncated S protein (rADV-S)),
University Health Network, Canada, and United States Center for Disease Control and Prevention (CDC) (optionally vaccine to recombinant measles virus spike protein),
Institut Pasteur (optionally vaccine to MV-SARS recombinant measles virus vaccine expressing SARS CoV antigen),
Baylor College Medicine; Sabin; New York Blood Center (NYBC); University of Texas Medical Branch (UTMB); Walter Reed Army Institute of
Research (WRAIR); National Institute of Allergy and Infectious Diseases (NIAID) (optionally vaccine to receptor binding domain (RBD) of the SARS-CoV spike (S) protein),
Vaxine Pty Ltd, Australia (optionally vaccine to SARS recombinant spike protein plus delta inulin),
Gamaleya Research Institute (optionally SPUTNIK V™ or Gam-COVID-Vac), and/or
Oxford-AstraZeneca (optionally AZD1222 or COVISHIELD™ or VAXZEVRIA™)
and others, including anti-COVID-19 vaccines.

Hence, methods as provided herein that combine antibiotic, anti-parasitic and/or anti-viral treatment with an inactivated or attenuated causative agent of an infection, or a vaccine or a live, viable or infectious causative agent of the infection (for example, a live or attenuated virus) administration, can treat, ameliorate or prevent a vaccine-breakthrough infection, as well as eradicating the infection if present pre-vaccination enhance protection and eradicate infection.

In alternative embodiments, methods as provide herein comprise administering in coordination with (for example, before, during and/or after) an anti-causative agent vaccination, or an anti-viral vaccination, and/or the inactivated or attenuated causative agent of the infection, or the live, viable or infectious causative agent of the infection (such as a live or attenuated virus) administration, any one or combination of anti-viral, anti-parasitic or anti-bacterial therapies, for example, one or more anti-COVID-19 infection medications or drugs, including for example, the drug ivermectin, or the combination of ivermectin and an antibiotic with anti-viral properties such as doxycycline or azithromycin, for example the combination of ivermectin and doxycycline or azithromycin, or the combination ivermectin and doxycycline or azithromycin and zinc or any zinc salt (an anti-viral mineral, for example, and anti-COVID-19 mineral), which optionally also can be administered in conjunction or coordination with a vitamin or vitamins such as vitamin D and/or vitamin C.

In alternative embodiments, a drug combination administered in coordination with a vaccine and/or the inactivated or attenuated causative agent of the infection, or the live, viable or infectious causative agent of the infection (optionally a live or attenuated virus) administration comprises the commencement, optionally orally or by inhalation, of the antiviral combination before, or just before, and/or the day (day zero) the vaccine and/or the inactivated or attenuated causative agent of the infection, or the live, viable or infectious causative agent of the infection (such as a live or attenuated virus) administration is given. For example, in alternative embodiments, the patient (or individual in need thereof) is given a pre-vaccine drug or anti-viral treatment for between about 1 to 10 days, or between about 2 to 21 days, depending on dosing and conditions. If the patient is already infected but asymptomatic, because of this pre-vaccination (or pre-administration of the attenuated and/or the live infectious causative agent) treatment the patient will be free, or substantially free, of the infection but not yet endowed with complete or partial immunity. In other words, because of this pre-vaccination treatment there will be no virus, or substantially no virus, to replicate in vivo after the anti-viral treatment. After administration of the anti-microbial drug or treatment (optionally, 1, 2, 3, 4, 5, 6, 7, 8, 9, 10, 11, 12, 13 or 14 or more days after a first anti-microbial drug or treatment is first administered) the vaccine is given (depending on the type of vaccine, this may be the first of a two or three injection process). In alternative embodiments, after the first dose of the vaccine or the inactivated or attenuated causative agent of the infection, or the live, viable or infectious causative agent of the infection is given, the patient is treated at day 14 (or, optionally, on day 1, 2, 3, 4, 5, 6, 7, 8, 9, 10, 11, 12, 13 or 14) with an antibiotic or antiviral, for example, with a single preventative ivermectin and antibiotic drug combination (for example, using an antibiotic with anti-viral activity such as doxycycline or azithromycin), or ivermectin and doxycycline drug combination, or ivermectin and doxycycline and zinc drug combination, or ivermectin and azithromycin and zinc or any zinc salt, or any of these combinations with additional drugs or agent or adjuncts such as one or more vitamins, for example, vitamin B, C and/or D. In alternative embodiments, the drug combination administration is repeated every 14 days (or, optionally, every 1, 2, 3, 4, 5, 6, 7, 8, 9, 11, 12, 13 or 14 or more days) for several weeks until plasma ivermectin is detectable over the 14 days. In alternative embodiments, later, the drug combination administration is repeated every 1, 2, 3, 4, 5 or 6 weeks or more.

In alternative embodiments, a second dose of the vaccine and/or the inactivated or attenuated causative agent of the infection, or the live, viable or infectious causative agent of the infection, and optionally subsequent boosters, are carried out between the intermittent (for example, every 1, 2, 3, 4, 5, 6, 7, 8, 9, 10, 11, 12, 13, 14 or up to 28 days) anti-microbial (for example, anti-viral) doses.

In alternative embodiments, combining vaccine or the inactivated or attenuated causative agent of the infection, or the live, viable or infectious causative agent of the infection with initial then intermittent anti-microbial (for example, anti-viral) administrations as provided herein achieves:
- virtual 100%, or substantial (for example, 95% or more) infectious agent (for example, COVID-19) abolition or in vivo clearance, which can be achieved by the anti-microbial (for example, anti-viral) pre-vaccination treatment arm of methods as provided herein;
- prolonged immunity, which can be achieved by administration of combined vaccine and intermittent anti-microbial (for example, anti-viral) treatments as provided herein;
- lack of novel virus replication in the patient, which can be achieved by the anti-microbial (for example, anti-viral) pre-vaccination treatment arm of methods as provided herein;
- no in vivo infectious agent (for example, virus) mutation in treated patients, as there is no or substantially no (for example, 90% to 99% reduction in) replication;
- no 'Long Covid Syndrome', because if there is no infectious agent (or substantially no infectious agent) remaining in the patient in vivo, then can be no "Long Covid Syndrome";
- no or minimal hospitalization, and no or substantially decreased number of deaths from Covid-19, because if there is no active in vivo infection there can be no progression to morbidity or mortality;
- inability or substantial decrease in risk for patients treated using the combination methods as provided herein catch or be re-infected with any strain nor any mutant strain, where patients administered methods as provided herein are induced to have combined immunity (by administration of a vaccine) and an anti-viral response induced by administration of a drug or drugs which are viral mutant agonists;
- eradication of primary viral (for example, COVID-19) infection, because patients administered methods as provided herein receive anti-microbial (for example, anti-viral) treatment at the beginning of therapy; and/or,
- ideal long-term preventative therapy for the elderly with senescent immunity by supporting waning antibody levels in the elderly patient with anti-microbial (for example, anti-viral) treatment as provided herein; and also in embodiments where ivermectin is administered, having the added benefit of rosacea improvement and prevention of scabies in aged-care facilities.

Increasing the dose of the intermittent ivermectin combination increases its anti-Covid-19 preventative power. In alternative embodiments, the dose is raised from between about 12 mg to about 36 mg, about 48 mg or about 60 mg, or the dose is raised progressively to 120 mg with few if any adverse effects. This will create a more prolonged circulating level. This is expected to be close to 100% at 4 weeks, but when combined with the vaccine could well prevent for up to 6 weeks or more. Hence, creating the possibility of reducing dosing to ×7/year. Given the use of accompanying anti-viral drugs, even if the vaccine results in lower circulation of neutralizing antibody levels and so immunity, the risk of vaccine breakthrough infection will be minimal if at all possible. Hence, this combination of anti-viral treatment together with the vaccine would be ideal therapy for prevention of infection in the elderly population with senescent immune systems.

In alternative embodiments, any vaccine will benefit from practicing methods as provided herein, particularly the mRNA vaccines, which will benefit profoundly when combined with an effective anti-viral treatment.

In alternative embodiments, methods as provided herein comprise 1 to 10 days of treatment with an ivermectin-based (or ivermectin-comprising) combination, followed by (the first dose of) vaccination, and then every 1, 2, 3, 4, 5, 6 or 7 days, and later every 8, 9, 10, 11, 12, 13 or 14 days (for example, every 7 days, then every 14 days), and later to 15, 16, 17, 18, 19, 20, 21, 22, 23, 24, 25, 26, 27 or 28 days (for example, every 7 days, then every 14 days, and later every 28 days), administer a higher dose of ivermectin, for example, 60 mg ivermectin for 4 weeks together with zinc or a zinc salt, doxycycline, vitamin D and vitamin C or other appropriate combinations. As long as one continues the anti-viral treatment based on the 60 mg ivermectin regimen, a vaccinated patient has both circulating antibodies for many months and cannot catch mutated virus (for example, COVID-19 agents), and therefore "vaccine breakthrough" will be prevented or substantially decreased and super infection with mutants will be prevented or substantially decreased.

In alternative embodiments, methods as provided herein, including for example the ivermectin, zinc or a zinc salt and doxycycline and optionally also an adjunct therapy (such as for example administering a vitamin such as vitamin C or D) is mutant agnostic. In alternative embodiments, because methods as provided herein, including for example the ivermectin combination therapy, functions and works using a different mechanism by prevention of replication within a cell, no mutants can affect its activity as has been shown by us in clinical practice in California, United States. Hence, the combination of an anti-viral with a vaccine as provided herein may be the best method of terminating the Covid-19 pandemic.

In alternative embodiments, the vaccination or the inactivated or attenuated causative agent of the infection, or the live, viable or infectious causative agent of the infection administration may need to be repeated, for example, repeated at 6 or 12 month (or between about 1 (monthly) to 12 month) intervals, but it is of no great importance whether it is 6 months or 12 months because the second arm or the therapy as provided herein, the anti-viral arm, is on board to prevent any further infection and therefore any further mutation in vivo in the patient.

In alternative embodiments, even if a mutant or variant strain becomes the predominant viral agent in a community in the future necessitating that the vaccine and/or the inactivated or attenuated causative agent of the infection, or the live, viable or infectious causative agent of the infection be adjusted (or changed) to take in (be specific for) that new mutant or variant strain, the drug combination as provided herein, for example, the ivermectin, zinc or a zinc salt and doxycycline plus adjunct treatment, can remain the same as it is mutant agnostic. Hence, any vaccine produced by any institution can be supplemented with an anti-viral combination such that no individuals will catch any viral strains once the individual has begun this program (commenced receiving treatment regimens as provided herein.

The concept of 'redundancy' of treatment is significant here; in medicine, redundant treatment is one where the medication carries extra power to cure the condition. In the event that the treatment had to be terminated early (for example, due to an allergy developing) the built-in redundancy still delivers near (substantially) 100% cure because it was designed to carry extra power. Hence, the combination of the anti-viral treatment and vaccination as provided herein carries a high level of redundancy and thus can achieve a close to 100% success rate (or a substantially completely successfully cure rate).

Although alternative embodiments of methods as provided herein are best suited to prevent and treat a virus such as a coronavirus such as a Covid-19 infection, alternative embodiments have multiple other applications. For example, in alternative embodiments, with appropriate antivirals methods as provided herein are used to prevent influenza infections. In alternative embodiments, provided are methods comprising a treatment regimen of an influenza (or other viral) vaccine followed later by antiviral agents intermittently in once a week, 2 weekly, 3 weekly, 4 weekly or less frequently spaced intervals to prevent influenza mutants from re-infecting de novo susceptible elderly patients with senescent immune system where influenza infection causes the most mortality. Other exemplary antiviral combinations administered practicing methods as provided herein comprise use of hydroxychloroquine, for example, hydroxychloroquine, azithromycin and zinc or a zinc salt.

In alternative embodiments, provided are methods comprising a treatment regimen for treating: dengue fever, Zika, HIV, hepatitis C, Ebola disease, SARS, MERS, polio, measles, chickenpox and other viral or retro-viral infections. Where current immunizations may not be adequately effective, the follow-on with intermittent antiviral therapy as provide by methods as provided herein gives extra power for the poor immune response combined with antivirals to have enough redundancy to make it clinically effective.

In alternative embodiments, provided are methods comprising use of antiviral compounds used singly or in multiple combinations, for example, antiviral compounds are administered singly or in multiple combinations, for example, before, at the time of vaccination, and/or after vaccination:

For example, in alternative embodiments, methods provided herein comprise administering in coordination with (optionally before, at the time of vaccination, and/or after vaccination of) an anti-microbial vaccine a single drug or a therapeutic combination of drugs, or a single drug, a pharmaceutical dosage form, a drug delivery device, or a product of manufacture, or the methods can comprise use of: one, two or more classes of antiviral drugs used against influenza, such as: M2 protein inhibitors (for example, amantadine and rimantadine); neuraminidase inhibitors (for example, oseltamivir, zanamivir, peramivir and laninamivir); favipiravir (also known as T-705 or AVIGAN™, or favilavir, Toyama Chemical, Fujifilm, Japan, or FABIFLU™ Glenmark Pharmaceuticals); a 5- to 6-membered heterocyclic ring such as benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline; amantadine; rimantadine; oseltamivir; zanamivir; peramivir; laninamivir; laninamivir octanoate hydrate; arbidol; ribavirin; stachyflin; ingavirin; fludase; a niclosamide compound; an emricasan compound; nitazoxanide; tizoxanide; and/or a compound selected from consisting of teriflunomide, hydroxocobalamin, ensulizole, tenonitrozole, isoliquiritigenin, nitazoxanide, febuxostat, leflunomide, fidofludimus SB-366791, emodin, diphenyl isophthalate, benzoylpas, fenobam, indobufen, 2-(2H-Benzotriazol-2-yl)-4-methylphenol, tiaprofenic acid, flufenamic acid, vitamin B12, cinanserin, 5-nitro-2-(3-phenylpropylamino)benzoic acid, veliflapon, thiabendazole, SIB 1893, anethole trithione, naringenin, phenazopyridine, fanetizole, terazosin, diacerein, CAY10505, hesperetin, suprofen, ketorolac tromethamine, piperine, pirarubicin, piraxostat, albendazole oxide, tyrphostin AG 494, genistin, fenbufen, apatinib, RITA, BF-170 hydrochloride, OSI-930, tribromsalan, pifexole, formononetin, ebselen, tranilast, benzylparaben, 2-Ethoxyethyl-p-methoxycinnamate, baicalein, nemorubicin, rutaecarpine, 2-Methyl-6-(phenylethynyl)pyridine (MPEP), 5,7-dihydroxyflavone, vitamin B12, pipofezine, flurbiprofen axetil, 2-Amino-6-nitrobenzothiazole, nalachite green oxalate, enfenamic acid, fenaminosulf, AS-252424, phenserine, epalrestat, alizarin, dalcetrapib, SN-38, echinomycin, (S)-(+)-camptothecin, BI-2536, 10-hydroxycamptothecin, topotecan, delanzomib, volasertib, ispinesib, paclitaxel, FK-506, emetine, AVN-944, digoxin, vincristine, idarubicin, thapsigargin, lexibulin, ixazomib, cephalomannine, mitoxantrone, MLN-2238, demecolcine, vinorelbine, bardoxolone methyl, cycloheximide, actinomycin D, AZD-7762, PF-184, CHIR-124, cyanein, triptolide, KX-01, PF-477736, epirubicin, mycophenolate (mycophenolic acid), daunorubicin, PIK-75, vindesine, torin-2, floxuridine, Go-6976, OSU-03012, and a prodrug, metabolite, or derivative of any of the foregoing.

In alternative embodiments the following compound (or its isomer, or stereoisomer, or enantiomer, or deuterated version, or bioisostere) is used singly or in various combinations (for example, formulated with, or administered separately) with other drug such as anti-viral drugs before, during or after vaccination or administration of a causative agent of infection: (1R,2S,5S)-N-[(1S)-1-cyano-2-[(3S)-2-oxopyrrolidin-3-yl]ethyl]-3-[(2S)-3,3-dimethyl-2-(2,2,2-trifluoroacetamido)butanoyl]-6,6-dimethyl-3-azabicyclo[3.1.0]hexane-2-carboxamide administered orally or by inhalation (or nasally), for example, as liquid, solid, powder, mist or spray, which can target a protease (such as the 3CL protease in COVID-19) and optionally has the following structure and molecular weight:

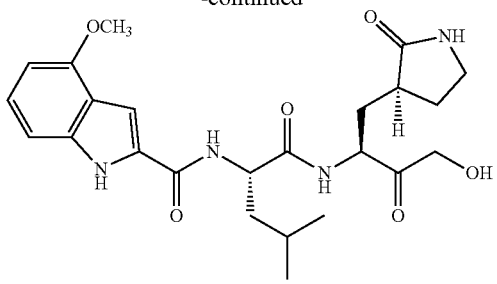

PF-07321332

C23H32F3N5O4 FW: 499.527

This protease inhibitor (PF-07321332, or PAXLOVID™) may be used alone before and after the vaccination and/or administration of the attenuated causative agent of infection, optionally administered with ritonavir (or NORVIR™) or lopinavir, or with any of the numerous antiviral agents as provided herein.

In alternative embodiments the following compounds (or their isomers, or stereoisomers, or enantiomer, or bioisostere) can be used singly or in various combinations:

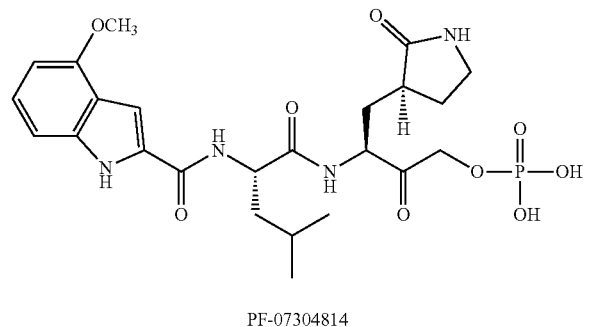

PF-07304814

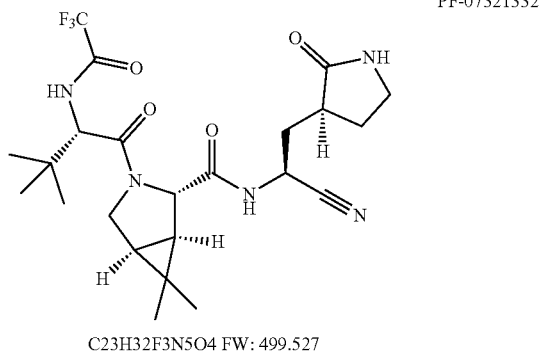

PF-00835231

These compounds (PF-07304814 and/or PF-00835231) (or its isomer, or stereoisomer, or enantiomer, or deuterated version, or bioisostere) may be used alone before and after the vaccination and/or administration of the attenuated causative agent of infection, optionally administered with ritonavir (or NORVIR™) or lopinavir, or with any of the numerous antiviral agents as provided herein.

In alternative embodiments, the PF-07321332 (or PAXLOVID™) and ritonavir (or NORVIR™) or lopinavir combination; or the PF-07304814 and/or PF-00835231 and ritonavir (or NORVIR™) or lopinavir combination; or the KALETRA™, ALTERA™, ALUVIA™, KALMELTREX, LOPIMUNE™ or LOPINAVIR™ and/or zanamivir (or RELENZA™) combination; is administered separately, or together (for example, formulated together) as a tablet, gel, geltab or capsule, as a powder, in a liquid, in a mist or a spray, or as a lozenge. In alternative embodiments, the PF-07321332 (or PAXLOVID™) and ritonavir (or NORVIR™) or lopinavir combination; or the PF-07304814 and/or PF-00835231 and ritonavir (or NORVIR™) or lopinavir combination; or the KALETRA™, ALTERA™, ALUVIA™, KALMELTREX, LOPIMUNE™ or LOPINAVIR™ and/or zanamivir (or RELENZA™) combination; is administered before, at the same time as, and/or after the vaccination.

In alternative embodiments, the PF-07321332 (or PAXLOVID™) and ritonavir (or NORVIR™) or lopinavir combination; or the PF-07304814 and/or PF-00835231 and ritonavir (or NORVIR™) or lopinavir combination; or the KALETRA™, ALTERA™, ALUVIA™, KALMELTREX, LOPIMUNE™ or LOPINAVIR™ and/or zanamivir (or RELENZA™) combination; is administered 1, 2, 3, 4, 5, 6, 7, 8, 9, 10, 11, 12, 13 or 14 or more days before, and/or on the day of, a first dose of the at least one of a plurality of dosages of the vaccine is administered, or a dose of the inactivated, attenuated, or the live, viable or infectious causative agent of the infection is administered.

In alternative embodiments, the PF-07321332 (or PAXLOVID™) and ritonavir (or NORVIR™) or lopinavir combination; or the PF-07304814 and/or PF-00835231 and ritonavir (or NORVIR™) or lopinavir combination; or the KALETRA™, ALTERA™, ALUVIA™, KALMELTREX, LOPIMUNE™ or LOPINAVIR™ and/or zanamivir (or RELENZA™) combination; is administered 1, 2, 3, 4, 5, 6, 7, 8, 9, 10, 11, 12, 13 or 14 or more days after a first dose of the at least one of a plurality of dosages of the vaccine is administered, or a dose of the inactivated, attenuated, or the live, viable or infectious causative agent of the infection is administered.

In alternative embodiments, the PF-07321332 (or PAXLOVID™) and ritonavir (or NORVIR™) or lopinavir combination; or the PF-07304814 and/or PF-00835231 and ritonavir (or NORVIR™) or lopinavir combination; or the KALETRA™, ALTERA™, ALUVIA™, KALMELTREX, LOPIMUNE™ or LOPINAVIR™ and/or zanamivir (or RELENZA™) combination; is administered both before and after a first dose of the at least one of a plurality of dosages of the vaccine is administered, or a dose of the inactivated, attenuated, or the live, viable or infectious causative agent of the infection is administered. Another agent which can be used singly or in combination before and accompanying vaccination is 2-deoxy-D-Glucose (2-DG).

In alternative embodiments, methods as provided herein comprise (or further comprise) administering in coordination with (optionally before, at the time of vaccination, and/or after vaccination of) an anti-microbial vaccine (or a dose of the inactivated, attenuated, or the live, viable or infectious causative agent of the infection) a therapeutic combination of drugs or a single drug, a pharmaceutical dosage form, a drug delivery device, or a product of manufacture, comprising:

- (a) a thiazolide class drug, optionally nitazoxanide (or ALINIA™, NIZONIDE™) or tizoxanide (or 2-Hydroxy-N-(5-nitro-2-thiazolyl)benzamide);
- (b) molnupiravir, optionally co-administered with and/or formulated with an avermectin class drug (optionally ivermectin), an antibiotic (optionally doxycycline or azithromycin) and/or zinc, or co-administered with and/or formulated with ivermectin, hydroxychloroquine, an antibiotic (optionally doxycycline or azithromycin) and/or zinc; (c) opaganib or YELIVA™, or opaganib or YELIVA™ and oral and/or inhaled or aerosol chloroquine (or ARALEN™), chloroquine phosphate, chloroquine diphosphate, amodiaquine (or AMDAQUINE™, AMOBIN™) and/or hydroxychloroquine (optionally, PLAQUENIL™), wherein optionally each or both of the opaganib and the chloroquine (or ARALEN™) chloroquine phosphate, chloroquine diphosphate and/or hydroxychloroquine (optionally, PLAQUENIL™) are in or formulated as a formulation for inhalation, for example, formulated as an aerosol, spray, mist, liquid or powder, or each or both are formulated for oral, intramuscular or intravenous administration,
- wherein optionally the opaganib is administered at a dosage of QD (once a day), bid (twice a day) or tid (three times a day) at a dosage of between about 100 to 600 mg per day or per dosage, or at about 100, 200, 300, 400, 500 or 600 mg per day or per dosage,
- and optionally the opaganib, or YELIVA™ is also administered or formulated with an antibiotic (optionally azithromycin or doxycycline), ivermectin (optionally at 12 mg ivermectin, optionally administered on days 1, 3, 6 and 8), hydroxychloroquine (optionally, PLAQUENIL™) and/or zinc (optionally zinc sulfate, optionally at (50 mg daily, or any zinc salt);
- (d) lopinavir, ritonavir (or NORVIR™) and oseltamivir (optionally, TAMIFLU™), and/or zanamivir (or RELENZA™);
- (e) lopinavir combined (formulated) with ritonavir (or NORVIR™), or KALETRA™, ALTERA™, ALUVIA™, KALMELTREX, LOPIMUNE™ or LOPINAVIR™, and/or zanamivir (or RELENZA™), or lopinavir and ritonavir separately formulated;
- (f) lopinavir combined (formulated) with ritonavir (or NORVIR™) (or KALETRA™, ALTERA™, ALUVIA™, KALMELTREX, LOPIMUNE™ or LOPINAVIR™), or lopinavir and ritonavir (or NORVIR™), and oseltamivir (optionally, TAMIFLU™), and/or zanamivir (or RELENZA™), optionally also with inhaled or aerosol formulations or versions of chloroquine (or ARALEN™) amodiaquine (or AMDAQUINE™, AMOBIN™), chloroquine phosphate, chloroquine diphosphate and/or hydroxychloroquine (optionally, PLAQUENIL™) and/or oral chloroquine (or ARALEN™), chloroquine phosphate, chloroquine diphosphate and/or hydroxychloroquine (optionally, PLAQUENIL™) simultaneously;
- (g) lopinavir, ritonavir (or NORVIR™), amodiaquine (or AMDAQUINE™, AMOBIN™), chloroquine and oseltamivir (or TAMIFLU™); wherein optionally the chloroquine comprises inhaled or aerosol chloroquine (or ARALEN™), chloroquine phosphate, chloroquine diphosphate and/or hydroxychloroquine (optionally, PLAQUENIL™) and/or oral chloroquine (or ARALEN™), chloroquine phosphate, chloroquine diphosphate and/or hydroxychloroquine (optionally, PLAQUENIL™) simultaneously;
- (H) lopinavir and oseltamivir (optionally, TAMIFLU™), and/or zanamivir (or RELENZA™);
- (i) ritonavir (or NORVIR™) and oseltamivir (optionally, TAMIFLU™), and/or zanamivir (or RELENZA™);
- (j) remdesivir (optionally, GS-5734™, Gilead Sciences) alone, or oseltamivir (optionally, TAMIFLU™) and remdesivir (optionally, GS-5734™, Gilead Sciences), and optionally the remdesivir is an oral formulation and/or an inhaled or aerosol remdesivir formulation;
- (k) oseltamivir (optionally, TAMIFLU™) and efavirenz (optionally, SUSTIVA™), and/or zanamivir (or RELENZA™);
- (l) oseltamivir (optionally, TAMIFLU™) and nevirapine (or the combination efavirenz with emtricitabine and tenofovir, or ATRIPLA™);
- (m) oseltamivir (or TAMIFLU™) and amprenavir (optionally, AGENERASE™);
- (n) oseltamivir (optionally, TAMIFLU™) and nelfinavir (optionally, VIRACEPT™);
- (o) a thiazolide class drug, optionally nitazoxanide (optionally ALINIA™ NIZONIDE™) or tizoxanide (or 2-Hydroxy-N-(5-nitro-2-thiazolyl)benzamide), with or in combination with any of (a) to (nn), or any drug or drug combination as provided herein, optionally a thiazolide class drug, optionally nitazoxanide, with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin; or a thiazolide class drug (optionally, nitazoxanide or tizoxanide) and oseltamivir (or TAMIFLU™),
- and optionally the thiazolide class drug (optionally, nitazoxanide or tizoxanide) is formulated or administered with ribavirin or tribavirin (or COPEGUS™, REBETOL™, or VIRAZOLE™), and an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin;
- (p) plitidepsin (also known as dehydrodidemnin B), or APLIDIN™ (PharmaMar, S. A.);

(q) an inhibitor or S-phase kinase-associated protein 2 (SKP2), or dioscin, or niclosamide, or NICLOCIDE™, FENASAL™, or PHENASAL™

(r) ritonavir (or NORVIR™), ribavirin or tribavirin (or COPEGUS™ REBETOL™, or VIRAZOLE™), interferon beta 1 b, or a combination of ribavirin and interferon beta, or a combination of lopinavir and ritonavir (or NORVIR™) and interferon-beta-1b;

(s) a nucleoside analog reverse-transcriptase inhibitor (NRTI) (optionally abacavir, or ZIAGEN™), acyclovir or aciclovir (optionally ZOVIRAX™), adefovir (optionally HEPSERA™), amantadine(optionally GOCOVRI™, SYMADINE™, SYMMETREL™), rintatolimod (or AMPLIGEN™), amprenavir (optionally, AGENERASE™), aprepitant (or EMEND™), umifenovir (or ARBIDOL™) atazanavir (or REYATAZ™), atazanavir (or REYATAZ™), tenofovir, a combination of efavirenz and emtricitabine and tenofovir (or ATRIPLA™), balavir, baloxavir marboxil (XOFLUZA™), bepotastine, bevirimat, bictegravir, a combination of bictegravir and emtricitabine and tenofovir alafenamide (or BIKTARVY™), brilacidin, bivalirudin (or BIVALITROBAN™), cidofovir, caspofungin, lamivudine and zidovudine (optionally, COMBVIR™), cobicstat, colisitin, cocaine, darunavir, delavirdine, descovy, didanosine, docosanol, dolutegravir, ecoliever, edoxudine, efavirenz (optionally, SUSTIVA™), elvitegravir, emtricitabine, enfuvirtide, foscarnet, fosfonet, galidesivir, ibacitabine, icatibant, idoxuridine, ifenprodil, imiquimod, imunovir, indinavir, inosine, an interferon (optionally interferon type I, interferon type II and/or interferon type III), lamivudine (or EPIVIR™, ZEFFIX™) lopinavir, loviride, ledipasvir, leronlimab, maraviroc, methisazone, moroxydine, nelfinavir, nevirapine, nexavir, nitazoxanide (optionally ALINIA™, NIZONIDE™), norvir, a nucleoside analogue or derivative (optionally brincidofovir (or TEMBEXA™), didanosine (or VIDEX™), favipiravir (also known as T-705 or AVIGAN™, or favilavir, Toyama Chemical, Fujifilm, Japan, or FABIFLU™ Glenmark Pharmaceuticals), vidarabine, galidesivir (optionally, BCX4430, IMMUCILLIN-A™), remdesivir (optionally, GS-5734™, Gilead Sciences), cytarabine, gemcitabine, emtricitabine, lamivudine, zalcitabine, entecavir, stavudine, telbivudine, zidovudine, idoxuridine and/or trifluridine or any combination thereof), oseltamivir (or TAMIFLU™), peginterferon alfa-2a, penciclovir, peramivir (optionally, RAPIVAB™), perfenazine, pleconaril, plurifloxacin, podophyllotoxin, pyramidine, raltegravir, rifampicin, ribavirin or tribavirin (or COPEGUS™, REBETOL™, or VIRAZOLE™), rilpivirine, rimantadine, ritonavir (or NORVIR™) saquinavir, sofosbuvir, stavudine, telaprevir, tegobuv, tenofovir alafenamide, tenofovir disoproxil, tenofovir, tipranavir, trifluridine, trizivir, tromantadinc, truvada, valaciclovir (optionally, VALTREX™), valganciclovir, valrubicin, vapreotide, vicriviroc, vidarabine, viramidine, velpatasvir, vivecon, zalcitabine, zanamivir (optionally, RELENZA™), zidovudine, an immunosuppressive drug (optionally tocilizumab or atlizumab, or ACTEMRA™, or ROACTEMRA™) or any combination thereof;

(t) a mucolytic therapy or drug, optionally acetylcysteine, ambroxol, bromhexine (or BISOLVON™), carbocisteine, erdosteine, mecysteine or dornase alfa, or an expectorant, optionally guaifenesin;

(u) a viral, or a coronavirus or a COVID-19, protease inhibitor, optionally ASC09 (CAS registry no. 1000287-05-7) (Janssen Research and Development, LLC), ritonavir (or NORVIR™) or ASC09 and ritonavir (or NORVIR™), or a JAK1/2 inhibitor (optionally baricitinib), optionally compound 11r (University of Lubeck, Germany, see optionally, Zhang et al J. Med Chem 2020, Feb. 11, 2020), or darunavir, cobicistat or darunavir and cobicistat;

(v) an angiotensin-converting enzyme 2 (ACE2) inhibitor, optionally to block the site of viral spike protein interaction for anti-SARS-CoV-2 infection control;

(w) an anti-vascular endothelial growth factor (VEGF) (optionally VEGF-A) drug or antibody, optionally bevacizumab;

(x) a protease inhibitor, optionally danoprevir, optionally a serine protease inhibitor, optionally camostat or narlaprevir (optionally ARLANSA™);

(y) anti-PD-1 checkpoint inhibitor, optionally camrelizumab;

(z) a compound or antibody capable of binding complement factor C5 and blocking membrane attack complex formation, optionally eculizumab;

(aa) a cathepsin inhibitor, optionally a cathepsin K, B or L inhibitor, optionally relacatib;

(bb) thalidomide, or thalidomide and glucocorticoid (optionally ciclesonide (or ALVESCO™, OMNARIS™, OMNIAIR™, ZETONNA™ or ALVESCO™)) (optionally low-dose glucocorticoid), or and thalidomide and celecoxib;

(cc) an antibacterial antibiotic or a macrolide drug, wherein optionally the macrolide drug comprises azithromycin, optionally dosaged at between about 50 mg to about 2000 mg per dose or per day (optionally, ZITHROMAX™, or AZITHROCIN™, optionally an oral extended- or delayed-release formulation of azithromycin, or ZMAX™), clarithromycin (optionally, BIAXIN™), erythromycin (optionally, ERYTHROCIN™), or fidaxomicin (optionally, DIFICID™ or DIFICLIR™), troleandomycin (optionally, TEKMISIN™), tylosin (optionally, TYLOCINE™ or TYLAN™), solithromycin (optionally, SOLITHERA™), oleandomycin (or SIGMAMYCINE™), midecamycin, roxithromycin, kitasamycin or turimycin, josamycin, carbomycin or magnamycin, and/or spiramycin, and optionally the antibacterial antibiotic comprises a tetracycline class drug, a glycylcycline or a fluorocycline class drug, or an analogue thereof, and optionally the tetracycline, glycylcycline or fluorocycline drug or analogue thereof comprises or is: tetracycline or SUMYCIN™; chlortetracycline or AUREOMYCIN™; oxytetracycline; demeclocycline or DECLOMYCIN™, DECLOSTATIN™, LEDERMYCIN™, BIOTERCICLIN™, DEGANOL™, DETECLO™, DETRAVIS™, MECICLIN™, MEXOCINE™, CLORTETRIN™; lymecycline; meclocycline; metacycline; minocycline or MINOCIN™; rolitetracycline; doxycycline, or DORYX™, DOXYHEXA™, DOXYLIN™; tigecycline or TYGACIL™; eravacycline or XERAVA™; sarecycline or SEYSARA™; omadacycline or NUZYRA™; or any combination thereof, and optionally the antibacterial antibiotic or macrolide drug, optionally azithromycin (or ZMAX™), is administered in combination with, and/or is combined with, chloroquine (or ARALEN™), amodiaquine (or AMDAQUINE™, AMOBIN™), chloroquine phosphate, chloroquine diphosphate and/or hydroxychloroquine (optionally, PLAQUENIL™), and the combination is administered commencing on the first, second, third, fourth, fifth, sixth, seventh, eighth, ninth and/or tenth day of therapy, or is administered for 1, 2, 3, 4, 5, 6, 7, 8, 9, 10 or up to 20 or more days, or for between about 1 to 21 days or longer, or is administered until within 1, 2, 3, 4, 5, 6, 7, 8, 9, 10 or up to 20 or more days of ending the therapy for treating, preventing, ameliorating, slowing the progress of, decreasing the severity of or preventing the coronavirus infection, and optionally the chloroquine (or ARALEN™), chloroquine phosphate, amodiaquine (or AMDAQUINE™, AMOBIN™), chloroquine diphosphate and/or hydroxychloroquine (optionally, PLAQUENIL™) is administered the entire length of the treatment but the azithromycin, optionally dosaged at between about 50 mg to about 2000 mg per dose or per day (optionally, ZITHROMAX™, or AZITHROCIN™, optionally an oral extended-release formulation of azithromycin, or ZMAX™) administration is halted or ceased after two, three, four, five or six days after treatment is commenced, and optionally the azithromycin administration is replaced by a tetracycline class drug, and optionally the tetracycline class drug comprises doxycycline, or DORYX™, DOXYHEXA™, DOXYLIN™ administration, and optionally the antibacterial antibiotic, optionally azithromycin (optionally, ZITHROMAX™, or AZITHROCIN™, optionally dosaged at between about 50 mg to about 2000 mg per dose or per day, and optionally an oral extended-release formulation of azithromycin, or ZMAX™), is administered or formulated with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and/or cholecalciferol (vitamin D3) or calcifediol, and optionally the antibacterial antibiotic comprises an antimycobacterial drug, and optionally the antimycobacterial drug comprises clofazimine (optionally LAMPRENE™);

(dd) an avermectin class drug such as ivermectin (optionally STROMECTOL™, SOOLANTRA™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, optionally dosaged and/or administered at about 5 microgram/kg to about 1 gram (g) per day, optionally formulated or administered at about 1 to 10, 12, 15, 20, 30, 40, 50, 60, 70, 80, 100, 120, 140, 160, 180, 200, 220 or 240 mg per day, or between about 1 to 240 mg per day, or between about 3 to 240 mg per day, optionally formulated or administered with an antibiotic (optionally azithromycin, minocycline, amoxicillin, niclosamide, nitazoxanide, hydroxychloroquine or doxycycline, and optionally the doxycycline is at between about 25 to 600 mg per dose or per day, or at about 100 mg per dose or per day, and optionally the azithromycin is at between about 50 mg to 2000 mg per dose or per day), optionally as a single or a divided dose, and optionally formulated and administered as an inhalant or a mist (optionally using a nebulizer, nasal spray or equivalent), optionally formulated as an aerosol, spray, mist, liquid or powder, optionally formulated as an aerosol, spray, mist, liquid or powder, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is formulated with and/or administered with chloroquine (or ARALEN™), chloroquine phosphate, chloroquine diphosphate and/or hydroxychloroquine (optionally, PLAQUENIL™) with or without zinc (optionally a zinc sulphate, acetate, gluconate or picolinate or any zinc salt), and optionally this combination is administered weekly, or every two week, or one every 5 to 28 days, as a prophylactic, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered alone in the morning (AM), and an antibiotic (optionally doxycycline) and/or a chloroquine (optionally, ARALEN™), chloroquine phosphate, chloroquine diphosphate and/or hydroxychloroquine (optionally, PLAQUENIL™) is administered in the afternoon and/or evening, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered alone for 1, 2, 3, 4, 5, 6, 7, 8, 9, 10 or up to 20 or more days, followed by administration of an antibiotic (optionally doxycycline) for a corresponding period of days, and optionally repeating the cycle of dosaging, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is formulated or administered with:

(i) at least one antibiotic (wherein optionally the antibiotic is doxycycline(optionally, DORYX™, DOXYHEXA™, DOXYLIN™) (optionally formulated or administered at a dosage of between about 25 mg to 600 mg per dose or per day), or azithromycin (optionally, ZITHROMAX™, or AZITHROCIN™, optionally dosaged at between about 50 mg to about 2000 mg per dose or per day, optionally an oral extended-release formulation of azithromycin, or ZMAX™) (optionally formulated or administered at a dosage of between an about 50 mg to 2000 mg);

(ii) chloroquine (or ARALEN™), chloroquine phosphate, chloroquine diphosphate and/or hydroxychloroquine (optionally, PLAQUENIL™) (optionally formulated or administered at a dosage of between an about 10 mg to 2000 mg per day);

(iii) a zinc (optionally a zinc sulphate, acetate, gluconate or picolinate or any zinc salt) optionally formulated or administered at a dosage of between about 1 mg to 250 mg; and/or (iv) at least one vitamin, and optionally the at least one vitamin comprises: vitamin C optionally formulated or administered at a dosage of between about 500 to 5000 units (U) per dose, and/or Vitamin D (or cholecalciferol) optionally formulated or administered at a dosage of between about 3,000 to 100,000 units per day, or between about 10,000 to 50,000 units a day, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered or formulated alone or in combination with any of the above (i) to (iv) (for example, at least one antibiotic, chloroquine (or ARALEN™) chloroquine phosphate, chloroquine diphosphate and/or hydroxychloroquine (optionally, PLAQUENIL™), zinc or any zinc salt and/or at least one vitamin are formulated (and administered) as oral formulations (for example, as tablets, capsules, gels or geltabs), injectable formulations, powders (for example, for inhalation or for addition to an ingestible liquid) or liquids (for example, for ingestion, infusion or injection);

(ee) chloroquine (or ARALEN™), chloroquine phosphate, chloroquine diphosphate and/or hydroxychloroquine (optionally, PLAQUENIL™) alone or with (or formulated with) or in combination with any of (a) to (bb), or chloroquine, chloroquine phosphate, chloroquine diphosphate and/or hydroxychloroquine (optionally, PLAQUENIL™) and oseltamivir (or TAMIFLU™);

(ff) chloroquine (optionally, ARALEN™), chloroquine phosphate, alone or with:

(i) an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, optionally at a dosage of between about 3 to 340 mg per day, or about 6 mg to 60 mg, or about 10 mg to 80 mg dosages, or about 12 to 50 mg dosages;

(ii) vitamin D, vitamin D2 (or ergocalciferol), vitamin D3 (or cholecalciferol) optionally at a dosage of between about 3,000 to 100,000 units per day, or between about 10,000 to 50,000 units a day, and/or (iii) with (i) and (ii) and zinc (optionally a zinc sulphate, acetate, gluconate or picolinate or any zinc salt) optionally at a dosage of between about 1 mg to 250 mg, or (iv) the combination of (iii) also with a tetracycline class drug, wherein optionally the tetracycline class drug comprises doxycycline, or DORYX™, DOXYHEXA™, DOXYLIN™, optionally dosages at between about 25 mg to 600 mg per day or per dose, optionally between about 100 mg to 500 mg, or a between about 200 mg to 400 mg per dose or per day;

(gg) colchicine, or COLCRYS™, MITIGARE™, optionally administered or dosaged at between about 0.5 mg to 20 mg, or about 1 mg to 15 mg, or about 3 mg to 10 mg, or about 4 mg to 6 mg, per day for a period of between about 7 and 21 days, or about 14 days, and optionally also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily);

(hh) a corticosteroid or glucocorticoid class drug such as ciclesonide (or ALVESCO™, OMNARIS™, OMNIAIR™, ZETONNA™ or ALVESCO™), budesonide (optionally RHINOCORT™ or PULMICORT™), prednisolone (or ORAPRED™), methylprednisolone, prednisone (or DELTASONE™ or ORASONE™) or hydrocortisone (or CORTEF™), wherein optionally the corticosteroid or glucocorticoid class drug (optionally ciclesonide) is inhaled, or a selective estrogen receptor modulator (SERM), or toremifene (or FARESTON™), or clomifene or clomiphene (or CLOMID™, SEROPHENE™) wherein optionally the SERM is inhaled;

and optionally the corticosteroid class drug (for example budesonide) is administered by inhalation, for example, in a nebulized form, for example, between about 1 mg to 12 mg per day of budesonide is administered by inhalation, or between about 6 to 80 mg per day of prednisolone is administered orally, or between about 6 to 100 mg per day of prednisone is administered orally, or between about 30 to 400 mg per day of hydrocortisone is administered orally, and optionally the corticosteroid class drug is formulated as a powder or for administration in an inhaler or by nasal spray, or for rectal administration, and optionally the corticosteroid class drug (for example, budesonide) is administered together with or in combination with 10 mg to 80 mg, an antibiotic (optionally azithromycin or a tetracycline class drug, wherein optionally the tetracycline class drug comprises doxycycline, or DORYX™, DOXYHEXA™, DOXYLIN™), zinc or any zinc salt and/or a vitamin (optionally vitamin D or calcifediol, D2 (or ergocalciferol), D3 (or cholecalciferol), C, E, B12, B6);

(ii) an anti-androgen drug, and optionally the anti-androgen drug is bicalutamide, optionally CASODEX™, or dutasteride (or AVODART™), and optionally the anti-androgen drug is a nonsteroidal anti-androgen (NSAA) or an androgen receptor (AR) antagonist, and optionally the NSAA or AR antagonist comprises proxalutamide (or its developmental name GT-0918) (Suzhou Kintor Pharmaceuticals, Inc., a subsidiary of Kintor Pharmaceutical Limited), or flutamide (or niftolide, or EULEXIN™), or bicalutamide (or CASODEX™) or enzalutamide (or XTANDI™), and optionally the anti-androgen drug comprises a 5α-reductase inhibitor, and optionally the 5α-reductase inhibitor comprises finasteride (or PROSCAR™, PROPECIA™, or FINIDE™)

and optionally the anti-androgen drug, or NSAA, or proxalutamide or bicalutamide, is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, eprinomectin or abamectin;

and optionally the anti-androgen drug, or NSAA, or bicalutamide, proxalutamide, flutamide or niftolide, bicalutamide, enzalutamide or dutasteride, is administered at dosages of about 50 to 100 mg optionally administered once, twice (BID), three times (TID) or four times a day, or is administered at dosages of about 50 to 100 mg per day, and optionally the anti-androgen drug, or NSAA, or bicalutamide, proxalutamide, flutamide or niftolide, bicalutamide, enzalutamide or dutasteride, is administered with an avermectin class drug, or ivermectin, optionally also administered with hydroxychloroquine, zinc and/or a vitamin (optionally vitamin D (optionally vitamin D2, or ergocalciferol, or Vitamin D3 or cholecalciferol, optionally administered at about 1000 to 4000 ugm/day) or vitamin C, B or A;

and optionally bicalutamide is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and optionally bicalutamide is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin;

(jj) a hydrocortisone or cortisol (optionally CORTEF™, SOLUCORTEF™), optionally hydrocortisone sodium succinate or hydrocortisone acetate or dexamethasome (optionally DEXTENZA™, OZURDEX™, NEOFORDEX™);

(kk) an alpha-ketoamide (α-ketoamide), wherein optionally the alpha-ketoamide is a structure as described by Zhang et al, J. Med. Chem. 2020, 63, 9, 4562-4578, or Meng et al Chem. Sci. (2019) vol. 10, pg 5156 (optionally the structure KAM-2), and optionally the alpha-ketoamide is formulated or administered as an inhalant or a powder or mist, and optionally formulated or administered with (optionally as an inhalant): an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin; an antibiotic (optionally azithromycin or a tetracycline class drug, wherein optionally the tetracycline class drug comprises doxycycline, or DORYX™, DOXYHEXA™, DOXYLIN™); chloroquine (or ARALEN™), chloroquine phosphate, chloroquine diphosphate and/or hydroxychloroquine (optionally, PLAQUENIL™); zinc or any zinc salt; remdesivir (optionally, GS-5734™, Gilead Sciences); oseltamivir (or TAMIFLU™); and/or, hydrocortisone; or, any combination thereof;

(ll) a compound, drug or formulation that decreases stomach acid production or decreases stomach pH, wherein optionally the compound, drug or formulation comprises famotidine, or PEPCID™, and optionally the famotidine is administered at a dosage of between about 10 to 60 mg per day, or between about 20 to 40 mg per day, and optionally the famotidine is administered is administered with: an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and/or a tetracycline tetracycline class drug, and optionally the tetracycline class drug comprises doxycycline, or DORYX™, DOXYHEXA™, DOXYLIN™;

(mm) a dendrimer, optionally astodrimer sodium (Starpharma, Melbourne, Australia);

(nn) an antihistamine class drug such as azelastine, or ASTELIN™, OPTIVAR™, ALLERGODIL™, brompheniramine, fexofenadine or ALLEGRA™ pheniramine or AVIL™, or chlorpheniramine;

(oo) a selective serotonin reuptake inhibitor (SSRI) class drug, optionally fluvoxamine, or LUVOX™, FAVERIN™, FLUVOXIN™;

(pp) a nicotinic antagonist, a dopamine agonist or a noncompetitive N-Methyl-d-aspartic acid or N-Methyl-d-aspartate (NMDA) antagonist, wherein optionally the nicotinic antagonist, dopamine agonist or noncompetitive NMDA antagonist is 1-adamantylamine or amantadine, or GOCOVRI™, SYMADINE™, SYMMETREL™, optionally administered or dosaged at between about 50 mg to 150 mg, or about 100 mg, per day for a period of between about 7 and 21 days, or about 14 days, and optionally the nicotinic antagonist, dopamine agonist or noncompetitive NMDA antagonist is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally the amantadine is formulated or administered at 100 mg per day for the first two days of treatment, which optionally can then be elevated to 100 mg twice daily, optionally for the next 10 days;

(qq) an immunosuppressive drug, wherein optionally the immunosuppressive drug comprises tocilizumab or atlizumab, or ACTEMRA™, or ROACTEMRA™, or a calcineurin inhibitor (CNI), wherein the CNI comprises ciclosporin (or cyclosporine or cyclosporin), or NEORAL™, or SANDIMMUNE™, or tacrolimus, or PROTOPIC™, or PROGRAF™, and optionally the immunosuppressive drug is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally the calcineurin inhibitor (CNI), wherein the CNI comprises ciclosporin (or cyclosporine or cyclosporin) is formulated combination of CNI (optionally cyclosporine) at a dose of 3 mg/kg (180 mg daily) together with 12 mg ivermectin once, and optionally also plus zinc 50 mg base and doxycycline 100 mg bid, optionally all for 10 days;

(rr) a protein kinase inhibitor, wherein optionally the protein kinase inhibitor is a p38 mitogen-activated protein kinase inhibitor, or ralimetinib, and optionally the protein kinase inhibitor is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily);

(ss) an anti-inflammatory therapy or at least one anti-inflammatory therapy drug, wherein optionally the anti-inflammatory therapy or drug comprises: a sphingosine kinase-2 (SK2) selective inhibitor (optionally, opaganib (optionally, YELIVA™), sirolimus, a JAK1/2/TYK2 inhibitor (optionally ruxolitinib), an anti-CD47 mAb (optionally meplazumab), a cyclooxygenase (COX) (optionally, COX2) inhibitor, a glucocorticoid (optionally a synthetic glucocorticoid, hydrocortisone, dexamethasone (or DEXTENZA™, OZURDEX™, or NEOFORDEX™) or cortisol, or CORTEF™), plitidepsin or dehydrodidemnin B, or APLIDIN™, or a nonsteroidal anti-inflammatory drug (NSAID), wherein optionally the NSAID comprises indomethacin (or indomethacin) or INDOCID™ or INDOCIN™, or naproxen, or NAPROSYN™ or ALEVE™, or a cyclooxygenase inhibitor, or a COX-1 or an COX-2 inhibitor, or aspirin, or ibuprofen or ADVIL™, MOTRIN™ or NUROFEN™, or celecoxib or CELEBREX™, or parecoxib or DYNASTAT™, or etoricoxib or ARCOXIA™, and optionally the anti-inflammatory therapy or anti-inflammatory therapy drug is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally opaganib, or YELIVA™, or opaganib, or YELIVA™ administered or formulated together with an oral and/or inhaled or aerosol chloroquine (or ARALEN™), chloroquine phosphate, chloroquine diphosphate and/or hydroxychloroquine (optionally, PLAQUENIL™), and optionally the opaganib or YELIVA™ is formulated or administered at a dosage of QD (once a day), bid (twice a day) or tid (three times a day) at a dosage of between about 100 to 600 mg per day or per dosage, or at about 100, 200, 300, 400, 500 or 600 mg per day or per dosage, and optionally the opaganib, or YELIVA™ is also administered or formulated with an antibiotic (optionally azithromycin or doxycycline), ivermectin (optionally at 12 mg ivermectin, optionally administered on days 1, 3, 6 and 8), hydroxychloroquine (optionally, PLAQUENIL™) and/or zinc or any zinc salt (optionally zinc sulfate, optionally at (50 mg daily);

(tt) a calcium channel blocker, or verapamil (or ISOPTIN™, CALAN™), or a voltage gated potassium (KCNH2) channel or a voltage gated calcium channel (CACNA2D2) blocker, or amiodarone (or CORDARONE™, NEXTERONE™);

(uu) suramin, or ANTRYPOL™, BAYER 305™, or GERMANIN™;

(vv) a peroxisome proliferator-activated receptor (PPAR) agonist, wherein optionally the PPAR agonist comprises fenofibrate, or TRICOR™, FENOBRAT™, FENOGLIDE™, or LIPOFEN™, or a combination of fenofibrate and simvastatin, or CHOLIB™, optionally the PPAR agonist comprises a combination of fenofibrate and pravastatin, or PRAVAFENIX™, or the PPAR agonist comprises bezafibrate, or BEZALIP™, or combination of bezafibrate and chenodeoxycholic acid, or HEPACONDA™, or aluminium clofibrate, or alfibrate, or ciprofibrate, or clinofibrate or LIPOCLIN™, or clofibrate or ATROMID-S™, or clofibride, or gemfibrozil or LOPID™, or ronifibrate, or simfibrate or CHOLESOLVIN™, or any combination thereof, (ww) a synthetic nucleoside analog or derivative, or N4-hydroxycytidine, or a prodrug of N4-hydroxycytidine, optionally molnuvpiravir (Merck), or favipiravir (also known as T-705 or AVIGAN™, or favilavir, Toyama Chemical, Fujifilm, Japan, or FABIFLU™, Glenmark Pharmaceuticals), wherein the synthetic nucleoside analog or derivative, or N4-hydroxycytidine, or the prodrug of N4-hydroxycytidine, optionally molnuvpiravir or favipiravir, is given as between about 10 mg to 3 gm per dose, or between about 10 mg to 3 gm per day, or can be dosed either as a single dose or given one, two, three or four times a day, or is administered at 200 to 800 mg twice daily, or 200, 400, 600 or 800 mg twice daily, or at 200 to 800 mg three times a day, or at 200, 400, 600 or 800 mg three times a day, or is administered at 200 to 800 mg three times a day for between about 2 to 15 days, or for about 2, 3, 4, 5, 6, 7, 8, 9, 10, 11 or 12 days, and optionally when combined with other drugs a lower dosage is used, optionally administered at 100 or 200 mg three times a day for between about 5 to 15 days, or for about 7, 8, 9, 10, 11 or 12 days, and optionally the synthetic nucleoside analog or derivative, or N4-hydroxycytidine, or the prodrug of N4-hydroxycytidine, optionally molnuvpiravir or favipiravir, is administered with an avermectin class drug (optionally ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin), and optionally the synthetic nucleoside analog or derivative, or N4-hydroxycytidine, or the prodrug of N4-hydroxycytidine, optionally molnuvpiravir or favipiravir, is administered with an avermectin class drug (optionally ivermectin) with an antibiotic, and optionally the antibiotic comprises azithromycin, minocycline, amoxicillin, niclosamide, nitazoxanide, hydroxychloroquine or doxycycline), and optionally the synthetic nucleoside analog or derivative, avermectin class drug, and antibiotic are administered together or as separate formulations, and optionally are administered every one, two, three, four or five weeks for between about one month and one year or more;

and optionally molnuvpiravir, ivermectin and hydroxychloroquine are administered together or as separate formulations, and optionally are administered every one, two, three, four or five weeks for between about one month and one year or more;

and optionally the synthetic nucleoside analog or derivative (optionally N4-hydroxycytidine, or the prodrug of N4-hydroxycytidine, optionally molnuvpiravir or favipiravir), and antibiotic (optionally doxycycline or hydroxychloroquine) is administered with zinc (optionally a zinc sulphate, acetate, gluconate or picolinate, or zinc oxide nanoparticles, optionally at a dosage of between about 1 mg to 250 mg, or about 50 mg per day) and/or a vitamin, optionally vitamin C or D), and optionally the synthetic nucleoside analog or derivative, or N4-hydroxycytidine, or the prodrug of N4-hydroxycytidine, optionally molnuvpiravir or favipiravir, is administered with an antibiotic (optionally the antibiotic comprises azithromycin, minocycline, amoxicillin, niclosamide, nitazoxanide, hydroxychloroquine or doxycycline), optionally also administered with zinc (optionally a zinc sulphate, acetate, gluconate or picolinate, or zinc oxide nanoparticles, optionally at a dosage of between about 1 mg to 250 mg, or about 50 mg per day) and/or a vitamin, optionally vitamin C or D, and optionally the anti-androgen drug, or NSAA, or bicalutamide, proxalutamide, flutamide or niftolide, bicalutamide, enzalutamide or dutasteride, is administered with colchicine (or COLCRYS™, MITIGARE™), and optionally also zinc and/or a vitamin (optionally vitamin D (optionally vitamin D2, or ergocalciferol, or Vitamin D3 or cholecalciferol, optionally administered at about 1000 to 4000 ugm/day), or vitamin C, B or A), and optionally the anti-androgen drug, or NSAA, or bicalutamide, proxalutamide, flutamide or niftolide, bicalutamide, enzalutamide or dutasteride, is administered with an antibiotic (optionally azithromycin or doxycycline), and optionally also zinc and/or a vitamin (optionally vitamin D (optionally vitamin D2, or ergocalciferol, or Vitamin D3 or cholecalciferol, optionally administered at about 1000 to 4000 ugm/day), or vitamin C, B or A), and optionally also with hydroxychloroquine;

(xx) an anti-malarial drug, wherein optionally the anti-malarial drug comprises mefloquine (or LARIAM™, MEPHAQUIN™, or MEFLIAM™);

(yy) an antisera or an antibody or antibody or vaccine therapy for treating, preventing or ameliorating a microbial or a viral infection (optionally a coronavirus infection, optionally a COVID-19 infection) or a microbial infection (optionally a protozoan, helminthiasis, insect and/or parasitic infection), and optionally the antibody comprises a monoclonal antibody, and optionally the monoclonal antibody comprises sotrovimab (GlaxoSmithKline and Vir Biotechnology), or casirivimab, imdevimab or casirivimab and imdevimab (REGEN-COV™) (Regeneron), or bamlanivimab oretesevimab or bamlanivimab and etesevimab (Junshi Biosciences), or tocilizumab or ACTEMRA™ or ROACTEMRA™ (Hoffmann-La Roche), and optionally the vaccine comprises tozinamera or COMIRNATY™ (Pfizer), or elasomeran or SPIKEVAX™ (Moderna), or SPUTNIK V™ or Gam-COVID-Vac (Gamaleya Research Institute), or AZD1222 or COVISHIELD™ or VAXZEVRIA™ (Oxford-AstraZeneca), and optionally the antibody or antibody therapy comprises or is contained in a convalescent sera or plasma, and/or (zz) any combination of (a) to (yy), and optionally any of these combinations is administered very 2, 3, 4, 5, 6, 7, 8, 9 or 10 or more days for between about 1 month and one year or more, and optionally any one or several or all of (a) to (zz) with an (or formulated with or formulated as an) inhaled or aerosol formulation such as a powder, spray or a mist or aerosol, and/or formulated with or formulated as an oral, intramuscular (IM) or intravenous (IV) formulation, wherein optionally both the inhaled (or aerosol) and the oral, IV and/or IM formulations are administered simultaneously or sequentially, and optionally the inhaled or aerosol formulation comprises chloroquine (or ARALEN™), chloroquine phosphate, chloroquine diphosphate and/or hydroxychloroquine (optionally, PLAQUENIL™) and/or oral chloroquine (or ARALEN™), chloroquine phosphate, chloroquine diphosphate and/or hydroxychloroquine (optionally, PLAQUENIL™) administered simultaneously or overlapping, and optionally the inhaled or aerosol formulation comprises an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and optionally any one or several or all of (a) to (zz), or any therapeutic combination of drugs or a drug, or a pharmaceutical dosage form as provided herein, are administered orally, intramuscularly, subcutaneously, topically, by use of an enema, intravaginally, or intravenously, or administration is by subcutaneous administration, sublingual administration, inhalation or by aerosol (optionally by inhalation of a liquid, an aerosol, a spray, a mist or a powder), by absorbable patch, by use of an implant, or by use of an enema or a suppository.

In alternative embodiments, the anti-viral drug or medication, or anti-microbial drug, is or comprises: molnupiravir, efavirenz (optionally, SUSTIVA™), tenofovir, emtricitabine and tenofovir, nevirapine (or the combination efavirenz with emtricitabine and tenofovir, or ATRIPLA™), amprenavir (optionally, AGENERASE™), nelfinavir (optionally, VIRACEPT™) and/or remdesivir (optionally, GS-5734™, Gilead Sciences), a viral RNA-dependent RNA polymerase inhibitor, optionally galidesivir, a nucleoside analog reverse-transcriptase inhibitor (NRTI) (optionally abacavir, or ZIAGEN™), and optionally the anti-viral drug or medication is or comprises an anti-retroviral drug or drug combination, and optionally the anti-retroviral drug or drug combination comprises: darunavir and cobicistat (optionally, REZOLSTA™ or PREZCOBIX™); atazanavir and cobicistat (or EVOTAZ™); abacavir, lamivudine and dolutegravir (TRIUMEQ™); tenofovir (or disoproxil or emtricitabine) and elvitegravir and cobicistat (optionally, STRIBILD™); tenofovir (or disoproxil or emtricitabine) and elvitegravir and cobicistat (COMPLERA™ or EVIPLERA™); molnupiravir, efavirenz (optionally, SUSTIVA™), emtricitabine and tenofovir (ATRIPLA); lamivudine, nevirapine and stavudine (optionally, TRIOMUNE™); atazanavir and cobicistat (optionally, EVOTAZ™); lamivudine and raltegravir (optionally, DUTREBIS™); lamivudine and dolutegravir (or DOVATO™); doravirine, lamivudine and tenofovir (optionally, DELSTRIGO™); or lamivudine, zidovudine and nevirapine (optionally, CUOVIR-N™);

and optionally the additional anti-viral drug or medication, or anti-microbial drug, is formulated with the chloroquine (optionally, ARALEN™), chloroquine phosphate, chloroquine diphosphate, hydroxychloroquine (optionally, PLAQUENIL™), lopinavir, ritonavir (or NORVIR™) and/or oseltamivir or is formulated separately from the chloroquine (optionally, ARALEN™), chloroquine phosphate, chloroquine diphosphate, hydroxychloroquine (optionally, PLAQUENIL™), lopinavir, ritonavir (or NORVIR™) and/or oseltamivir, and optionally the anti-viral drug or medication, or anti-microbial drug, or palliative agent comprises or further comprises: magnesium (Mg, optionally administer intravenously (IV) to maintain a blood concentration of between about 2.0 and 2.4 mmol/1); zinc or any zinc salt (optionally a zinc sulphate, acetate, gluconate or picolinate, optionally administered at about 75 to 100 mg/day or at a dosage of between about 1 mg to 250 mg); at least one vitamin, wherein optionally the at least one vitamin comprises vitamin K, vitamin D or calcifediol (optionally D2 (or ergocalciferol) or Vitamin D3 or cholecalciferol), optionally administered at about 1000 to 4000 ugm/day), vitamin B6 (or pyridoxine), vitamin B12, vitamin E, and/or vitamin C (optionally administered at 500 mg bid); a flavonoid, plant flavonol or quercetin optionally administered at between about 250 to 500 mg bid; atorvastatin, or LIPITOR™, SORTIS™ (optionally administered at between about 40 mg/day to 80 mg/day); or, melatonin, or CIRCADIN™, SLENYTO™ (optionally between about 6 to 12 mg a day, optionally, at night), any of which are optionally given enterally or parenterally.

Anti-Clotting or Blood Thinning Agents

In alternative embodiments for practicing methods as provided herein, to address the possibility of blood clotting, whether the blood clotting is caused by the infectious agent, the administered inactivated or attenuated causative agent of the infection, or the live, viable or infectious causative agent of the infection, and/or the vaccine or for any another reason, an anti-clotting or anti-coagulant or blood thinning drug or agent is also administered, for example, before and/or at the commencement of the vaccination, and optionally is continued for between about 1 to 2 or 1 to 6 weeks after the vaccination, or for the duration of the anti-microbial drug treatment though administration of a second or booster vaccination, and/or for between about 1 to 2 weeks after administration of the second or booster vaccination.

In alternative embodiments, the anti-clotting agent or anti-coagulant or blood thinning drug or agent comprises aspirin, for example between about 100 mg to 500 mg aspirin administered (for example, in the morning, or AM, or MANE) for 2, 3, 4, 6, 7, 8, 9, 10, 11, 12, 13 or 14 or more days commencing on the day of the vaccination or commencing one or two days before the vaccination day.

In alternative embodiments, antiplatelet drugs that can be used include clopidogrel (PLAVIX™), prasugrel (EFFIENT™) and ticagrelor (BRILINTA™).

In alternative embodiments, the anti-clotting or anti-coagulant agent or blood thinning drug or agent comprises: heparin; warfarin (or COUMADIN™); a coumarin; phenprocoumon (or MARCUMAR™); rivaroxaban (XARELTO™); dabigatran (PRADAXA™); apixaban (ELIQUIS™); edoxaban (LIXIANA™) and/or betrixaban (BEVYXXA™).

Vaccines

In alternative embodiments, provided are methods for treating, ameliorating, decreasing the chances of having any adverse effects from, decreasing the severity of adverse effects from, or preventing an infection by administration of an antibiotic and/or an anti-viral drugs and a vaccine directed to a causative agent of the infection, and/or an inactivated or attenuated causative agent of the infection, or a live, viable or infectious causative agent of the infection.

In alternative embodiments, vaccines used to practice methods as provided herein are directed to an exterior-expressed protein of a pathogen, for example, where the pathogen is a bacteria or a virus, for example, the exterior-expressed protein comprises a spike protein of a virus, for example, a spike protein of a coronavirus, for example, a Covid-19 spike protein.

In alternative embodiments, vaccines used to practice methods as provided herein are formulated and administered using any formulations, protocols or techniques known in the art, for example, pharmaceutical formulations or vaccines as provided herein can be administered as peptides, or can be administered in the form of nucleic acids that encode the immunogenic peptides or proteins. In alternative embodiments, vaccines used to practice methods as provided herein comprise orally and intra-nasally administered vaccines.

In alternative embodiments, vaccines used to practice methods as provided herein comprise administration of inactivated pathogen, for example, an inactivated virus (optionally an inactivated whole or entire pathogen (or virus) or substantially a whole or entire pathogen (or virus), for example, an inactivated coronavirus, for example, and inactivated COVID-19 virus, for example, as manufactured by Valneva, France), Sinopharm, or Bharat Biotech. In alternative embodiments, the pathogen (or virus) is inactivated using a chemical, for example, a beta-propiolactone (BPL) or equivalent, or any means used to inactivate a viruses for a vaccine. This type of inactivation can preserve the structure of the pathogen (for example, viral) proteins, as they would occur in nature. This means the immune system will be presented with something similar to what occurs naturally and mount a strong immune response. In alternative embodiments, after being inactivated, the vaccine (or, the inactivated pathogen, or virus) is highly purified. In alternative embodiments, an adjuvant (or any immune stimulant) is added or co-administered to induce a boosted or strong immune response.

In alternative embodiments, vaccines used to practice methods as provided herein are DNA vaccine or RNA vaccines. For example, in alternative embodiments the immunogen-encoding nucleic acid can be a DNA encoding one or more immunogenic peptides or proteins, and the DNA can be carried in an expression vehicle such as a viral vector, for example an adenovirus vector such as an Ad5 or adeno-associated vector (AAV). In alternative embodiments, recombinant adenoviruses as used in vaccines as provided herein can be as described in U.S. patent application no. US 20200399323 A1, which describes for example recombinant adenoviruses including a deletion in or of the E1 region or any deletion that renders the virus replication-defective, for example, the replication-defective virus can include a deletion in one or more of the E1, E3, and/or E4 regions; or, can be as described in U.S. patent application no. US 20190382793 A1, which described how to make recombinant adenoviruses for gene therapy.

In alternative embodiments, the immunogen-encoding nucleic acid can be an RNA, for example, mRNA, which can be formulated in a lipid formulation or a liposome and injected for example intramuscularly (IM), for example using formulations and methods as described in U.S. patent application no. US 20210046173 A1, which describes delivering to a subject (for example, via intramuscular administration) an immunogenic composition that comprises a RNA (for example, mRNA) that comprises an open reading frame (ORF) that comprises (or consists of, or consists essentially of) an immunogenic or antigenic sequence as provided herein; wherein optionally the RNA (or the DNA-carrying expression vehicle) is formulated in a liposome, or a lipid nanoparticle (LNP), or nanoliposome, that comprises: non-cationic lipids comprise a mixture of cholesterol and DSPC, or a PEG-lipid, or PEG-modified lipid, or LNP, or an ionizable cationic lipid; or a mixture of (13Z,16Z)-N,N-dimethyl-2-nonylhenicosa-12,15-dien-1-amine, cholesterol, DSPC, and PEG-2000 DMG. In alternative embodiments, the PEG-lipid is 1,2-Dimyristoyl-sn-glycerol methoxypolyethylene glycol (PEG-DMG), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA), or, the PEG-lipid is PEG coupled to dimyristoylglycerol (PEG-DMG). In alternative embodiments, the LNP comprises 20-99.8 mole % ionizable cationic lipids, 0.1-65 mole % non-cationic lipids, and 0.1-20 mole % PEG-lipid. In alternative embodiments, the LNP comprises an ionizable cationic lipid selected from the group consisting of (2S)-1-({6-[(3))-cholest-5-en-3-yloxy]hexyl}oxy)-N,N-dimethyl-3-[(9 Z)-octadec-9-en-1-yloxy]propan-2-amine; (13Z,16Z)-N,N-dimethyl-3-nonyldocosa-13,16-dien-1-amine; and N,N-dimethyl-1-[(1S,2R)-2-octylcyclopropyl]heptadecan-8-amine; or a pharmaceutically acceptable salt thereof, or a stereoisomer of any of the foregoing. In alternative embodiments, the PEG modified lipid comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In alternative embodiments, the ionizable cationic lipid comprises: 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy) heptadecanedioate (L319), (13Z,16Z)-N,N-dimethyl-3-nonyldocosa-13,16-dien-1-amine, (12Z,15Z)-N,N-dimethyl-2-nonylhenicosa-12,15-dien-1-amine, and N,N-dimethyl-1-[(1S,2R)-2-octylcyclopropyl]heptadecan-8-amine. In one embodiment, the lipid is (13Z,16Z)-N,N-dimethyl-3-nonyldocosa-13,16-dien-1-amine or N,N-dimethyl-1-[(1S,2R)-2-octylcyclopropyl]heptadecan-8-amine, each of which are described in PCT/US2011/052328, the entire contents of which are hereby incorporated by reference. In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, or mixtures thereof.

Attenuated, or Live, Viable or Infectious Causative Agent of the Infection

In alternative embodiments, provided are methods for treating, ameliorating, decreasing the chances of having any adverse effects from, decreasing the severity of adverse effects from, or preventing an infection, comprising administering to a subject or an individual in need thereof:

(a) at least one antibiotic and/or anti-viral drug capable of killing a causative agent of the infection, or completely or partially inhibiting the ability of the causative agent of the infection to replicate or become infectious or cause pathology in the subject or the individual in need thereof; and, (b) (i) at least one dose of a vaccine directed to the causative agent of the infection upon entry into the vaccinated subject or individual in need thereof,
wherein the vaccine is capable of initiating an immune response in the individual that can substantially or partially kill or neutralize a causative agent of the infection, or the vaccine can completely, substantially or partially inhibit the ability of the causative agent of the infection to replicate, or be infectious, or cause pathology, in the subject or the individual in need thereof, and/or (ii) an inactivated or attenuated causative agent of the infection, or a live, viable or infectious causative agent of the infection, wherein optionally the live causative agent of the infection is a completely or partially attenuated version of the causative agent,
wherein at least one dosage of the at least one antibiotic and/or anti-viral drug is administered 1, 2, 3, 4, 5, 6, 7, 8, 9, 10, 11, 12, 13 or 14 or more days before, or on the day of, a first dose of the at least one of a plurality of dosages of the vaccine is administered, or a dose of the inactivated, attenuated causative agent of the infection, or the live, viable or infectious causative agent of the infection.

In alternative embodiments, the causative agent of the infection is or comprises a bacteria, protozoan or a virus, or the causative agent of the infection is or comprises the causative agent of:

a viral infection, optionally a coronavirus, a virus that causes a common cold, an influenza virus (optionally an influenza A, B or C), a hepatitis virus, a respiratory syncytial virus (RSV), a Paramyxoviridae or measles virus, a Paramyxovirus or mumps virus, a Herpes simplex virus (HSV), a Cytomegalovirus (CMV), a Rubivirus or rubella virus, an Enterovirus, a viral meningitis, a rhinovirus, a human immunodeficiency virus (HIV), a varicella-zoster or chickenpox virus, an Orthopoxvirus or variola or smallpox virus, an Epstein-Barr virus (EBV), an Adenovirus, a Hantavirus, a Flaviviridae or Dengue virus, a Zika virus, or a chikungunya virus infection, a coronavirus infection, optionally a COVID-19 or a COVID-19 variant infection, or a Middle East respiratory syndrome virus (MERS-CoV) infection;

malaria caused by a parasite of the genus *Plasmodium* (optionally *P. vivax, P. falciparum, P. malariae, P. ovale,* or *P. knowlesi*);

dengue fever or dengue shock syndrome caused by a virus of the Flaviviridae family or a dengue virus;

a Flaviviridae family virus infection or a hepatitis or a hepatocellular carcinoma associated with viral hepatitis caused by a virus of the Flaviviridae family or a virus of the genus Hepacivirus or Hepacivirus C virus or hepatitis C;

filariasis, leprosy or streptocerciasis or an infection caused by a parasite of the superfamily Filarioidea (optionally *Brugia malayi, Brugia timori, Wuchereria bancrofti, Loa loa, Mansonella streptocerca, Mansonella ozzardi*, or *Mansonella perstans*);

leprosy or an infection caused by a parasite of the genus *Mycobacterium* (optionally *M. leprae* or M. lepromatosis*);

river blindness or onchocerciasis caused by a parasitic worm or a parasite of the genus *Onchocerca* (optionally *O. volvulus*);

a hookworm or a roundworm infection caused by a parasite of the genus *Ancylostoma* (optionally *A. duodenale* or *A. ceylanicum*) or *Necator* (optionally *N. americanus*);

trichuriasis or a whipworm infection caused by a parasite of the genus *Trichuris* (optionally *T. trichiura*); roundworm or an *Ascaris* infection that is caused by *Ascaris lumbricoides*;

scabies or a mite-carried infection caused by the parasite of the genus *Sarcoptes* (optionally *S. scabiei*);

typhus or an infection caused by a lice or a parasite of the order Phthiraptera (optionally *Pediculus humanus capitis*);

enterobiasis or an infection caused by a pinworm or a parasite of the genus *Enterobius* (optionally *E. vermicularis*); and/or pulicosis or an infection caused by a flea or an insect of the order Siphonaptera or of the genus *Pulex* (optionally *P. irritans*).

In alternative embodiments, the inactivated or attenuated causative agent of the infection, or the live, viable or infectious causative agent of the infection is administered orally or by inhalation. Alternatively, the inactivated or attenuated causative agent of the infection, or the live, viable or infectious causative agent of the infection can be administered by inclusion of the live, viable or infectious causative agent of the infection in a liquid (optionally to be administered as a drink or in drops such as nasal drops), a tablet, a lozenge, an aerosol, spray, or mist formulation that is inhaled or administered nasally or orally (optionally, by a puffer of a nebulizer), or the inactivated or attenuated causative agent of the infection, or the live, viable or infectious causative agent of the infection is formulated in a liquid (optionally the liquid is a sterile saline) solution which is ingested or gargled by the individual in need thereof.

In alternative embodiments, the source of the inactivated or attenuated causative agent of the infection, or the administered live, viable or infectious causative agent of the infection can be from an infected individual, such as a human patient, a domesticated, wild or lab animal, or from a lab-grown culture. In alternative embodiments, the source of the administered inactivated or attenuated causative agent of the infection, or the live, viable or infectious causative agent of the infection is from swab or sputum or other biological samples from an infected individual or patient. In alternative embodiments, the sputum or other biological sample from an infected individual or patient is diluted in a water or a saline prior to administrations.

In alternative embodiments, the administered inactivated or attenuated causative agent of the infection, or the live, viable or infectious causative agent of the infection is attenuated (in other words, its ability to cause pathogenesis is completely, substantially or partially abrogated or diminished, for example is genetically deleted or diminished by genomic engineering).

In alternative embodiments, to generate an attenuated (e.g., completed inactivated) version of a causative agent of the infection to be administered, the causative agent of the infection is passaged multiple times in culture (or in vitro) or in an animal (or in vivo), where variants from each passage are selected for a phenotype and/or genotype that has diminished ability to cause pathogenesis.

In alternative embodiments, to generate an attenuated (e.g., completed inactivated, completely non-infectious) version of a causative agent of the infection to be administered, the causative agent of the infection is treated with radiation and/or a chemical. For example, the chemical can be iodine (for example, povidone-iodine or PVP-I, also known as iodopovidone, or BETADINE™, WOKADINE™, PYODINE™), or any complex of polyvinylpyrrolidone and iodine, alcohol and/or formalin.

In alternative embodiments, the causative agent of the infection is rendered inactive, or non-infectious, by exposing the causative agent of the infection to iodine or povidone-iodine or PVP-I (povidone is also known as polyvinylpyrrolidone (PVP), or 1-vinyl-2-pyrrolidinon-polymere), also known as iodopovidone, or BETADINE™, WOKADINE™, PYODINE™, as in the production of nasodine (Firebrick Pharma Pty Ltd, Australia). Povidone-iodine is a chemical complex of povidone, hydrogen iodide, and elemental iodine or triiodide ($I^{3-}$); and it contains 10% povidone, with total iodine species equaling 10,000 ppm or 1% total titratable iodine, and it works by releasing iodine which results in the death of a range of microorganisms. In alternative embodiment, the causative agent of infection is mixed with PVP-I and water, ethyl alcohol, isopropyl alcohol, polyethylene glycol or glycerol.

In alternative embodiments, the attenuated, or inactivated, causative agent, or live causative agent, is administered with an adjuvant, where the adjuvant can comprise: an inorganic compound such as alum (e.g., potassium alum), an aluminium salt or aluminium hydroxide, aluminium phosphate, or calcium phosphate; an oil such as paraffin oil, propolis or Adjuvant 65; a bacterial product such as killed bacteria of the genus *Bordetella* or *Mycobacterium* or of the species *Bordetella pertussis* or *Mycobacterium bovis*; a plant saponin or soybean extract; a cytokine such as interleukin-1 (IL-1), IL-2 or IL-12; Freund's complete adjuvant or Freund's incomplete adjuvant; and/or, an organic compound such as squalene.

In alternative embodiments, the attenuated, or inactivated, causative agent, or live causative agent, with or without an adjuvant, is administered by nasal spray or nebulizer, or orally for example by lozenge, tablet, capsule or geltab, or by subcutaneous injection, or intramuscularly (IM), or by suppository, or via an implant.

In alternative embodiments, attenuated viruses are made using a live attenuated codon-pair-deoptimized virus approach as described for example in Wang et al PNAS, Jul. 20, 2021, vol. 18 (29) e2102775118; or as described by Coleman et al. Science 320, 1784-1787 (2008), or Cheng et al J. Virol. 89, 3523-3533 (2015), or Gonsalves-Carneiro, mBio 12, e02238-20 (2021).

For example, methods as provided herein comprise administration of the Wang et al, COVI-VAC™ attenuated virus, which was developed by recoding a segment of the viral spike protein with synonymous suboptimal codon pairs (codon-pair deoptimization), thereby introducing 283 silent (point) mutations. As described by Wang et al, synthetic highly attenuated live vaccine is generated by recoding portions of the WT SARS-CoV-2 genome according to the SAVE algorithm of codon-pair bias deoptimization. In addition, the furin cleavage site within the spike protein was deleted from the viral genome for added safety of the vaccine strain. Except for the furin cleavage site deletion, the COVI-VAC and parental SARS-CoV-2 amino acid sequences are identical, ensuring that all viral proteins can engage with the host immune system of vaccine recipients. Attenuated viruses can be generated from viral genomes recover from WT SARS-CoV-2, strain USA-WA1/2020 (GenBank accession No. MN985325).

In alternative embodiments, the inactivated or attenuated causative agent of the infection, or the live, viable or infectious causative agent of the infection, is administered in unit dosages of between about 10 to 50, or 1 to 20, trillion infectious units (or particles, if attenuated), or between about one infectious unit to 10, 20 or 30 billion infection units (or particles, if attenuated).

Hand-Held or Portable Devices

In alternative embodiments, provided are portable, for example, hand-held (or worn around the neck), medical devices, for example, an inhaler, ionizer, asthma puffer or nebulizer, capable of administering an inhalation product comprising a composition or formulation as provided herein or as described herein, for example, an inactivated or attenuated agent of the infection, or a live, viable or infectious causative agent of the infection with or without a vaccine or with or without an adjuvant, or with or without an antimicrobial drug, for example, as described herein.

In alternative embodiments, a portable, for example, hand-held, medical device, for example, inhaler, asthma puffer or nebulizer, as provided herein can administer ionized air or air comprising generated electrons and/or negatively-charged oxygen ions and/or positively-charged ions.

In alternative embodiments, a portable or hand-held medical device as provided herein comprises a cassette, packette, interchangeable disk (for example, for holding a powder) or reservoir (optionally a refillable reservoir) in or on the product of manufacture, or a removable cassette or packette, interchangeable disk (for example, for holding a powder) that can be inserted into a slot or port on the product of manufacture, or a separate reservoir or container operatively linked or joined to the product of manufacture, that comprises a vaccine or or live or attenuated causative agent of invention or a formulation or a medication, for inhalation as provided herein for delivery to a user.

In alternative embodiments, provided is a modified hairdryer-type medical device capable of having an adjustable temperature, adjustable air intake; a provision (or receptacle) for insertion of a drug-containing cassette (optionally providing or delivering a combination of medications, or the live or attenuated causative agents and/or a vaccine as provided herein); and/or warm-to hot air availability (optionally with temperature control) to inhibit viral and bacterial growth.

In alternative embodiments, a medical device as provided herein for inhalation delivery of a live or attenuated causative agent of infection and/or a vaccine as provided herein drug or a medication or combinations thereof to a user is fabricated as a meter-dose inhaler (MDI) (either open or closed mouth MDI), which can comprise a pressurized canister of the drug or medication in a plastic case with a mouthpiece, and a holding chamber having a plastic tube with a mouthpiece, a valve to control mist delivery and a soft sealed end to hold the MDI; the holding chamber can assist delivery of the drug or medication to the nose and/or lungs, for example, as an AEROCHAMBER™ device.

In alternative embodiments, the inhaler or nebulizer is breath activated, for example, as an REDIHALER™ device.

In alternative embodiments, a medical device as provided herein for inhalation delivery of a live or attenuated causative agent of infection and/or a vaccine or a drug or a medication or combinations thereof to a user is fabricated a dry powder inhaler (such as a dry powder disk inhaler, for example, as a DISKUS™ device), optionally having a dose counter window so user can see how many doses are left), for example, where the powder is dose dispensed by (using) a disposable, refillable or replaceable cassette, packette or disk; and the dry powder dispensing can be breath activated, for example, as an AEROLIZER™, FLEXHALER™, PRESSAIR™, DISKUS™, HANDIHALER™, TWISTHALER™, ELLIPTA™, NEOHALER™, RESPICLICK™, ROTAHALER™ or TUBUHALER™ device.

In alternative embodiments, a medical device as provided herein for inhalation delivery of a live or attenuated causative agent of infection, or a vaccine or a drug or a medication or combinations thereof, to a user is fabricated a nebulizer or soft mist inhaler, which can comprise a nebulizer delivery system comprising a nebulizer (for example, a small plastic bowl with a screw-top lid) and a source for compressed air to generate a mist comprising the drug or medication, which also can be dose dispensed using a disposable, refillable or replaceable cassette, packette or disk.

In alternative embodiments, a medical device as provided herein for inhalation delivery of a live or attenuated causative agent of infection, or a vaccine or drug or a medication or combinations thereof to a user is fabricated a dry powder inhaler (such as a dry powder disk inhaler, for example, as a DISKUS™ device), optionally having a dose counter window so user can see how many doses are left), for example, where the powder is dose dispensed by (using) a disposable, refillable or replaceable cassette, packette or disk; and the dry powder dispensing can be breath activated, for example, as an AEROLIZER™, FLEXHALER™, PRESSAIR™, DISKUS™, HANDIHALER™, TWISTHALER™, ELLIPTA™, NEOHALER™, RESPICLICK™, ROTAHALER™ or TUBUHALER™ device.

Products of Manufacture and Kits

Provided are products of manufacture and kits for practicing methods as provided herein; and optionally, products of manufacture and kits can further comprise instructions for practicing methods as provided herein.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About (use of the term "about") can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 75%, 80%, 85%, 90%, 91%, 92%, 93%, 94%, 95%, 96%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention.

A number of embodiments of the invention have been described. Nevertheless, it can be understood that various modifications may be made without departing from the spirit and scope of the invention. Accordingly, other embodiments are within the scope of the following claims.

RELATED APPLICATIONS

This U.S. Utility Patent application claims the benefit of priority under 35 U.S.C. § 119(e) of U.S. Provisional Application Serial No. (USSN) 63/186,660, filed May 10, 2021; U.S. Ser. No. 63/188,311, May 13, 2021; U.S. Ser. No. 63/214,997, Jun. 25, 2021; U.S. Ser. No. 63/223,427, Jul. 19, 2021; U.S. Ser. No. 63/241,485 filed Sep. 7, 2021; U.S. Ser. No. 63/253,813 filed Oct. 8, 2021; and, U.S. Ser. No. 63/273,069, filed Oct. 28, 2021. The aforementioned applications are expressly incorporated herein by reference in its entirety and for all purposes.

TECHNICAL FIELD

This invention generally relates to medicine and the medical treatment of infections with vaccines, antibiotics and anti-viral drugs. In alternative embodiments, provided are methods for treating, ameliorating, decreasing the chances of having any adverse effects from, decreasing the severity of adverse effects from, or preventing an infection by administration of an antibiotic and/or an anti-viral drugs and a vaccine directed to a causative agent of the infection and/or an inactivated or attenuated causative agent of the infection, or a live, viable or infectious causative agent of the infection. In alternative embodiments, the infection is bacterial, parasitic or viral. In alternative embodiments, the viral infection is a coronavirus infection such a Covid-19 or Covid-19 variant infection. In alternative embodiments, methods as provided herein prevent or decrease the prevalence or severity of "vaccine breakthrough infections" after vaccination, where mutants of the infection's causative agent develop and infect patients in spite of the fact that they have undergone immunization, for example, to prevent a Covid-19 infection. In alternative embodiments, methods as provided herein are used to prevent in vivo mutations of an infectious agent to enhance to efficacy of an administered vaccination; in other word, methods as provided herein are used to prevent in vivo replication of a viral infectious agent, and thus also prevents mutations of the viral infectious agent because where there is no replication of infectious agent there is no mutation of infectious agent. In alternative embodiments, methods comprising administration of a combination of an antiviral medication, drug or treatment such as PF-07321332 or PAXLOVID™ and/or ritonavir and a vaccine prevents acquisition of externally mutated viruses infecting the vaccinated person, as well as preventing replication in those possessing less effective neutralising antibodies to the mutants.

BACKGROUND

The process of immunization attempts to create immunity to prevent acquisition of the new coronavirus or viruses. However, there is ongoing mutation occurring in the surrounding population because of ongoing replication of viruses. Hence, "vaccine breakthrough" infections are becoming reported, for example, see Hacisuleyman et al., New Eng J Med, Apr. 21, 2021. If the vaccine creates immunity to only the strains it was created for, it may permit 'reinfection' with Covid-19 of a mutant strain inhaled by the immunized person. This is termed "Vaccine breakthrough'. Within the immunized person replication of an external infectious mutant can take place because the vaccine alone is inadequate to control the mutant replicating and the mutant strain may further mutate in this seemingly safely immunized subject.

With COVID-19, there has been a rush into development of vaccines that could prevent the disease. However, the nature of this infection, being an intracellular RNA type of virus, does not result in an easy development of a vaccine. There are vaccines which work, for example, small pox, tetanus, polio, or measles, and there are conditions where vaccines are of little use, for example, hepatitis C, human immunodeficiency virus (HIV) infection and tuberculosis (TB), and then there are vaccines which only give partial immunization and for a short period of time, such as for example influenza virus immunization and more recently malaria immunization attempts.

Currently used mRNA vaccines as well as non-mRNA vaccines are manufactured by different companies such as Pfizer, AstraZeneca, Moderna, Johnson and Johnson (Janssen), Sputnik V, NovaVax, Sinovac, Sinopharm, Biological E, Valneva, EpiVac Corona, Convidiciae, Covaxin and others. All have been subject to various local side effects such as a swollen arm, systemic side effects such as fever, aches and pains, overwhelming feeling of doom, discomfort, profound tiredness and other symptoms. A small percentage of patients develop thrombocytopenia and clotting which is reminiscent of disseminated intravascular coagulation as described by some, as well as neurologic, dermatologic, cardiac and other adverse effects.

The preventative success of mRNA vaccines has been reported to be up to 90% or more. However, in real life experience data in some countries has shown results of 50% to 90% efficacy. Some of these reduced efficacy levels may be due to mutants being present in that population. Unless vaccine manufacturers can predict the development of specific mutations, which is virtually impossible, the vaccine market will always suffer from such reduced efficacy in various regions of the world.

Because of the ongoing mutations around the world of COVID-19, there are multiple strains, including a current India strain, which has caused super-infections in patients who have been immunized, i.e., the so-called vaccine breakthrough phenomenon. The B.1.617 variant of the Covid-19, known more commonly as the double mutant strain, was first detected in India in October 2020. As the name suggests, the strain involves two variants of the virus. The E484Q mutation has characteristics of a previously detected variant—the E484K—which was seen in the fast-spreading Brazilian and South African variants, making it highly transmissible. The L452R mutation, on the other hand, helps the virus evade the body's immune response. The double mutation strain was subsequently named B.1.617

Yet it is clear that the virus had to replicate to mutate. Hence the adage "if it cannot replicate it cannot mutate". Hence, one simple solution to the problem of imperfect vaccine disease prevention is not a bigger and better vaccine or multiple vaccinations because we will never keep up with the mutations. The best solution may well be prevention of mutations. Yet it is clear that the virus had to replicate to mutate. And subsequently replicate in the immunized person. Hence the adage "if it cannot replicate it cannot mutate".

SUMMARY

In alternative embodiments, provided are methods for treating, ameliorating, decreasing the chances of having any adverse effects from, decreasing the severity of adverse effects from, or preventing an infection, comprising administering to a subject or an individual in need thereof, wherein optionally the individual in need thereof is a human or an animal:
(a) at least one antibiotic and/or anti-viral drug capable of killing a causative agent of the infection, or completely or partially inhibiting the ability of the causative agent of the infection to replicate or become infectious or cause pathology in the subject or the individual in need thereof; and,
(b) (i) at least one dose of a vaccine directed to the causative agent of the infection upon entry into the vaccinated subject or individual in need thereof,
wherein the vaccine is capable of initiating an immune response in the individual that can substantially or partially kill or neutralize a causative agent of the infection, or the vaccine can completely, substantially or partially inhibit the ability of the causative agent of the infection to replicate, or be infectious, or cause pathology, in the subject or the individual in need thereof, and/or
(ii) an inactivated or attenuated agent of the infection, or a live, viable or infectious causative agent of the infection, wherein optionally the live causative agent of the infection is a completely or partially attenuated version of the causative agent,
wherein at least one dosage of the at least one antibiotic and/or anti-viral drug is administered 1, 2, 3, 4, 5, 6, 7, 8, 9, 10, 11, 12, 13 or 14 or more days before, or on the day of, a first dose of the at least one of a plurality of dosages of the vaccine is administered, or a dose of the inactivated, attenuated, or the live, viable or infectious causative agent of the infection.

In alternative embodiments, the causative agent of the infection is or comprises a bacteria, protozoan or a virus, or the causative agent of the infection is or comprises the causative agent of:
a viral infection, optionally a coronavirus, a virus that causes a common cold, an influenza virus (optionally an influenza A, B or C), a hepatitis virus, a rous sarcoma virus (RSV), a Paramyxoviridae or measles virus, a Paramyxovirus or mumps virus, a Herpes simplex virus (HSV), a Cytomegalovirus (CMV), a Rubivirus or rubella virus, an Enterovirus, a viral meningitis, a rhinovirus, a human immunodeficiency virus (HIV), a varicella-zoster or chickenpox virus, an Orthopoxvirus or variola or smallpox virus, an Epstein-Barr virus (EBV), an Adenovirus, a Hantavirus, a Flaviviridae or Dengue virus, a Zika virus, or a chikungunya virus infection,
a coronavirus infection, optionally a COVID-19 or a COVID-19 variant infection, or a Middle East respiratory syndrome virus (MERS-CoV) infection;
malaria caused by a parasite of the genus *Plasmodium* (optionally *P. vivax, P. falciparum, P. malariae, P. ovale*, or *P. knowlesi*);
dengue fever or dengue shock syndrome caused by a virus of the Flaviviridae family or a dengue virus;
a Flaviviridae family virus infection or a hepatitis or a hepatocellular carcinoma associated with viral hepatitis caused by a virus of the Flaviviridae family or a virus of the genus Hepacivirus or Hepacivirus C virus or hepatitis C;
filariasis, leprosy or streptocerciasis or an infection caused by a parasite of the superfamily Filarioidea (optionally *Brugia malayi, Brugia timori, Wuchereria bancrofti, Loa loa, Mansonella streptocerca, Mansonella ozzardi*, or *Mansonella perstans*);
leprosy or an infection caused by a parasite of the genus *Mycobacterium* (optionally *M. leprae* or M. lepromatosis);
river blindness or onchocerciasis caused by a parasitic worm or a parasite of the genus *Onchocerca* (optionally *O. volvulus*);
a hookworm or a roundworm infection caused by a parasite of the genus *Ancylostoma* (optionally *A. duodenale* or *A. ceylanicum*) or Necator (optionally *N. americanus*);
trichuriasis or a whipworm infection caused by a parasite of the genus *Trichuris* (optionally *T. trichiura*); roundworm or an *Ascaris* infection that is caused by *Ascaris lumbricoides;*
scabies or a mite-carried infection caused by the parasite of the genus *Sarcoptes* (optionally *S. scabiei*);
typhus or an infection caused by a lice or a parasite of the order Phthiraptera (optionally *Pediculus humanus capitis*);
enterobiasis or an infection caused by a pinworm or a parasite of the genus *Enterobius* (optionally *E. vermicularis*); and/or pulicosis or an infection caused by a flea or an insect of the order Siphonaptera or of the genus *Pulex* (optionally *P. irritans*).

In alternative embodiments, the virus is an influenza virus or a coronavirus, optionally a COVID-19 virus.

In alternative embodiments, the at least one antibiotic and/or anti-viral drug comprises: an avermectin class drug (optionally ivermectin) alone; a combination of an avermectin class drug and an antibiotic, or a combination of an ivermectin and an antibiotic or an antiviral drug or therapeutic, optionally a combination of an avermectin class drug, an antibiotic and zinc or a zinc salt, or a combination of ivermectin and an antibiotic and zinc or a zinc salt.

In alternative embodiments, the avermectin class drug comprises: ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin. In alternative embodiments, the avermectin class drug is administered with a synthetic nucleoside analog or derivative, or N4-hydroxycytidine, or a prodrug of N4-hydroxycytidine, optionally molnupiravir (Merck), or favipiravir (also known as T-705 or AVIGAN™, or favilavir, Toyama Chemical, Fujifilm, Japan, or FABIFLU™, Glenmark Pharmaceuticals).

In alternative embodiments, the antibiotic comprises an antibacterial antibiotic or a macrolide drug,
  wherein optionally the macrolide drug comprises azithromycin, optionally dosaged at between about 50 mg to about 2000 mg per dose or per day (optionally, ZITHROMAX™, or AZITHROCIN™, optionally an oral extended- or delayed-release formulation of azithromycin, or ZMAX™), clarithromycin (optionally, BIAXIN™), erythromycin (optionally, ERYTHROCIN™), or fidaxomicin (optionally, DIFICID™ or DIFICLIR™), troleandomycin (optionally, TEKMISIN™), tylosin (optionally, TYLOCINE™ or TYLAN™), solithromycin (optionally, SOLITHERA™), oleandomycin (or SIGMAMYCINE™), midecamycin, roxithromycin, kitasamycin or turimycin, josamycin, carbomycin or magnamycin, and/or spiramycin,
  and optionally the antibacterial antibiotic comprises a tetracycline class drug, a glycylcycline or a fluorocycline class drug, or an analogue thereof, and optionally the tetracycline, glycylcycline or fluorocycline drug or analogue thereof comprises or is: tetracycline or SUMYCIN™; chlortetracycline or AUREOMYCIN™; oxytetracycline; demeclocycline or DECLOMYCIN™, DECLOSTATIN™, LEDERMYCIN™, BIOTERCICLIN™, DEGANOL™, DETECLO™, DETRAVIS™, MECICLIN™, MEXOCINE™, CLORTETRIN™; lymecycline; meclocycline; metacycline; minocycline or MINOCIN™; rolitetracycline; doxycycline, or DORYX™, DOXYHEXA™, DOXYLIN™; tigecycline or TYGACIL™; eravacycline or XERAVA™; sarecycline or SEYSARA™; omadacycline or NUZYRA™; or any combination thereof.

In alternative embodiments, the at least one antibiotic and/or anti-viral drug comprises a combination of ivermectin and doxycycline (optionally DORYX™, DOXYHEXA™, DOXYLIN™), optionally a combination of ivermectin, doxycycline and zinc or a zinc salt.

In alternative embodiments, the at least one antibiotic and/or anti-viral drug comprises a combination of ivermectin and azithromycin ZITHROMAX™, or AZITHROCIN™, optionally an oral extended-release formulation of azithromycin, or ZMAX™), optionally a combination of ivermectin, azithromycin and zinc or a zinc salt.

In alternative embodiments, the at least one antibiotic and/or anti-viral drug comprises a combination of hydroxychloroquine (optionally, PLAQUENIL™) and azithromycin (optionally, ZITHROMAX™, or AZITHROCIN™, optionally an oral extended-release formulation of azithromycin, or ZMAX™), optionally a combination of hydroxychloroquine, azithromycin and zinc or a zinc salt.

In alternative embodiments, the at least one antibiotic and/or anti-viral drug further comprises administration of a vitamin, optionally vitamin D and/or vitamin C.

In alternative embodiments, the zinc comprises: zinc sulphate, zinc acetate, zinc gluconate or zinc picolinate or a zinc salt.

In alternative embodiments, on the day of administration of, or at least one day after the first dose of: (a) the attenuated and/or the live, viable or infectious causative agent of the infection, and/or (b) the vaccine, is given, the individual in need thereof is administered more of the at least one antibiotic and/or anti-viral drug, or a different combination of an least one antibiotic and/or anti-viral drug, or a different dosage of the at least one antibiotic and/or anti-viral drug.

In alternative embodiments, the individual in need thereof is administered more of the at least one antibiotic and/or anti-viral drug, or a different combination of an least one antibiotic and/or anti-viral drug, or a different dosage of the at least one antibiotic and/or anti-viral drug on day zero (the day of administration), or day 1, 2, 3, 4, 5, 6, 7, 8, 9, 10, 11, 12, 13 or 14 after administration of the first dosage of the vaccine and/or the attenuated and/or the live, viable or infectious causative agent of the infection.

In alternative embodiments, a booster, or at least one second or follow-up administration of: at least one dosage of a vaccine and/or an attenuated and/or a live, viable or infectious causative agent of the infection, is given between about 1 week to one year (or between about two weeks to 9 months, or between about three weeks to 8 months, or between about one month to 7 months, or about 3, 4, 5, or 6 months) after the first administration of the at least one vaccine and/or the attenuated and/or the live, viable or infectious causative agent of the infection,
  and optionally, wherein on day zero, or at least one day, or about two days, after, administration of the second or additional or booster dose of the vaccine, and/or the attenuated and/or the live, viable or infectious causative agent of the infection, is given, the individual in need thereof is administered more of the at least one antibiotic and/or anti-viral drug, or a different combination of an least one antibiotic and/or anti-viral drug, or a different dosage of the at least one antibiotic and/or anti-viral drug.

In alternative embodiments, the individual in need thereof is administered more of the at least one antibiotic and/or anti-viral drug, or a different combination of an least one antibiotic and/or anti-viral drug, or a different dosage of the at least one antibiotic and/or anti-viral drug on day 1, 2, 3, 4, 5, 6, 7, 8, 9, 10, 11, 12, 13 or 14 after administration of the second or additional or booster dose of the vaccine and/or the attenuated and/or the live, viable or infectious causative agent of the infection.

In alternative embodiments, the at least one antibiotic and/or anti-viral drug is repeatedly administered about every 1, 2, 3, 4, 5, 6, 7, 8, 9, 10, 11, 12, 13 or 14 or more days for one or several weeks (optionally, 2, 3, 4, 5, or 6 weeks) until plasma ivermectin is detectable.

In alternative embodiments, the vaccine is: a nucleic acid-based vaccine, optionally an RNA vaccine or a DNA vaccine; a peptide or polypeptide-based vaccine; or, the vaccine comprises an inactivated virus.

In alternative embodiments, the anti-bacterial and/or anti-viral drug or drug combination, or the attenuated and/or the live, viable or infectious causative agent of the infection, or the vaccine, is administered orally or by inhalation, or the the anti-bacterial and/or anti-viral drug or drug combination or the attenuated and/or the live, viable or infectious causative agent of the infection is administered by inclusion in a liquid (optionally to be administered as a drink or in drops such as nasal drops or in a mist), a tablet, a capsule, a gel, a geltab, a powder, a lozenge, an aerosol, spray, or mist formulation that is inhaled or administered nasally or orally (optionally, by a puffer or a nebulizer), or is formulated in a liquid (optionally the liquid is a sterile saline) solution which is ingested or gargled by the individual in need thereof.

In alternative embodiments, the attenuated and/or the live, viable or infectious causative agent of the infection is administered in unit dosages of between about 10 to 50 trillion infectious units or particles, or between about one infectious unit or particle to 10, 20 or 30 billion infection units or particles.

In alternative embodiments, after the first administration of (a) the attenuated and/or the live, viable or infectious causative agent of the infection, and/or (b) the vaccine, the IgM, IgG and/or IgA levels in the individual in need thereof is tested and measured (qualitatively and/or quantitatively), and optionally if levels of the measured IgM, IgG and/or IgA are low, a second or additional dosage or administration of the (a) the attenuated and/or the live, viable or infectious causative agent of the infection, and/or (b) the vaccine, is given, and optionally levels of the measured IgM, IgG and/or IgA are measured at between about 7 to 21 days, or at 14 and 20 days, after the first administration.

In alternative embodiments, the individual in need thereof is a human or an animal, and optionally the animal is a domestic, farm or zoo animal.

In alternative embodiments, the methods comprise administering in coordination with (optionally before, at the time of and/or after vaccination of and/or administration of the attenuated and/or the live, viable or infectious causative agent of the infection) the anti-microbial (optionally antiviral) vaccine and/or the attenuated and/or the live, viable or infectious causative agent of the infection, a therapeutic combination of drugs or a single drug, an antisera or an antibody, a pharmaceutical dosage form, a drug delivery device, or a product of manufacture, comprising:

(a) a thiazolide class drug, optionally nitazoxanide (or ALINIA™ NIZONIDE™) or tizoxanide (or 2-Hydroxy-N-(5-nitro-2-thiazolyl)benzamide);

(b) molnupiravir, optionally co-administered with and/or formulated with an avermectin class drug (optionally ivermectin), an antibiotic (optionally doxycycline or azithromycin) and/or zinc, or co-administered with and/or formulated with ivermectin, hydroxychloroquine, an antibiotic (optionally doxycycline or azithromycin) and/or zinc;

(c) opaganib or YELIVA™, or opaganib or YELIVA™ and oral and/or inhaled or aerosol chloroquine (or ARALEN™), chloroquine phosphate, chloroquine diphosphate, amodiaquine (or AMDAQUINE™, AMOBIN™) and/or hydroxychloroquine (optionally, PLAQUENIL™), wherein optionally each or both of the opaganib and the chloroquine (or ARALEN™), chloroquine phosphate, chloroquine diphosphate and/or hydroxychloroquine (optionally, PLAQUENIL™) are in or formulated as a formulation for inhalation, for example, formulated as an aerosol, spray, mist, liquid or powder, or each or both are formulated for oral, intramuscular or intravenous administration, wherein optionally the opaganib is administered at a dosage of QD (once a day), bid (twice a day) or tid (three times a day) at a dosage of between about 100 to 600 mg per day or per dosage, or at about 100, 200, 300, 400, 500 or 600 mg per day or per dosage, and optionally the opaganib, or YELIVA™ is also administered or formulated with an antibiotic (optionally azithromycin or doxycycline), ivermectin (optionally at 12 mg ivermectin, optionally administered on days 1, 3, 6 and 8), hydroxychloroquine (optionally, PLAQUENIL™) and/or zinc (optionally zinc sulfate, optionally at (50 mg daily, or any zinc salt);

(d) lopinavir, ritonavir (or NORVIR™) and oseltamivir (optionally, TAMIFLU™), and/or zanamivir (or RELENZA™);

(e) lopinavir combined (formulated) with ritonavir (or NORVIR™), or KALETRA™, ALTERA™, ALUVIA™, KALMELTREX, LOPIMUNE™ or LOPINAVIR™, and/or zanamivir (or RELENZA™), or lopinavir and ritonavir separately formulated;

(f) lopinavir combined (formulated) with ritonavir (or NORVIR™) (or KALETRA™, ALTERA™, ALUVIA™, KALMELTREX, LOPIMUNE™ or LOPINAVIR™), or lopinavir and ritonavir (or NORVIR™), and oseltamivir (optionally, TAMIFLU™), and/or zanamivir (or RELENZA™), optionally also with inhaled or aerosol formulations or versions of chloroquine (or ARALEN™) amodiaquine (or AMDAQUINE™, AMOBIN™), chloroquine phosphate, and/or oral chloroquine (or ARALEN™), chloroquine phosphate, chloroquine diphosphate and/or hydroxychloroquine (optionally, PLAQUENIL™) simultaneously;

(g) lopinavir, ritonavir (or NORVIR™), amodiaquine (or AMDAQUINE™, AMOBIN™), chloroquine and oseltamivir (or TAMIFLU™); wherein optionally the chloroquine comprises inhaled or aerosol chloroquine (or ARALEN™), chloroquine phosphate, chloroquine diphosphate and/or hydroxychloroquine (optionally, PLAQUENIL™) and/or oral chloroquine (or ARALEN™), chloroquine phosphate, chloroquine diphosphate and/or hydroxychloroquine (optionally, PLAQUENIL™) simultaneously;

(h) lopinavir and oseltamivir (optionally, TAMIFLU™), and/or zanamivir (or RELENZA™);

(i) ritonavir (or NORVIR™) and oseltamivir (optionally, TAMIFLU™), and/or zanamivir (or RELENZA™);

(j) remdesivir (optionally, GS-5734™, Gilead Sciences) alone, or oseltamivir (optionally, TAMIFLU™) and remdesivir (optionally, GS-5734™, Gilead Sciences), and optionally the remdesivir is an oral formulation and/or an inhaled or aerosol remdesivir formulation;

(k) oseltamivir (optionally, TAMIFLU™) and efavirenz (optionally, SUSTIVA™), and/or zanamivir (or RELENZA™);

(l) oseltamivir (optionally, TAMIFLU™) and nevirapine (or the combination efavirenz with emtricitabine and tenofovir, or ATRIPLA™);

(m) oseltamivir (or TAMIFLU™) and amprenavir (optionally, AGENERASE™);

(n) oseltamivir (optionally, TAMIFLU™) and nelfinavir (optionally, VIRACEPT™);

(o) a thiazolide class drug, optionally nitazoxanide (optionally ALINIA™, NIZONIDE™) or tizoxanide (or 2-Hydroxy-N-(5-nitro-2-thiazolyl)benzamide), with or in combination with any of (a) to (hh), or any drug or drug combination as provided herein, optionally a thiazolide class drug, optionally nitazoxanide, with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin; or a thiazolide class drug (optionally, nitazoxanide or tizoxanide) and oseltamivir (or TAMIFLU™), and optionally the thiazolide class drug (optionally, nitazoxanide or tizoxanide) is formulated or administered with ribavirin or tribavirin (or COPEGUS™, REBETOL™, or VIRAZOLE™), and an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin;

(p) plitidepsin (also known as dehydrodidemnin B), or APLIDIN™ (PharmaMar, S. A.);

(q) an inhibitor or S-phase kinase-associated protein 2 (SKP2), or dioscin, or niclosamide, or NICLOCIDE™, FENASAL™, or PHENASAL™;

(r) ribavirin or tribavirin (or COPEGUS™, REBETOL™, or VIRAZOLE™) interferon beta 1b, or a combination of ribavirin and interferon beta, or a combination of lopinavir and ritonavir (or NORVIR™) and interferon-beta-1b;

(s) abacavir, acyclovir, or optionally ACICLOVIR™, adefovir, amantadine, ampligen, amprenavir (optionally, AGENERASE™), aprepitant, umifenovir (or ARBIDOL™), atazanavir, atripla, balavir, baloxavir marboxil (XOFLUZA™), bepotastine, bevirimat, bictegravir, a combination of bictegravir and emtricitabine and tenofovir alafenamide (or BIKTARVY™), brilacidin, bivalirudin (or BIVALITROBAN™), cidofovir, caspofungin, lamivudine and zidovudine (optionally, COMBVIR™), cobicstat, colisitin, cocaine, darunavir, delavirdine, descovy, didanosine, docosanol, dolutegravir, ecoliever, edoxudine, efavirenz (optionally, SUSTIVA™), elvitegravir, emtricitabine, enfuvirtide, entecavir, epirubicin, epoprostenol, etravirine, famciclovir, fomivirsen, fosamprenavi, foscarnet, fosfonet, galidesivir, ibacitabine, icatibant, idoxuridine, ifenprodil, imiquimod, imunovir, indinavir, inosine, an interferon (optionally interferon type I, interferon type II and/or interferon type III), lamivudine (or EPIVIR™, ZEFFIX™), lopinavir, loviride, ledipasvir, leronlimab, maraviroc, methisazone, moroxydine, nelfinavir, nevirapine, nexavir, nitazoxanide (optionally ALINIA™, NIZONIDE™), norvir, a nucleoside analogue or derivative (optionally brincidofovir (or TEMBEXA™), didanosine (or VIDEX™), favipiravir (also known as T-705 or AVIGAN™, or favilavir, Toyama Chemical, Fujifilm, Japan, or FABIFLU™, Glenmark Pharmaceuticals), vidarabine, galidesivir (optionally, BCX4430, IMMUCILLIN-A™), remdesivir (optionally, GS-5734™, Gilead Sciences), cytarabine, gemcitabine, emtricitabine, lamivudine, zalcitabine, abacavir, acyclovir, entecavir, stavudine, telbivudine, zidovudine, idoxuridine and/or trifluridine or any combination thereof), oseltamivir (or TAMIFLU™), peginterferon alfa-2a, penciclovir, peramivir (optionally, RAPIVAB™), perfenazine, pleconaril, plurifloxacin, podophyllotoxin, pyramidine, raltegravir, rifampicin, ribavirin or tribavirin (or COPEGUS™, REBETOL™, or VIRAZOLE™), rilpivirine, rimantadine, ritonavir (or NORVIR™) saquinavir, sofosbuvir, stavudine, telaprevir, tegobuv, tenofovir alafenamide, tenofovir disoproxil, tenofovir, tipranavir, trifluridine, trizivir, tromantadine, truvada, valaciclovir (optionally, VALTREX™), valganciclovir, valrubicin, vapreotide, vicriviroc, vidarabine, viramidine, velpatasvir, vivecon, zalcitabine, zanamivir (optionally, RELENZA™), zidovudine, an immunosuppressive drug (optionally tocilizumab or atlizumab, or ACTEMRA™, or ROACTEMRA™) or any combination thereof;

(t) a mucolytic therapy or drug, optionally acetylcysteine, ambroxol, bromhexine (or BISOLVON™), carbocisteine, erdosteine, mecysteine or dornase alfa, or an expectorant, optionally guaifenesin;

(u) a viral, or a coronavirus or a COVID-19, protease inhibitor, optionally ASC09 (CAS registry no. 1000287-05-7) (Janssen Research and Development, LLC), ritonavir (or NORVIR™) or ASC09 and ritonavir, or a JAK1/2 inhibitor (optionally baricitinib), optionally compound 11r (University of Lubeck, Germany, see optionally, Zhang et al J. Med Chem 2020, Feb. 11, 2020), or darunavir, cobicistat or darunavir and cobicistat;

(v) an angiotensin-converting enzyme 2 (ACE2) inhibitor, optionally to block the site of viral spike protein interaction for anti-SARS-CoV-2 infection control;

(w) an anti-vascular endothelial growth factor (VEGF) (optionally VEGF-A) drug or antibody, optionally bevacizumab;

(x) a protease inhibitor, optionally danoprevir, optionally a serine protease inhibitor, optionally camostat or narlaprevir (optionally ARLANSA™);

(y) anti-PD-1 checkpoint inhibitor, optionally camrelizumab;

(z) a compound or antibody capable of binding complement factor C5 and blocking membrane attack complex formation, optionally eculizumab;

(aa) a cathepsin inhibitor, optionally a cathepsin K, B or L inhibitor, optionally relacatib;

(bb) thalidomide, or thalidomide and glucocorticoid (optionally low-dose glucocorticoid), or and thalidomide and celecoxib;

(cc) an antibacterial antibiotic or a macrolide drug, wherein optionally the macrolide drug comprises azithromycin, optionally dosaged at between about 50 mg to about 2000 mg per dose or per day (optionally, ZITHROMAX™, or AZITHROCIN™, optionally an oral extended- or delayed-release formulation of azithromycin, or ZMAX™), clarithromycin (optionally, BIAXIN™), erythromycin (optionally, ERYTHROCIN™), or fidaxomicin (optionally, DIFICID™ or DIFICLIR™), troleandomycin (optionally, TEKMISIN™), tylosin (optionally, TYLOCINE™ or TYLAN™), solithromycin (optionally, SOLITHERA™), oleandomycin (or SIGMAMYCINE™), midecamycin, roxithromycin, kitasamycin or turimycin, josamycin, carbomycin or magnamycin, and/or spiramycin, and optionally the antibacterial antibiotic comprises a tetracycline class drug, a glycylcycline or a fluorocycline class drug, or an analogue thereof, and optionally the tetracycline, glycylcycline or fluorocycline drug or analogue thereof comprises or is: tetracycline or SUMYCIN™; chlortetracycline or AUREOMYCIN™; oxytetracycline; demeclocycline or DECLOMYCIN™, DECLOSTATIN™, LEDERMYCIN™, BIOTERCICLIN™, DEGANOL™, DETECLO™, DETRAVIS™, MECICLIN™, MEXOCINE™, CLORTETRIN™; lymecycline; meclocycline; metacycline; minocycline or MINOCIN™; rolitetracycline; doxycycline, or DORYX™, DOXYHEXA™, DOXYLIN™; tigecycline or TYGACIL™; eravacycline or XERAVA™; sarecycline or SEYSARA™; omadacycline or NUZYRA™; or any combination thereof, and optionally the antibacterial antibiotic or macrolide drug, optionally azithromycin (or ZMAX™), is administered in combination with, and/or is combined with, chloroquine (or ARALEN™), amodiaquine (or AMDAQUINE™, AMOBIN™), chloroquine phosphate, chloroquine diphosphate and/or hydroxychloroquine (optionally, PLAQUENIL™), and the combination is administered commencing on the first, second, third, fourth, fifth, sixth, seventh, eighth, ninth and/or tenth day of therapy, or is administered for 1, 2, 3, 4, 5, 6, 7, 8, 9, or up to 20 or more days, or for between about 1 to 21 days or longer, or is administered until within 1, 2, 3, 4, 5, 6, 7, 8, 9, 10 or up to 20 or more days of ending the therapy for treating, preventing, ameliorating, slowing the progress of, decreasing the severity of or preventing the coronavirus infection, and optionally the chloroquine (or ARALEN™), chloroquine phosphate, amodiaquine (or AMDAQUINE™, AMOBIN™), chloroquine diphosphate and/or hydroxychloroquine (optionally, PLAQUENIL™) is administered the entire length of the treatment but the azithromycin, optionally dosaged at between about 50 mg to about 2000 mg per dose or per day (optionally, ZITHROMAX™, or AZITHROCIN™, optionally an oral extended-release formulation of azithromycin, or ZMAX™) administration is halted or ceased after two, three, four, five or six days after treatment is commenced, and optionally the azithromycin administration is replaced by a tetracycline class drug, and optionally the tetracycline class drug comprises doxycycline, or DORYX™, DOXYHEXA™, DOXYLIN™ administration, and optionally the antibacterial antibiotic, optionally azithromycin (optionally, ZITHROMAX™, or AZITHROCIN™, optionally dosaged at between about 50 mg to about 2000 mg per dose or per day, and optionally an oral extended-release formulation of azithromycin, or ZMAX™), is administered or formulated with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and/or cholecalciferol (vitamin D3) or calcifediol, and optionally the antibacterial antibiotic comprises an antimycobacterial drug, and optionally the antimycobacterial drug comprises clofazimine (optionally LAMPRENE™);

(dd) an avermectin class drug such as ivermectin (optionally STROMECTOL™, SOOLANTRA™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, optionally dosaged and/or administered at about 5 microgram/kg to about 1 gram (g) per day, optionally formulated or administered at about 1 to 10, 12, 15, 20, 30, 40, 50, 60, 70, 80, 100, 120, 140, 160, 180, 200, 220 or 240 mg per day, or between about 1 to 240 mg per day, or between about 3 to 240 mg per day, optionally formulated or administered with an antibiotic (optionally azithromycin, minocycline, amoxicillin, niclosamide, nitazoxanide, hydroxychloroquine or doxycycline, and optionally the doxycycline is at between about 25 to 600 mg per dose or per day, or at about 100 mg per dose or per day, and optionally the azithromycin is at between about 50 mg to 2000 mg per dose or per day), optionally as a single or a divided dose, and optionally formulated and administered as an inhalant or a mist (optionally using a nebulizer, nasal spray or equivalent), optionally formulated as an aerosol, spray, mist, liquid or powder, optionally formulated as an aerosol, spray, mist, liquid or powder, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is formulated with and/or administered with chloroquine (or ARALEN™), chloroquine phosphate, chloroquine diphosphate and/or hydroxychloroquine (optionally, PLAQUENIL™) with or without zinc (optionally a zinc sulphate, acetate, gluconate or picolinate or any zinc salt), and optionally this combination is administered weekly, or every two week, or one every 5 to 28 days, as a prophylactic, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered alone in the morning (AM), and an antibiotic (optionally doxycycline) and/or a chloroquine (optionally, ARALEN™), chloroquine phosphate, chloroquine diphosphate and/or hydroxychloroquine (optionally, PLAQUENIL™) is administered in the afternoon and/or evening, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered alone for 1, 2, 3, 4, 5, 6, 7, 8, 9, 10 or up to 20 or more days, followed by administration of an antibiotic (optionally doxycycline) for a corresponding period of days, and optionally repeating the cycle of dosaging, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is formulated or administered with:
 (i) at least one antibiotic (wherein optionally the antibiotic is doxycycline(optionally, DORYX™, DOXYHEXA™, DOXYLIN™) (optionally formulated or administered at a dosage of between about 25 mg to 600 mg per dose or per day), or azithromycin (optionally, ZITHROMAX™, or AZITHROCIN™, optionally dosaged at between about 50 mg to about 2000 mg per dose or per day, optionally an oral extended-release formulation of azithromycin, or ZMAX™) (optionally formulated or administered at a dosage of between an about 50 mg to 2000 mg);
 (ii) chloroquine (or ARALEN™), chloroquine phosphate, chloroquine diphosphate and/or hydroxychloroquine (optionally, PLAQUENIL™) (optionally formulated or administered at a dosage of between an about 10 mg to 2000 mg per day);
 (iii) a zinc (optionally a zinc sulphate, acetate, gluconate or picolinate or any zinc salt) optionally formulated or administered at a dosage of between about 1 mg to 250 mg; and/or
 (iv) at least one vitamin, and optionally the at least one vitamin comprises: vitamin C optionally formulated or administered at a dosage of between about 500 to 5000 units (U) per dose, and/or Vitamin D (or cholecalciferol) optionally formulated or administered at a dosage of between about 3,000 to 100,000 units per day, or between about 10,000 to 50,000 units a day,
 and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered or formulated alone or in combination with any of the above (i) to (iv) (for example, at least one antibiotic, chloroquine (or ARALEN™) chloroquine phosphate, chloroquine diphosphate and/or hydroxychloroquine (optionally, PLAQUENIL™), zinc or any zinc salt and/or at least one vitamin are formulated (and administered) as oral formulations (for example, as tablets, capsules, powders, gels or geltabs), injectable formulations, powders (for example, for inhalation or for addition to an ingestible liquid) or liquids (for example, for ingestion, infusion or injection);
(ee) chloroquine (or ARALEN™), chloroquine phosphate, chloroquine diphosphate and/or hydroxychloroquine (optionally, PLAQUENIL™) alone or with (or formulated with) or in combination with any of (a) to (bb), or chloroquine, chloroquine phosphate, chloroquine diphosphate and/or hydroxychloroquine (optionally, PLAQUENIL™) and oseltamivir (or TAMIFLU™);
(ff) chloroquine (optionally, ARALEN™), chloroquine phosphate, chloroquine diphosphate and/or hydroxychloroquine (optionally, PLAQUENIL™) alone or with:
 (i) an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, optionally at a dosage of between about 3 to 340 mg per day, or about 6 mg to 60 mg, or about 10 mg to 80 mg dosages, or about 12 to 50 mg dosages;
 (ii) vitamin D, vitamin D2 (or ergocalciferol), vitamin D3 (or cholecalciferol) optionally at a dosage of between about 3,000 to 100,000 units per day, or between about 10,000 to 50,000 units a day, and/or
 (iii) with (i) and (ii) and zinc (optionally a zinc sulphate, acetate, gluconate or picolinate or any zinc salt) optionally at a dosage of between about 1 mg to 250 mg, or (iv) the combination of (iii) also with a tetracycline class drug, wherein optionally the tetracycline class drug comprises doxycycline, or DORYX™, DOXYHEXA™, DOXYLIN™, optionally dosages at between about 25 mg to 600 mg per day or per dose, optionally between about 100 mg to 500 mg, or a between about 200 mg to 400 mg per dose or per day;
(gg) colchicine, or COLCRYS™, MITIGARE™, optionally administered or dosaged at between about 0.5 mg to 20 mg, or about 1 mg to 15 mg, or about 3 mg to 10 mg, or about 4 mg to 6 mg, per day for a period of between about 7 and 21 days, or about 14 days, and optionally also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily);
(hh) a corticosteroid or glucocorticoid class drug such as ciclesonide (or ALVESCO™, OMNARIS™, OMNIAIR™, ZETONNA™ or ALVESCO™) budesonide (optionally RHINOCORT™ or PULMICORT™), prednisolone (or ORAPRED™), methylprednisolone, prednisone (or DELTASONE™ or ORASONE™) or hydrocortisone (or CORTEF™), or a selective estrogen receptor modulator (SERM), or toremifene (or FARESTON™), or clomifene or clomiphene (or CLOMID™, SEROPHENE™), wherein optionally the corticosteroid or glucocorticoid class drug (optionally ciclesonide) is inhaled;
and optionally the corticosteroid class drug (for example budesonide) is administered by inhalation, for example, in a nebulized form, for example, between about 1 mg to 12 mg per day of budesonide is administered by inhalation, or between about 6 to 80 mg per day of prednisolone is administered orally, or between about 6 to 100 mg per day of prednisone is administered orally, or between about 30 to 400 mg per day of hydrocortisone is administered orally,
and optionally the corticosteroid class drug is formulated as a powder or for administration in an inhaler or by nasal spray, or for rectal administration,
and optionally the corticosteroid class drug (for example, budesonide) is administered together with or in combination with 10 mg to 80 mg, an antibiotic (optionally azithromycin or a tetracycline class drug,
wherein optionally the tetracycline class drug comprises doxycycline, or DORYX™, DOXYHEXA™, DOXYLIN™), zinc or any zinc salt and/or a vitamin (optionally vitamin D or calcifediol, D2 (or ergocalciferol), D3 (or cholecalciferol), C, E, B12, B6);
(ii) an anti-androgen drug, and optionally the anti-androgen drug is bicalutamide, optionally CASODEX™, or dutasteride (or AVODART™),
and optionally the anti-androgen drug is a nonsteroidal anti-androgen (NSAA) or an androgen receptor (AR) antagonist, and optionally the NSAA or AR antagonist comprises proxalutamide (or its developmental name GT-0918) (Suzhou Kintor Pharmaceuticals, Inc., a subsidiary of Kintor Pharmaceutical Limited), or flutamide (or niftolide, or EULEXIN™), or bicalutamide (or CASODEX™) or enzalutamide (or XTANDI™),
and optionally the anti-androgen drug comprises a 5α-reductase inhibitor, and optionally the 5α-reductase inhibitor comprises finasteride (or PROSCAR™, PROPECIA™, or FINIDE™)
and optionally the anti-androgen drug, or NSAA, or proxalutamide or bicalutamide, is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin;
and optionally the anti-androgen drug, or NSAA, or bicalutamide, proxalutamide, flutamide or niftolide, bicalutamide, enzalutamide or dutasteride, is administered at dosages of about 50 to 100 mg optionally administered once, twice (BID), three times (TID) or four times a day, or is administered at dosages of about 50 to 100 mg per day,
and optionally the anti-androgen drug, or NSAA, or bicalutamide, proxalutamide, flutamide or niftolide, bicalutamide, enzalutamide or dutasteride, is administered with an avermectin class drug, or ivermectin, optionally also administered with hydroxychloroquine, zinc and/or a vitamin (optionally vitamin D (optionally vitamin D2, or ergocalciferol, or Vitamin D3 or cholecalciferol, optionally administered at about 1000 to 4000 ugm/day) or vitamin C, B or A;
and optionally bicalutamide is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin,
and optionally bicalutamide is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin;
(jj) a hydrocortisone or cortisol (optionally CORTEF™, SOLUCORTEF™), optionally hydrocortisone sodium succinate or hydrocortisone acetate or dexamethasome (optionally DEXTENZA™, OZURDEX™, NEOFORDEX™);

(kk) an alpha-ketoamide (α-ketoamide), wherein optionally the alpha-ketoamide is a structure as described by Zhang et al, J. Med. Chem. 2020, 63, 9, 4562-4578, or Meng et al Chem. Sci. (2019) vol. 10, pg 5156 (optionally the structure KAM-2),
and optionally the alpha-ketoamide is formulated or administered as an inhalant or a powder or mist, and optionally formulated or administered with (optionally as an inhalant): an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin; an antibiotic (optionally azithromycin or a tetracycline class drug, wherein optionally the tetracycline class drug comprises doxycycline, or DORYX™, DOXYHEXA™, DOXYLIN™); chloroquine (or ARALEN™), chloroquine phosphate, chloroquine diphosphate and/or hydroxychloroquine (optionally, PLAQUENIL™); zinc or any zinc salt; remdesivir (optionally, GS-5734™, Gilead Sciences); oseltamivir (or TAMIFLU™); and/or, hydrocortisone; or, any combination thereof;
(ll) a compound, drug or formulation that decreases stomach acid production or decreases stomach pH, wherein optionally the compound, drug or formulation comprises famotidine, or PEPCID™, and optionally the famotidine is administered at a dosage of between about 10 to 60 mg per day, or between about 20 to 40 mg per day, and optionally the famotidine is administered is administered with: an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and/or a tetracycline tetracycline class drug, and optionally the tetracycline class drug comprises doxycycline, or DORYX™, DOXYHEXA™, DOXYLIN™;
(mm) a dendrimer, optionally astodrimer sodium (Starpharma, Melbourne, Australia);
(nn) an antihistamine class drug such as azelastine, or ASTELIN™, OPTIVAR™, ALLERGODIL™, brompheniramine, fexofenadine or ALLEGRA™, pheniramine or AVIL™, or chlorpheniramine;
(oo) a selective serotonin reuptake inhibitor (SSRI) class drug, optionally fluvoxamine, or LUVOX™, FAVERIN™, FLUVOXIN™;
(pp) a nicotinic antagonist, a dopamine agonist or a noncompetitive N-Methyl-d-aspartic acid or N-Methyl-d-aspartate (NMDA) antagonist, wherein optionally the nicotinic antagonist, dopamine agonist or noncompetitive NMDA antagonist is 1-adamantylamine or amantadine, or GOCOVRI™, SYMADINE™, SYMMETREL™, optionally administered or dosaged at between about 50 mg to 150 mg, or about 100 mg, per day for a period of between about 7 and 21 days, or about 14 days, and optionally the nicotinic antagonist, dopamine agonist or noncompetitive NMDA antagonist is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally the amantadine is formulated or administered at 100 mg per day for the first two days of treatment, which optionally can then be elevated to 100 mg twice daily, optionally for the next 10 days;

(qq) an immunosuppressive drug, wherein optionally the immunosuppressive drug comprises tocilizumab or atlizumab, or ACTEMRA™, or ROACTEMRA™, or a calcineurin inhibitor (CNI), wherein the CNI comprises ciclosporin (or cyclosporine or cyclosporin), or NEORAL™, or SANDIMMUNE™, or tacrolimus, or PROTOPIC™, or PROGRAF™, and optionally the immunosuppressive drug is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally the calcineurin inhibitor (CNI), wherein the CNI comprises ciclosporin (or cyclosporine or cyclosporin) is formulated combination of CNI (optionally cyclosporine) at a dose of 3 mg/kg (180 mg daily) together with 12 mg ivermectin once, and optionally also plus zinc 50 mg base and doxycycline 100 mg bid, optionally all for 10 days;

(rr) a protein kinase inhibitor, wherein optionally the protein kinase inhibitor is a p38 mitogen-activated protein kinase inhibitor, or ralimetinib, and optionally the protein kinase inhibitor is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily);

(ss) an anti-inflammatory therapy or at least one anti-inflammatory therapy drug, wherein optionally the anti-inflammatory therapy or drug comprises: a sphingosine kinase-2 (SK2) selective inhibitor (optionally, opaganib (optionally, YELIVA™), sirolimus, a JAK1/2/TYK2 inhibitor (optionally ruxolitinib), an anti-CD47 mAb (optionally meplazumab), a cyclooxygenase (COX) (optionally, COX2) inhibitor, a glucocorticoid (optionally a synthetic glucocorticoid, hydrocortisone, dexamethasone (or DEXTENZA™, OZURDEX™, or NEOFORDEX™) or cortisol, or CORTEF™) or ciclesonide (or ALVESCO™, OMNARIS™, OMNIAIR™, ZETONNA™ or ALVESCO™), plitidepsin or dehydrodidemnin B, or APLIDIN™, or a nonsteroidal anti-inflammatory drug (NSAID), wherein optionally the NSAID comprises indomethacin (or indomethacin) or INDOCID™ or INDOCIN™, or naproxen, or NAPROSYN™ or ALEVE™, or a cyclooxygenase inhibitor, or a COX-1 or an COX-2 inhibitor, or aspirin, or ibuprofen or ADVIL™ MOTRIN™ or NUROFEN™, or celecoxib or CELEBREX™, or parecoxib or DYNASTAT™, or etoricoxib or ARCOXIA™ and optionally the anti-inflammatory therapy or anti-inflammatory therapy drug is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally opaganib, or YELIVA™, or opaganib, or YELIVA™ administered or formulated together with an oral and/or inhaled or aerosol chloroquine (or ARALEN™), chloroquine phosphate, chloroquine diphosphate and/or hydroxychloroquine (optionally, PLAQUENIL™)

and optionally the opaganib or YELIVA™ is formulated or administered at a dosage of QD (once a day), bid (twice a day) or tid (three times a day) at a dosage of between about 100 to 600 mg per day or per dosage, or at about 100, 200, 300, 400, 500 or 600 mg per day or per dosage, and optionally the opaganib, or YELIVA™ is also administered or formulated with an antibiotic (optionally azithromycin or doxycycline), ivermectin (optionally at 12 mg ivermectin, optionally administered on days 1, 3, 6 and 8), hydroxychloroquine (optionally, PLAQUENIL™) and/or zinc or any zinc salt (optionally zinc sulfate, optionally at (50 mg daily);

(tt) a calcium channel blocker, or verapamil (or ISOPTIN™, CALAN™), or a voltage gated potassium (KCNH2) channel or a voltage gated calcium channel (CACNA2D2) blocker, or amiodarone (or CORDARONE™, NEXTERONE™);

(uu) suramin, or ANTRYPOL™, BAYER 305™, or GERMANIN™;

(vv) a peroxisome proliferator-activated receptor (PPAR) agonist, wherein optionally the PPAR agonist comprises fenofibrate, or TRICOR™, FENOBRAT™, FENOGLIDE™, or LIPOFEN™, or a combination of fenofibrate and simvastatin, or CHOLIB™, optionally the PPAR agonist comprises a combination of fenofibrate and pravastatin, or PRAVAFENIX™, or the PPAR agonist comprises bezafibrate, or BEZALIP™, or combination of bezafibrate and chenodeoxycholic acid, or HEPACONDA™, or aluminium clofibrate, or alfibrate, or ciprofibrate, or clinofibrate or LIPOCLIN™, or clofibrate or ATROMID-S™, or clofibride, or gemfibrozil or LOPID™, or ronifibrate, or simfibrate or CHOLESOLVIN™, or any combination thereof, (ww) a synthetic nucleoside analog or derivative, or N4-hydroxycytidine, or a prodrug of N4-hydroxycytidine, optionally molnuvpiravir (Merck), or favipiravir (also known as T-705 or AVIGAN™, or favilavir, Toyama Chemical, Fujifilm, Japan, or FABIFLU™, Glenmark Pharmaceuticals), wherein the synthetic nucleoside analog or derivative, or N4-hydroxycytidine, or the prodrug of N4-hydroxycytidine, optionally molnuvpiravir or favipiravir, is given as between about 10 mg to 3 gm per dose, or between about 10 mg to 3 gm per day, or can be dosed either as a single dose or given one, two, three or four times a day, or is administered at 200 to 800 mg twice daily, or 200, 400, 600 or 800 mg twice daily, or at 200 to 800 mg three times a day, or at 200, 400, 600 or 800 mg three times a day, or is administered at 200 to 800 mg three times a day for between about 2 to 15 days, or for about 2, 3, 4, 5, 6, 7, 8, 9, 10, 11 or 12 days, and optionally when combined with other drugs a lower dosage is used, optionally administered at 100 or 200 mg three times a day for between about 5 to 15 days, or for about 7, 8, 9, 10, 11 or 12 days, and optionally the synthetic nucleoside analog or derivative, or N4-hydroxycytidine, or the prodrug of N4-hydroxycytidine, optionally molnuvpiravir or favipiravir, is administered with an avermectin class drug (optionally ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin), and optionally the synthetic nucleoside analog or derivative, or N4-hydroxycytidine, or the prodrug of N4-hydroxycytidine, optionally molnuvpiravir or favipiravir, is administered with an avermectin class drug (optionally ivermectin) with an antibiotic, and optionally the antibiotic comprises azithromycin, minocycline, amoxicillin, niclosamide, nitazoxanide, hydroxychloroquine or doxycycline), and optionally the synthetic nucleoside analog or derivative, avermectin class drug, and antibiotic are administered together or as separate formulations, and optionally are administered every one, two, three, four or five weeks for between about one month and one year or more;

and optionally molnuvpiravir, ivermectin and hydroxychloroquine are administered together or as separate formulations, and optionally are administered every one, two, three, four or five weeks for between about one month and one year or more;

and optionally the synthetic nucleoside analog or derivative (optionally N4-hydroxycytidine, or the prodrug of N4-hydroxycytidine, optionally molnuvpiravir or favipiravir), and antibiotic (optionally doxycycline or hydroxychloroquine) is administered with zinc (optionally a zinc sulphate, acetate, gluconate or picolinate, or zinc oxide nanoparticles, optionally at a dosage of between about 1 mg to 250 mg, or about 50 mg per day) and/or a vitamin, optionally vitamin C or D), and optionally the synthetic nucleoside analog or derivative, or N4-hydroxycytidine, or the prodrug of N4-hydroxycytidine, optionally molnuvpiravir or favipiravir, is administered with an antibiotic (optionally the antibiotic comprises azithromycin, minocycline, amoxicillin, niclosamide, nitazoxanide, hydroxychloroquine or doxycycline), optionally also administered with zinc (optionally a zinc sulphate, acetate, gluconate or picolinate, or zinc oxide nanoparticles, optionally at a dosage of between about 1 mg to 250 mg, or about 50 mg per day) and/or a vitamin, optionally vitamin C or D, and optionally any of these combinations is administered very 2, 3, 4, 5, 6, 7, 8, 9 or 10 or more days for between about 1 month and one year or more;

(xx) an antisera or an antibody or antibody or vaccine therapy for treating, preventing or ameliorating a microbial or a viral infection (optionally a coronavirus infection, optionally a COVID-19 infection) or a microbial infection (optionally a protozoan, helminthiasis, insect and/or parasitic infection), and optionally the antibody comprises a monoclonal antibody, and optionally the monoclonal antibody comprises sotrovimab (GlaxoSmithKline and Vir Biotechnology), or casirivimab, imdevimab or casirivimab and imdevimab (REGEN-COV™) (Regeneron), or bamlanivimab oretesevimab or bamlanivimab and etesevimab (Junshi Biosciences), or tocilizumab or ACTEMRA™ or ROACTEMRA™ (Hoffmann-La Roche), and optionally the vaccine comprises tozinamera or COMIRNATY™ (Pfizer), or elasomeran or SPIKEVAX™ (Moderna), or SPUTNIK V™ or Gam-COVID-Vac (Gamaleya Research Institute), or AZD1222 or COVISHIELD™ or VAXZEVRIA™ (Oxford-AstraZeneca), and optionally the antibody or antibody therapy comprises or is contained in a convalescent sera or plasma, and/or (yy) any combination of (a) to (xx), and optionally any one or several or all of (a) to (yy) with an (or formulated with or formulated as an) inhaled or aerosol formulation such as a powder or a mist or aerosol, and/or formulated with or formulated as an oral, intramuscular (IM) or intravenous (IV) formulation, wherein optionally both the inhaled (or aerosol) and the oral, IV and/or IM formulations are administered simultaneously or sequentially, and optionally the inhaled or aerosol formulation comprises chloroquine (or ARALEN™), chloroquine phosphate, chloroquine diphosphate and/or hydroxychloroquine (optionally, PLAQUENIL™) and/or oral chloroquine (or ARALEN™), chloroquine phosphate, chloroquine diphosphate and/or hydroxychloroquine (optionally, PLAQUENIL™) administered simultaneously or overlapping, and optionally the inhaled or aerosol formulation comprises an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and optionally any one or several or all of (a) to (yy), or any therapeutic combination of drugs or a drug, or a pharmaceutical dosage form as provided herein, are administered orally, intramuscularly, subcutaneously, topically, by use of an enema, intravaginally, or intravenously, or administration is by subcutaneous administration, sublingual administration, inhalation or by aerosol (optionally by inhalation of a liquid, an aerosol, a spray, a mist or a powder), by absorbable patch, by use of an implant, or by use of an enema or a suppository.

In alternative embodiments, the anti-viral drug or medication, or anti-microbial drug, is or comprises: molnupiravir, efavirenz (optionally, SUSTIVA™), tenofovir, emtricitabine and tenofovir, nevirapine (or the combination efavirenz with emtricitabine and tenofovir, or ATRIPLA™), amprenavir (optionally, AGENERASE™), nelfinavir (optionally, VIRACEPT™) and/or remdesivir (optionally, GS-5734™, Gilead Sciences), a viral RNA-dependent RNA polymerase inhibitor, optionally galidesivir, and optionally the anti-viral drug or medication is or comprises an anti-retroviral drug or drug combination, and optionally the anti-retroviral drug or drug combination comprises: darunavir and cobicistat (optionally, REZOLSTA™ or PREZCOBIX™); atazanavir (or REYATAZ™) and cobicistat (or EVOTAZ™); a nucleoside analog reverse-transcriptase inhibitor (NRTI) (optionally abacavir, or ZIAGEN™), lamivudine and dolutegravir (TRIUMEQ™); tenofovir (or disoproxil or emtricitabine) and elvitegravir and cobicistat (optionally, STRIBILD™); tenofovir (or disoproxil or emtricitabine) and elvitegravir and cobicistat (COMPLERA™ or EVIPLERA™); molnupiravir, efavirenz (optionally, SUSTIVA™), emtricitabine and tenofovir (ATRIPLA); lamivudine, nevirapine and stavudine (optionally, TRIOMUNE™); atazanavir (or REYATAZ™) and cobicistat (optionally, EVOTAZ™); lamivudine and raltegravir (optionally, DUTREBIS™); lamivudine and dolutegravir (or DOVATO™); doravirine, lamivudine and tenofovir (optionally, DELSTRIGO™); or lamivudine, zidovudine and nevirapine (optionally, CUOVIR-N™);

and optionally the additional anti-viral drug or medication, or anti-microbial drug, is formulated with the chloroquine (optionally, ARALEN™), chloroquine phosphate, chloroquine diphosphate, hydroxychloroquine (optionally, PLAQUENIL™), lopinavir, ritonavir (or NORVIR™) and/or oseltamivir or is formulated separately from the chloroquine (optionally, ARALEN™), chloroquine phosphate, chloroquine diphosphate, hydroxychloroquine (optionally, PLAQUENIL™), lopinavir, ritonavir (or NORVIR™) and/or oseltamivir, and optionally the anti-viral drug or medication, or anti-microbial drug, or palliative agent comprises or further comprises: magnesium (Mg, optionally administer intravenously (IV) to maintain a blood concentration of between about 2.0 and 2.4 mmol/1); zinc or any zinc salt (optionally a zinc sulphate, acetate, gluconate or picolinate, optionally administered at about 75 to 100 mg/day or at a dosage of between about 1 mg to 250 mg); at least one vitamin, wherein optionally the at least one vitamin comprises vitamin K, vitamin D or calcifediol (optionally D2 (or ergocalciferol) or Vitamin D3 or cholecalciferol), optionally administered at about 1000 to 4000 ugm/day), vitamin B6 (or pyridoxine), vitamin B12, vitamin E, and/or vitamin C (optionally administered at 500 mg bid); a flavonoid, plant flavonol or quercetin optionally administered at between about 250 to 500 mg bid; atorvastatin, or LIPITOR™, SORTIS™ (optionally administered at between about 40 mg/day to 80 mg/day); or, melatonin, or CIRCADIN™, SLENYTO™ (optionally between about 6 to 12 mg a day, optionally, at night), any of which are optionally given enterally or parenterally.

In alternative embodiments, provided are kits comprising a vaccine and/or an attenuated and/or live causative agent of infection, and at least one antibiotic and/or anti-viral drug capable of killing a causative agent of the infection, or completely or partially inhibiting the ability of the causative agent of the infection to replicate or become infectious or cause pathology in an individual, as described herein or used in any method as provided herein, wherein optionally the kit comprises instructions for practicing a method as provided herein.

In alternative embodiments of methods and kits as provided herein, the
(i) 1R,2S,5S)-N-[(1S)-1-cyano-2-[(3S)-2-oxopyrrolidin-3-yl]ethyl]-3-[(2S)-3,3-dimethyl-2-(2,2,2-trifluoroacetamido)butanoyl]-6,6-dimethyl-3-azabicyclo[3.1.0]hexane-2-carboxamide, or a compound having the following structure and molecular weight:

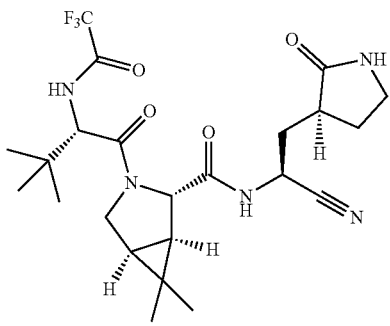

PF-07321332
C23H32F3N5O4
FW: 499.527 or stereoisomer, or enantiomer, or deuterated version thereof, and (ii) ritonavir, are formulated together, or separately, and optionally are formulated together or separately in or as a liquid (optionally to be administered as a drink or in drops, optionally as nasal drops or in a mist), a tablet, a capsule, a gel, a geltab, a powder, a lozenge, an aerosol or spray.

In alternative embodiments of methods and kits as provided herein, the anti-viral drug combination is formulated in or as a pharmaceutical dosage form, optionally formulated to be administered orally, intramuscularly, subcutaneously, topically, by use of an enema, intravaginally, or intravenously, or formulated for subcutaneous administration, sublingual administration, inhalation or by aerosol (optionally by inhalation of a liquid, an aerosol, a spray, a mist or a powder), by absorbable patch, by use of an implant, or by use of an enema or a suppository.

In alternative embodiments of methods and kits as provided herein, the
(a) 1R,2S,5S)-N-[(1S)-1-cyano-2-[(3S)-2-oxopyrrolidin-3-yl]ethyl]-3-[(2S)-3,3-dimethyl-2-(2,2,2-trifluoroacetamido)butanoyl]-6,6-dimethyl-3-azabicyclo[3.1.0]hexane-2-carboxamide, or a compound having the following structure and molecular weight:

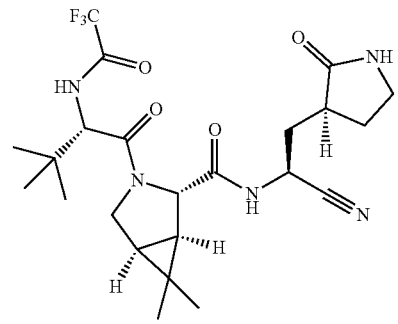

PF-07321332
C23H32F3N5O4
FW: 499.527 or stereoisomer, or enantiomer, or deuterated version thereof, and/or
(b) ritonavir,
is or are administered:
(a) at a dosage of QD (once a day), bid (twice a day) or tid (three times a day) at a dosage of between about 100 to 600 mg per day or per dosage, or at about 100, 200, 300, 400, 500 or 600 mg per day or per dosage, or
(b) at a dosage of between about 10 mg to 3 gm per dose, or between about 10 mg to 3 gm per day, or 12 mg or 3 mg/kg orally twice daily, or 125 mg orally twice daily or 520 mg/130 mg solution twice per day (optionally administered with efavirenz, fosamprenavir, nelfinavir, or nevirapine), or
(c) is dosed either as a single dose or given one, two, three or four times a day, or
(d) at 200 to 800 mg twice daily, or 200, 400, 600 or 800 mg twice daily, or at 200 to 800 mg three times a day, or at 200, 400, 600 or 800 mg three times a day, or is administered at 200 to 800 mg three times a day for between about 2 to 15 days, or for about 2, 3, 4, 5, 6, 7, 8, 9, 10, 11 or 12 days,
(e) for pediatric patients dosage at 16 mg or 4 mg/kg orally twice daily, or (f) when combined with other drugs a lower dosage, optionally administered at 100 or 200 mg three times a day for between about 5 to 15 days, or for about 7, 8, 9, 10, 11 or 12 days.

The details of one or more exemplary embodiments of the invention are set forth in the description below. Other features, objects, and advantages of the invention will be apparent from the description, and from the claims.

All publications, patents, patent applications cited herein are hereby expressly incorporated by reference in their entireties for all purposes.

DETAILED DESCRIPTION

In alternative embodiments, provided are methods for treating, ameliorating, decreasing the chances of having any adverse effects from, decreasing the severity of adverse effects from, or preventing an infection in an individual in need thereof, including humans and animals, by administration of an antibiotic and/or an anti-viral drugs and a vaccine directed to a causative agent of the infection, and/or an inactivated or attenuated causative agent of the infection, or the live, viable or infectious causative agent of the infection. In alternative embodiments, the infection (or causative agent of the infection) is parasitic, bacterial or viral. In alternative embodiments, the viral infection is a coronavirus infection such a Covid-19 infection.

In alternative embodiments, methods as provide herein prevent or decrease the prevalence or severity of "vaccine breakthrough infections" after vaccination, where external mutants of the infection's causative agent develop and infect or re-infect patients in spite of the fact that they have undergone immunization, for example, to prevent a Covid-19 infection. Thus, in alternative embodiments, methods as provided herein comprise combining an effective anti-microbial (for example anti-viral) treatment (for example, a drug or a mixture of drugs or other therapeutics) with an anti-microbial vaccine to prevent in vivo mutations (and thus also prevent a vaccine breakthrough infection) of an infectious agent such as virus, for example, a coronavirus such as COVID-19 or variant thereof.

In alternative embodiments, methods as provide herein provide a solution to the problem of imperfect vaccine disease prevention, where a bigger and/or better vaccine or multiple vaccinations are ineffective because science will never keep up with the continuing viral mutations. In alternative embodiments, methods as provide herein prevent replication of newly-inhaled mutants in the already vaccinated or 'about to be vaccinated' population.

In alternative embodiments, methods as provide herein comprise an added anti-replication method of treatment in addition to vaccination to protect the immunized population from mutants entering, replicating, and further mutating in the immunized population. In alternative embodiments, methods as provide herein prevent replication and thus prevent an ongoing viral mutation, a method utilized by the mutant to escape neutralizing antibodies and destruction. No replication, no mutation.

In alternative embodiments, methods as provide herein comprise combining an effective anti-microbial (for example anti-viral) treatment (for example, a drug or a mixture of drugs or other therapeutics) with an anti-microbial vaccine such as a DNA vaccine such as an adenovirus-based vaccine, an mRNA vaccine, a peptide-based vaccine, an inactivated pathogen-based vaccine, and/or an vaccine manufactured by:

Sanofi (optionally VAT00002 or VAT00008),
GlaxoSmithKline,
Takeda Pharmaceutical (optionally TAK-019),
Pfizer (optionally tozinamera or COMIRNATY™),
Moderna (optionally elasomeran or SPIKEVAX™)
Novavax (optionally vaccine to SARS VLPs S protein and influenza M1 protein),
CanSino Biologics,
Inovio,
Sinovac,
BioNTech,
Johnson and Johnson,
Valneva (France) and Dynavax Technologies (optionally VLA2001 and VLA2101),
Sinopharm (or China National Pharmaceutical Group Corporation),
Emergent BioSolutions (optionally human polyclonal hyperimmune serum with antibodies to SARS-CoV-2),
Bharat Biotech (optionally COVAXIN®),
The Rockefeller University (optionally vaccine toMVA S alone, or MVA-S prime and Ad5-S boost),
Helmholtz Centre for Infection Research; Technical University Munich; German Center for Environmental Health (optionally vaccine to NC protein add-mixed with MALP-2 by intranasal route and boosting with MVA-NC by intramuscular route),
University of Manitoba; University of Pennsylvania School of Medicine; Southern Research Institute; Fox Chase Cancer Institute (optionally vaccine to Heterologous Adenoviral prime boost AdHu5 s AdC7-nS),
University of North Carolina at Chapel Hill, USA (optionally vaccine to VEEV replicon particles expressing the SARS-CoV S),
National Institute of Infectious Diseases, Japan (optionally vaccine to recombinant D1 expressing S protein),
Beijing Institute of Genomics, China (optionally vaccine to Recombinant tructuated S—N fusion protein),
Saitama Medical University; Josai University; Nippon Oil and Fat Corporation; National Institute of Infectious Diseases, Japan (optionally vaccine to recombinant peptide N223 on liposomes),
Chinese Center for Disease Control and Prevention; Canadian Science Centre for Human and Animal Health (optionally vaccine to Recombinant TM-truncated S protein),
HKU-Pasteur Research Centre; The University of Hong Kong; National Institutes of Health; Centers for Disease (optionally vaccine to Trimeric Spike protein),
Sun Yat-sen University, China (optionally vaccine to SARS S DNA prime and HLAA*0201 restricted peptides boost vaccine),
State Key Laboratory of Virology; Graduate University of Chinese Academy of Sciences (optionally vaccine to or as a 3a DNA vaccine),
Institute of ImmunoBiology, Shanghai Medical College of Fudan University, China (optionally vaccine to DNA prime—protein S437-459 and M1-20),
CNB-CSIC; University of Iowa (optionally vaccine to rSARSCoV-E),
International Vaccine Institute (IVI) (optionally vaccine to recombinant adenovirus expressing truncated S protein (rADV-S)),
University Health Network, Canada, and United States Center for Disease Control and Prevention (CDC) (optionally vaccine to recombinant measles virus spike protein), Institut Pasteur (optionally vaccine to MV-SARS recombinant measles virus vaccine expressing SARS CoV antigen), Baylor College Medicine; Sabin; New York Blood Center (NYBC); University of Texas Medical Branch (UTMB); Walter Reed Army Institute of Research (WRAIR); National Institute of Allergy and Infectious Diseases (NIAID) (optionally vaccine to receptor binding domain (RBD) of the SARS-CoV spike (S) protein), Vaxine Pty Ltd, Australia (optionally vaccine to SARS recombinant spike protein plus delta inulin), Gamaleya Research Institute (optionally SPUTNIK V™ or Gam-COVID-Vac), and/or Oxford-AstraZeneca (optionally AZD1222 or COVISHIELD™ or VAXZEVRIA™)

and others, including anti-COVID-19 vaccines.

Hence, methods as provided herein that combine antibiotic, anti-parasitic and/or anti-viral treatment with an inactivated or attenuated causative agent of an infection, or a vaccine or a live, viable or infectious causative agent of the infection (for example, a live or attenuated virus) administration, can treat, ameliorate or prevent a vaccine-breakthrough infection, as well as eradicating the infection if present pre-vaccination enhance protection and eradicate infection.

In alternative embodiments, methods as provide herein comprise administering in coordination with (for example, before, during and/or after) an anti-causative agent vaccination, or an anti-viral vaccination, and/or the inactivated or attenuated causative agent of the infection, or the live, viable or infectious causative agent of the infection (such as a live or attenuated virus) administration, any one or combination of anti-viral, anti-parasitic or anti-bacterial therapies, for example, one or more anti-COVID-19 infection medications or drugs, including for example, the drug ivermectin, or the combination of ivermectin and an antibiotic with anti-viral properties such as doxycycline or azithromycin, for example the combination of ivermectin and doxycycline or azithromycin, or the combination ivermectin and doxycycline or azithromycin and zinc or any zinc salt (an anti-viral mineral, for example, and anti-COVID-19 mineral), which optionally also can be administered in conjunction or coordination with a vitamin or vitamins such as vitamin D and/or vitamin C.

In alternative embodiments, a drug combination administered in coordination with a vaccine and/or the inactivated or attenuated causative agent of the infection, or the live, viable or infectious causative agent of the infection (optionally a live or attenuated virus) administration comprises the commencement, optionally orally or by inhalation, of the antiviral combination before, or just before, and/or the day (day zero) the vaccine and/or the inactivated or attenuated causative agent of the infection, or the live, viable or infectious causative agent of the infection (such as a live or attenuated virus) administration is given. For example, in alternative embodiments, the patient (or individual in need thereof) is given a pre-vaccine drug or anti-viral treatment for between about 1 to 10 days, or between about 2 to 21 days, depending on dosing and conditions. If the patient is already infected but asymptomatic, because of this pre-vaccination (or pre-administration of the attenuated and/or the live infectious causative agent) treatment the patient will be free, or substantially free, of the infection but not yet endowed with complete or partial immunity. In other words, because of this pre-vaccination treatment there will be no virus, or substantially no virus, to replicate in vivo after the anti-viral treatment. After administration of the anti-microbial drug or treatment (optionally, 1, 2, 3, 4, 5, 6, 7, 8, 9, 10, 11, 12, 13 or 14 or more days after a first anti-microbial drug or treatment is first administered) the vaccine is given (depending on the type of vaccine, this may be the first of a two or three injection process). In alternative embodiments, after the first dose of the vaccine or the inactivated or attenuated causative agent of the infection, or the live, viable or infectious causative agent of the infection is given, the patient is treated at day 14 (or, optionally, on day 1, 2, 3, 4, 5, 6, 7, 8, 9, 10, 11, 12, 13 or 14) with an antibiotic or antiviral, for example, with a single preventative ivermectin and antibiotic drug combination (for example, using an antibiotic with anti-viral activity such as doxycycline or azithromycin), or ivermectin and doxycycline drug combination, or ivermectin and doxycycline and zinc drug combination, or ivermectin and azithromycin and zinc or any zinc salt, or any of these combinations with additional drugs or agent or adjuncts such as one or more vitamins, for example, vitamin B, C and/or D. In alternative embodiments, the drug combination administration is repeated every 14 days (or, optionally, every 1, 2, 3, 4, 5, 6, 7, 8, 9, 10, 11, 12, 13 or 14 or more days) for several weeks until plasma ivermectin is detectable over the 14 days. In alternative embodiments, later, the drug combination administration is repeated every 1, 2, 3, 4, 5 or 6 weeks or more.

In alternative embodiments, a second dose of the vaccine and/or the inactivated or attenuated causative agent of the infection, or the live, viable or infectious causative agent of the infection, and optionally subsequent boosters, are carried out between the intermittent (for example, every 1, 2, 3, 4, 5, 6, 7, 8, 9, 10, 11, 12, 13, 14 or up to 28 days) anti-microbial (for example, anti-viral) doses.

In alternative embodiments, combining vaccine or the inactivated or attenuated causative agent of the infection, or the live, viable or infectious causative agent of the infection with initial then intermittent anti-microbial (for example, anti-viral) administrations as provided herein achieves:

virtual 100%, or substantial (for example, 95% or more) infectious agent (for example, COVID-19) abolition or in vivo clearance, which can be achieved by the anti-microbial (for example, anti-viral) pre-vaccination treatment arm of methods as provided herein;

prolonged immunity, which can be achieved by administration of combined vaccine and intermittent anti-microbial (for example, anti-viral) treatments as provided herein;

lack of novel virus replication in the patient, which can be achieved by the anti-microbial (for example, anti-viral) pre-vaccination treatment arm of methods as provided herein;

no in vivo infectious agent (for example, virus) mutation in treated patients, as there is no or substantially no (for example, 90% to 99% reduction in) replication;

no 'Long Covid Syndrome', because if there is no infectious agent (or substantially no infectious agent) remaining in the patient in vivo, then can be no "Long Covid Syndrome";

no or minimal hospitalization, and no or substantially decreased number of deaths from Covid-19, because if there is no active in vivo infection there can be no progression to morbidity or mortality;

inability or substantial decrease in risk for patients treated using the combination methods as provided herein catch or be re-infected with any strain nor any mutant strain, where patients administered methods as provided herein are induced to have combined immunity (by administration of a vaccine) and an anti-viral response induced by administration of a drug or drugs which are viral mutant agonists;

eradication of primary viral (for example, COVID-19) infection, because patients administered methods as provided herein receive anti-microbial (for example, anti-viral) treatment at the beginning of therapy; and/or, ideal long-term preventative therapy for the elderly with senescent immunity by supporting waning antibody levels in the elderly patient with anti-microbial (for example, anti-viral) treatment as provided herein; and also in embodiments where ivermectin is administered, having the added benefit of rosacea improvement and prevention of scabies in aged-care facilities.

Increasing the dose of the intermittent ivermectin combination increases its anti-Covid-19 preventative power. In alternative embodiments, the dose is raised from between about 12 mg to about 36 mg, about 48 mg or about 60 mg, or the dose is raised progressively to 120 mg with few if any adverse effects. This will create a more prolonged circulating level. This is expected to be close to 100% at 4 weeks, but when combined with the vaccine could well prevent for up to 6 weeks or more. Hence, creating the possibility of reducing dosing to ×7/year. Given the use of accompanying anti-viral drugs, even if the vaccine results in lower circulation of neutralizing antibody levels and so immunity, the risk of vaccine breakthrough infection will be minimal if at all possible. Hence, this combination of anti-viral treatment together with the vaccine would be ideal therapy for prevention of infection in the elderly population with senescent immune systems.

In alternative embodiments, any vaccine will benefit from practicing methods as provided herein, particularly the mRNA vaccines, which will benefit profoundly when combined with an effective anti-viral treatment.

In alternative embodiments, methods as provided herein comprise 1 to 10 days of treatment with an ivermectin-based (or ivermectin-comprising) combination, followed by (the first dose of) vaccination, and then every 1, 2, 3, 4, 5, 6 or 7 days, and later every 8, 9, 10, 11, 12, 13 or 14 days (for example, every 7 days, then every 14 days), and later to 15, 16, 17, 18, 19, 20, 21, 22, 23, 24, 25, 26, 27 or 28 days (for example, every 7 days, then every 14 days, and later every 28 days), administer a higher dose of ivermectin, for example, 60 mg ivermectin for 4 weeks together with zinc or a zinc salt, doxycycline, vitamin D and vitamin C or other appropriate combinations. As long as one continues the anti-viral treatment based on the 60 mg ivermectin regimen, a vaccinated patient has both circulating antibodies for many months and cannot catch mutated virus (for example, COVID-19 agents), and therefore "vaccine breakthrough" will be prevented or substantially decreased and super infection with mutants will be prevented or substantially decreased.

In alternative embodiments, methods as provided herein, including for example the ivermectin, zinc or a zinc salt and doxycycline and optionally also an adjunct therapy (such as for example administering a vitamin such as vitamin C or D) is mutant agnostic. In alternative embodiments, because methods as provided herein, including for example the ivermectin combination therapy, functions and works using a different mechanism by prevention of replication within a cell, no mutants can affect its activity as has been shown by us in clinical practice in California, United States. Hence, the combination of an anti-viral with a vaccine as provided herein may be the best method of terminating the Covid-19 pandemic.

In alternative embodiments, the vaccination or the inactivated or attenuated causative agent of the infection, or the live, viable or infectious causative agent of the infection administration may need to be repeated, for example, repeated at 6 or 12 month (or between about 1 (monthly) to 12 month) intervals, but it is of no great importance whether it is 6 months or 12 months because the second arm or the therapy as provided herein, the anti-viral arm, is on board to prevent any further infection and therefore any further mutation in vivo in the patient.

In alternative embodiments, even if a mutant or variant strain becomes the predominant viral agent in a community in the future necessitating that the vaccine and/or the inactivated or attenuated causative agent of the infection, or the live, viable or infectious causative agent of the infection be adjusted (or changed) to take in (be specific for) that new mutant or variant strain, the drug combination as provided herein, for example, the ivermectin, zinc or a zinc salt and doxycycline plus adjunct treatment, can remain the same as it is mutant agnostic. Hence, any vaccine produced by any institution can be supplemented with an anti-viral combination such that no individuals will catch any viral strains once the individual has begun this program (commenced receiving treatment regimens as provided herein.

The concept of 'redundancy' of treatment is significant here; in medicine, redundant treatment is one where the medication carries extra power to cure the condition. In the event that the treatment had to be terminated early (for example, due to an allergy developing) the built-in redundancy still delivers near (substantially) 100% cure because it was designed to carry extra power. Hence, the combination of the anti-viral treatment and vaccination as provided herein carries a high level of redundancy and thus can achieve a close to 100% success rate (or a substantially completely successfully cure rate).

Although alternative embodiments of methods as provided herein are best suited to prevent and treat a virus such as a coronavirus such as a Covid-19 infection, alternative embodiments have multiple other applications. For example, in alternative embodiments, with appropriate antivirals methods as provided herein are used to prevent influenza infections. In alternative embodiments, provided are methods comprising a treatment regimen of an influenza (or other viral) vaccine followed later by antiviral agents intermittently in once a week, 2 weekly, 3 weekly, 4 weekly or less frequently spaced intervals to prevent influenza mutants from re-infecting de novo susceptible elderly patients with senescent immune system where influenza infection causes the most mortality. Other exemplary antiviral combinations administered practicing methods as provided herein comprise use of hydroxychloroquine, for example, hydroxychloroquine, azithromycin and zinc or a zinc salt.

In alternative embodiments, provided are methods comprising a treatment regimen for treating: dengue fever, Zika, HIV, hepatitis C, Ebola disease, SARS, MERS, polio, measles, chickenpox and other viral or retro-viral infections. Where current immunizations may not be adequately effective, the follow-on with intermittent antiviral therapy as provide by methods as provided herein gives extra power for the poor immune response combined with antivirals to have enough redundancy to make it clinically effective.

In alternative embodiments, provided are methods comprising use of antiviral compounds used singly or in multiple combinations, for example, antiviral compounds are administered singly or in multiple combinations, for example, before, at the time of vaccination, and/or after vaccination:

For example, in alternative embodiments, methods provided herein comprise administering in coordination with (optionally before, at the time of vaccination, and/or after vaccination of) an anti-microbial vaccine a single drug or a therapeutic combination of drugs, or a single drug, a pharmaceutical dosage form, a drug delivery device, or a product of manufacture, or the methods can comprise use of: one, two or more classes of antiviral drugs used against influenza, such as: M2 protein inhibitors (for example, amantadine and rimantadine); neuraminidase inhibitors (for example, oseltamivir, zanamivir, peramivir and laninamivir); favipiravir (also known as T-705 or AVIGAN™, or favilavir, Toyama Chemical, Fujifilm, Japan, or FABIFLU™, Glenmark Pharmaceuticals); a 5- to 6-membered heterocyclic ring such as benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline; amantadine; rimantadine; oseltamivir; zanamivir; peramivir; laninamivir; laninamivir octanoate hydrate; arbidol; ribavirin; stachyflin; ingaviri; fludase; a niclosamide compound; an emricasan compound; nitazoxanide; tizoxanide; and/or a compound selected from consisting of teriflunomide, hydroxocobalamin, ensulizole, tenonitrozole, isoliquiritigenin, nitazoxanide, febuxostat, leflunomide, fidofludimus SB-366791, emodin, diphenyl isophthalate, benzoylpas, fenobam, indobufen, 2-(2H-Benzotriazol-2-yl)-4-methylphenol, tiaprofenic acid, flufenamic acid, vitamin B12, cinanserin, 5-nitro-2-(3-phenylpropylamino)benzoic acid, veliflapon, thiabendazole, SIB 1893, anethole trithione, naringenin, phenazopyridine, fanetizole, terazosin, diacerein, CAY10505, hesperetin, suprofen, ketorolac tromethamine, piperine, pirarubicin, piraxostat, albendazole oxide, tyrphostin AG 494, genistin, fenbufen, apatinib, RITA, BF-170 hydrochloride, OSI-930, tribromsalan, pifexole, formononetin, ebselen, tranilast, benzylparaben, 2-Ethoxyethyl-p-methoxycinnamate, baicalein, nemorubicin, rutaecarpine, 2-Methyl-6-(phenylethynyl) pyridine (MPEP), 5,7-dihydroxyflavone, vitamin B12, pipofezine, flurbiprofen axetil, 2-Amino-6-nitrobenzothiazole, nalachite green oxalate, enfenamic acid, fenaminosulf, AS-252424, phenserine, epalrestat, alizarin, dalcetrapib, SN-38, echinomycin, (S)-(+)-camptothecin, BI-2536, 10-hydroxycamptothecin, topotecan, delanzomib, volasertib, ispinesib, paclitaxel, FK-506, emetine, AVN-944, digoxin, vincristine, idarubicin, thapsigargin, lexibulin, ixazomib, cephalomannine, mitoxantrone, MLN-2238, demecolcine, vinorelbine, bardoxolone methyl, cycloheximide, actinomycin D, AZD-7762, PF-184, CHIR-124, cyanein, triptolide, KX-01, PF-477736, epirubicin, mycophenolate (mycophenolic acid), daunorubicin, PIK-75, vindesine, torin-2, floxuridine, Go-6976, OSU-03012, and a prodrug, metabolite, or derivative of any of the foregoing.

In alternative embodiments the following compound (or its isomer, or stereoisomer, or enantiomer, or deuterated version, or bioisostere) is used singly or in various combinations (for example, formulated with, or administered separately) with other drug such as anti-viral drugs before, during or after vaccination or administration of a causative agent of infection: (1R,2S,5S)-N-[(1S)-1-cyano-2-[(3S)-2-oxopyrrolidin-3-yl]ethyl]-3-[(2S)-3,3-dimethyl-2-(2,2,2-trifluoroacetamido)butanoyl]-6,6-dimethyl-3-azabicyclo[3.1.0]hexane-2-carboxamide administered orally or by inhalation (or nasally), for example, as liquid, solid, powder, mist or spray, which can target a protease (such as the 3CL protease in COVID-19) and optionally has the following structure and molecular weight:

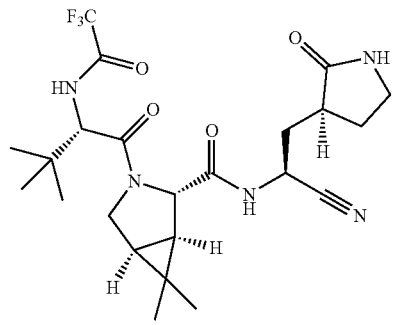

PF-07321332
C23H32F3N5O4
FW: 499.527

This protease inhibitor (PF-07321332, or PAXLOVID™) may be used alone before and after the vaccination and/or administration of the attenuated causative agent of infection, optionally administered with ritonavir (or NORVIR™) or lopinavir, or with any of the numerous antiviral agents as provided herein.

In alternative embodiments the following compounds (or their isomers, or stereoisomers, or enantiomer, or bioisostere) can be used singly or in various combinations:

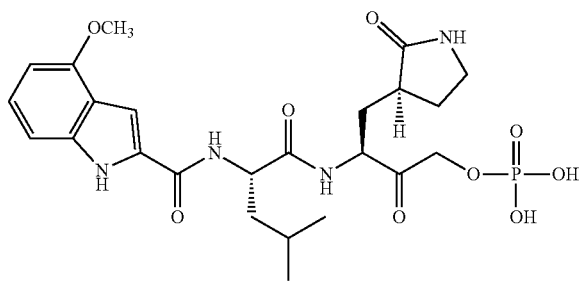

PF-07304814

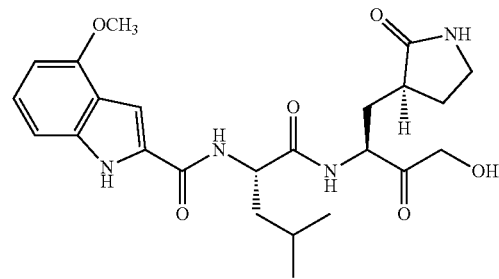

PF-00835231

These compounds (PF-07304814 and/or PF-00835231) (or its isomer, or stereoisomer, or enantiomer, or deuterated version, or bioisostere) may be used alone before and after the vaccination and/or administration of the attenuated causative agent of infection, optionally administered with ritonavir (or NORVIR™) or lopinavir, or with any of the numerous antiviral agents as provided herein.

In alternative embodiments, the PF-07321332 (or PAXLOVID™) and ritonavir (or NORVIR™) or lopinavir combination; or the PF-07304814 and/or PF-00835231 and ritonavir (or NORVIR™) or lopinavir combination; or the KALETRA™, ALTERA™, ALUVIA™, KALMELTREX, LOPIMUNE™ or LOPINAVIR™ and/or zanamivir (or RELENZA™) combination; is administered separately, or together (for example, formulated together) as a tablet, gel, geltab or capsule, as a powder, in a liquid, in a mist or a spray, or as a lozenge. In alternative embodiments, the PE-07321332 (or PAXLOVID™) and ritonavir (or NOR-VIR™) or lopinavir combination; or the PF-07304814 and/or PF-00835231 and ritonavir (or NORVIR™) or lopinavir combination; or the KALETRA™, ALTERA™, ALUVIA™, KALMELTREX, LOPIMUNE™ or LOPINAVIR™ and/or zanamivir (or RELENZA™) combination; is administered before, at the same time as, and/or after the vaccination.

In alternative embodiments, the PF-07321332 (or PAXLOVID™) and ritonavir (or NORVIR™) or lopinavir combination; or the PF-07304814 and/or PF-00835231 and ritonavir (or NORVIR™) or lopinavir combination; or the KALETRA™, ALTERA™, ALUVIA™, KALMELTREX, LOPIMUNE™ or LOPINAVIR™ and/or zanamivir (or RELENZA™) combination; is administered 1, 2, 3, 4, 5, 6, 7, 8, 9, 10, 11, 12, 13 or 14 or more days before, and/or on the day of, a first dose of the at least one of a plurality of dosages of the vaccine is administered, or a dose of the inactivated, attenuated, or the live, viable or infectious causative agent of the infection is administered.

In alternative embodiments, the PF-07321332 (or PAXLOVID™) and ritonavir (or NORVIR™) or lopinavir combination; or the PF-07304814 and/or PF-00835231 and ritonavir (or NORVIR™) or lopinavir combination; or the KALETRA™, ALTERA™, ALUVIA™, KALMELTREX, LOPIMUNE™ or LOPINAVIR™ and/or zanamivir (or RELENZA™) combination; is administered 1, 2, 3, 4, 5, 6, 7, 8, 9, 10, 11, 12, 13 or 14 or more days after a first dose of the at least one of a plurality of dosages of the vaccine is administered, or a dose of the inactivated, attenuated, or the live, viable or infectious causative agent of the infection is administered.

In alternative embodiments, the PF-07321332 (or PAXLOVID™) and ritonavir (or NORVIR™) or lopinavir combination; or the PF-07304814 and/or PF-00835231 and ritonavir (or NORVIR™) or lopinavir combination; or the KALETRA™, ALTERA™, ALUVIA™, KALMELTREX, LOPIMUNE™ or LOPINAVIR™ and/or zanamivir (or RELENZA™) combination; is administered both before and after a first dose of the at least one of a plurality of dosages of the vaccine is administered, or a dose of the inactivated, attenuated, or the live, viable or infectious causative agent of the infection is administered. Another agent which can be used singly or in combination before and accompanying vaccination is 2-deoxy-D-Glucose (2-DG).

In alternative embodiments, methods as provided herein comprise (or further comprise) administering in coordination with (optionally before, at the time of vaccination, and/or after vaccination of) an anti-microbial vaccine (or a dose of the inactivated, attenuated, or the live, viable or infectious causative agent of the infection) a therapeutic combination of drugs or a single drug, a pharmaceutical dosage form, a drug delivery device, or a product of manufacture, comprising:

(a) a thiazolide class drug, optionally nitazoxanide (or ALINIA™, NIZONIDE™) or tizoxanide (or 2-Hydroxy-N-(5-nitro-2-thiazolyl)benzamide);

(b) molnupiravir, optionally co-administered with and/or formulated with an avermectin class drug (optionally ivermectin), an antibiotic (optionally doxycycline or azithromycin) and/or zinc, or co-administered with and/or formulated with ivermectin, hydroxychloroquine, an antibiotic (optionally doxycycline or azithromycin) and/or zinc; (c) opaganib or YELIVA™, or opaganib or YELIVA™ and oral and/or inhaled or aerosol chloroquine (or ARALEN™), chloroquine phosphate, chloroquine diphosphate, amodiaquine (or AMDAQUINE™, AMOBIN™) and/or hydroxychloroquine (optionally, PLAQUENIL™), wherein optionally each or both of the opaganib and the chloroquine (or ARALEN™) chloroquine phosphate, chloroquine diphosphate and/or hydroxychloroquine (optionally, PLAQUENIL™) are in or formulated as a formulation for inhalation, for example, formulated as an aerosol, spray, mist, liquid or powder, or each or both are formulated for oral, intramuscular or intravenous administration, wherein optionally the opaganib is administered at a dosage of QD (once a day), bid (twice a day) or tid (three times a day) at a dosage of between about 100 to 600 mg per day or per dosage, or at about 100, 200, 300, 400, 500 or 600 mg per day or per dosage, and optionally the opaganib, or YELIVA™ is also administered or formulated with an antibiotic (optionally azithromycin or doxycycline), ivermectin (optionally at 12 mg ivermectin, optionally administered on days 1, 3, 6 and 8), hydroxychloroquine (optionally, PLAQUENIL™) and/or zinc (optionally zinc sulfate, optionally at (50 mg daily, or any zinc salt);

(d) lopinavir, ritonavir (or NORVIR™) and oseltamivir (optionally, TAMIFLU™), and/or zanamivir (or RELENZA™);

(e) lopinavir combined (formulated) with ritonavir (or NORVIR™), or KALETRA™, ALTERA™, ALUVIA™, KALMELTREX, LOPIMUNE™ or LOPINAVIR™, and/or zanamivir (or RELENZA™), or lopinavir and ritonavir separately formulated;

(f) lopinavir combined (formulated) with ritonavir (or NORVIR™) (or KALETRA™, ALTERA™, ALUVIA™, KALMELTREX, LOPIMUNE™ or LOPINAVIR™), or lopinavir and ritonavir (or NORVIR™), and oseltamivir (optionally, TAMIFLU™), and/or zanamivir (or RELENZA™), optionally also with inhaled or aerosol formulations or versions of chloroquine (or ARALEN™), amodiaquine (or AMDAQUINE™, AMOBIN™), chloroquine phosphate, chloroquine diphosphate and/or hydroxychloroquine (optionally, PLAQUENIL™) and/or oral chloroquine (or ARALEN™), chloroquine phosphate, chloroquine diphosphate and/or hydroxychloroquine (optionally, PLAQUENIL™) simultaneously;

(g) lopinavir, ritonavir (or NORVIR™), amodiaquine (or AMDAQUINE™, AMOBIN™), chloroquine and oseltamivir (or TAMIFLU™); wherein optionally the chloroquine comprises inhaled or aerosol chloroquine (or ARALEN™), chloroquine phosphate, chloroquine diphosphate and/or hydroxychloroquine (optionally, PLAQUENIL™) and/or oral chloroquine (or ARALEN™), chloroquine phosphate, chloroquine diphosphate and/or hydroxychloroquine (optionally, PLAQUENIL™) simultaneously;

(H) lopinavir and oseltamivir (optionally, TAMIFLU™), and/or zanamivir (or RELENZA™);

(i) ritonavir (or NORVIR™) and oseltamivir (optionally, TAMIFLU™), and/or zanamivir (or RELENZA™);

(j) remdesivir (optionally, GS-5734™, Gilead Sciences) alone, or oseltamivir (optionally, TAMIFLU™) and remdesivir (optionally, GS-5734™, Gilead Sciences), and optionally the remdesivir is an oral formulation and/or an inhaled or aerosol remdesivir formulation;

(k) oseltamivir (optionally, TAMIFLU™) and efavirenz (optionally, SUSTIVA™), and/or zanamivir (or RELENZA™);

(l) oseltamivir (optionally, TAMIFLU™) and nevirapine (or the combination efavirenz with emtricitabine and tenofovir, or ATRIPLA™);

(m) oseltamivir (or TAMIFLU™) and amprenavir (optionally, AGENERASE™);

(n) oseltamivir (optionally, TAMIFLU™) and nelfinavir (optionally, VIRACEPT™);

(o) a thiazolide class drug, optionally nitazoxanide (optionally ALINIA™, NIZONIDE™) or tizoxanide (or 2-hydroxy-N-(5-nitro-2-thiazolyl)benzamide), with or in combination with any of (a) to (nn), or any drug or drug combination as provided herein, optionally a thiazolide class drug, optionally nitazoxanide, with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin; or a thiazolide class drug (optionally, nitazoxanide or tizoxanide) and oseltamivir (or TAMIFLU™),
and optionally the thiazolide class drug (optionally, nitazoxanide or tizoxanide) is formulated or administered with ribavirin or tribavirin (or COPEGUS™, REBETOL™, or VIRAZOLE™), and an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin;

(p) plitidepsin (also known as dehydrodidemnin B), or APLIDIN™ (PharmaMar, S. A.);

(q) an inhibitor or S-phase kinase-associated protein 2 (SKP2), or dioscin, or niclosamide, or NICLOCIDE™, FENASAL™, or PHENASAL™;

(r) ritonavir (or NORVIR™), ribavirin or tribavirin (or COPEGUS™, REBETOL™, or VIRAZOLE™), interferon beta 1b, or a combination of ribavirin and interferon beta, or a combination of lopinavir and ritonavir (or NORVIR™) and interferon-beta-1b;

(s) a nucleoside analog reverse-transcriptase inhibitor (NRTI) (optionally abacavir, or ZIAGEN™), acyclovir or aciclovir (optionally ZOVIRAX™), adefovir (optionally HEPSERA™), amantadine(optionally GOCOVRI™, SYMADINE™, SYMMETREL™), rintatolimod (or AMPLIGEN™), amprenavir (optionally, AGENERASE™), aprepitant (or EMEND™), umifenovir (or ARBIDOL™), atazanavir (or REYATAZ™), atazanavir (or REYATAZ™), tenofovir, a combination of efavirenz and emtricitabine and tenofovir (or ATRIPLA™), balavir, baloxavir marboxil (XOFLUZA™), bepotastine, bevirimat, bictegravir, a combination of bictegravir and emtricitabine and tenofovir alafenamide (or BIKTARVY™), brilacidin, bivalirudin (or BIVALITROBAN™), cidofovir, caspofungin, lamivudine and zidovudine (optionally, COMBVIR™), cobicstat, colisitin, cocaine, darunavir, delavirdine, descovy, didanosine, docosanol, dolutegravir, ecoliever, edoxudine, efavirenz (optionally, SUSTIVA™), elvitegravir, emtricitabine, enfuvirtide, foscarnet, fosfonet, galidesivir, ibacitabine, icatibant, idoxuridine, ifenprodil, imiquimod, imunovir, indinavir, inosine, an interferon (optionally interferon type I, interferon type II and/or interferon type III), lamivudine (or EPIVIR™, ZEFFIX™), lopinavir, loviride, ledipasvir, leronlimab, maraviroc, methisazone, moroxydine, nelfinavir, nevirapine, nexavir, nitazoxanide (optionally ALINIA™, NIZONIDE™), norvir, a nucleoside analogue or derivative (optionally brincidofovir (or TEMBEXA™), didanosine (or VIDEX™), favipiravir (also known as T-705 or AVIGAN™, or favilavir, Toyama Chemical, Fujifilm, Japan, or FABIFLU™, Glenmark Pharmaceuticals), vidarabine, galidesivir (optionally, BCX4430, IMMUCILLIN-A™), remdesivir (optionally, GS-5734™, Gilead Sciences), cytarabine, gemcitabine, emtricitabine, lamivudine, zalcitabine, entecavir, stavudine, telbivudine, zidovudine, idoxuridine and/or trifluridine or any combination thereof), oseltamivir (or TAMIFLU™), peginterferon alfa-2a, penciclovir, peramivir (optionally, RAPIVAB™), perfenazine, pleconaril, plurifloxacin, podophyllotoxin, pyramidine, raltegravir, rifampicin, ribavirin or tribavirin (or COPEGUS™, REBETOL™, or VIRAZOLE™), rilpivirine, rimantadine, ritonavir (or NORVIR™), saquinavir, sofosbuvir, stavudine, telaprevir, tegobuv, tenofovir alafenamide, tenofovir disoproxil, tenofovir, tipranavir, trifluridine, trizivir, tromantadine, truvada, valaciclovir (optionally, VALTREX™), valganciclovir, valrubicin, vapreotide, vicriviroc, vidarabine, viramidine, velpatasvir, vivecon, zalcitabine, zanamivir (optionally, RELENZA™), zidovudine, an immunosuppressive drug (optionally tocilizumab or atlizumab, or ACTEMRA™, or ROACTEMRA™) or any combination thereof;

(t) a mucolytic therapy or drug, optionally acetylcysteine, ambroxol, bromhexine (or BISOLVON™), carbocisteine, erdosteine, mecysteine or dornase alfa, or an expectorant, optionally guaifenesin;

(u) a viral, or a coronavirus or a COVID-19, protease inhibitor, optionally ASC09 (CAS registry no. 1000287-05-7) (Janssen Research and Development, LLC), ritonavir (or NORVIR™) or ASC09 and ritonavir (or NORVIR™), or a JAK1/2 inhibitor (optionally baricitinib), optionally compound 11r (University of Lubeck, Germany, see optionally, Zhang et al J. Med Chem 2020, Feb. 11, 2020), or darunavir, cobicistat or darunavir and cobicistat;

(v) an angiotensin-converting enzyme 2 (ACE2) inhibitor, optionally to block the site of viral spike protein interaction for anti-SARS-CoV-2 infection control;

(w) an anti-vascular endothelial growth factor (VEGF) (optionally VEGF-A) drug or antibody, optionally bevacizumab;

(x) a protease inhibitor, optionally danoprevir, optionally a serine protease inhibitor, optionally camostat or narlaprevir (optionally ARLANSA™);

(y) anti-PD-1 checkpoint inhibitor, optionally camrelizumab;

(z) a compound or antibody capable of binding complement factor C5 and blocking membrane attack complex formation, optionally eculizumab;

(aa) a cathepsin inhibitor, optionally a cathepsin K, B or L inhibitor, optionally relacatib;

(bb) thalidomide, or thalidomide and glucocorticoid (optionally ciclesonide (or ALVESCO™, OMNARIS™, OMNIAIR™, ZETONNA™ or ALVESCO™)) (optionally low-dose glucocorticoid), or and thalidomide and celecoxib;

(cc) an antibacterial antibiotic or a macrolide drug,
wherein optionally the macrolide drug comprises azithromycin, optionally dosaged at between about 50 mg to about 2000 mg per dose or per day (optionally, ZITHROMAX™, or AZITHROCIN™, optionally an oral extended- or delayed-release formulation of azithromycin, or ZMAX™), clarithromycin (optionally, BIAXIN™), erythromycin (optionally, ERYTHROCIN™), or fidaxomicin (optionally, DIFICID™ or DIFICLIR™), troleandomycin (optionally, TEKMISIN™), tylosin (optionally, TYLOCINE™ or TYLAN™), solithromycin (optionally, SOLITHERA™), oleandomycin (or SIGMAMYCINE™), midecamycin, roxithromycin, kitasamycin or turimycin, josamycin, carbomycin or magnamycin, and/or spiramycin, and optionally the antibacterial antibiotic comprises a tetracycline class drug, a glycylcycline or a fluorocycline class drug, or an analogue thereof, and optionally the tetracycline, glycylcycline or fluorocycline drug or analogue thereof comprises or is: tetracycline or SUMYCIN™; chlortetracycline or AUREOMYCIN™; oxytetracycline; demeclocycline or DECLOMYCIN™, DECLOSTATIN™, LEDERMYCIN™, BIOTERCICLIN™, DEGANOL™, DETECLO™, DETRAVIS™, MECICLIN™, MEXOCINE™, CLORTETRIN™; lymecycline; meclocycline; metacycline; minocycline or MINOCIN™; rolitetracycline; doxycycline, or DORYX™, DOXYHEXA™, DOXYLIN™; tigecycline or TYGACIL™; eravacycline or XERAVA™; sarecycline or SEYSARA™, omadacycline or NUZYRA™; or any combination thereof, and optionally the antibacterial antibiotic or macrolide drug, optionally azithromycin (or ZMAX™), is administered in combination with, and/or is combined with, chloroquine (or ARALEN™), amodiaquine (or AMDAQUINE™, AMOBIN™), chloroquine phosphate, chloroquine diphosphate and/or hydroxychloroquine (optionally, PLAQUENIL™), and the combination is administered commencing on the first, second, third, fourth, fifth, sixth, seventh, eighth, ninth and/or tenth day of therapy, or is administered for 1, 2, 3, 4, 5, 6, 7, 8, 9, 10 or up to 20 or more days, or for between about 1 to 21 days or longer, or is administered until within 1, 2, 3, 4, 5, 6, 7, 8, 9, 10 or up to 20 or more days of ending the therapy for treating, preventing, ameliorating, slowing the progress of, decreasing the severity of or preventing the coronavirus infection, and optionally the chloroquine (or ARALEN™), chloroquine phosphate, amodiaquine (or AMDAQUINE™, AMOBIN™), chloroquine diphosphate and/or hydroxychloroquine (optionally, PLAQUENIL™) is administered the entire length of the treatment but the azithromycin, optionally dosaged at between about 50 mg to about 2000 mg per dose or per day (optionally, ZITHROMAX™, or AZITHROCIN™, optionally an oral extended-release formulation of azithromycin, or ZMAX™) administration is halted or ceased after two, three, four, five or six days after treatment is commenced, and optionally the azithromycin administration is replaced by a tetracycline class drug, and optionally the tetracycline class drug comprises doxycycline, or DORYX™, DOXYHEXA™, DOXYLIN™ administration, and optionally the antibacterial antibiotic, optionally azithromycin (optionally, ZITHROMAX™, or AZITHROCIN™, optionally dosaged at between about 50 mg to about 2000 mg per dose or per day, and optionally an oral extended-release formulation of azithromycin, or ZMAX™), is administered or formulated with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and/or cholecalciferol (vitamin D3) or calcifediol, and optionally the antibacterial antibiotic comprises an antimycobacterial drug, and optionally the antimycobacterial drug comprises clofazimine (optionally LAMPRENE™);

(dd) an avermectin class drug such as ivermectin (optionally STROMECTOL™, SOOLANTRA™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, optionally dosaged and/or administered at about 5 microgram/kg to about 1 gram (g) per day, optionally formulated or administered at about 1 to 10, 12, 15, 20, 30, 40, 50, 60, 70, 80, 100, 120, 140, 160, 180, 200, 220 or 240 mg per day, or between about 1 to 240 mg per day, or between about 3 to 240 mg per day, optionally formulated or administered with an antibiotic (optionally azithromycin, minocycline, amoxicillin, niclosamide, nitazoxanide, hydroxychloroquine or doxycycline, and optionally the doxycycline is at between about 25 to 600 mg per dose or per day, or at about 100 mg per dose or per day, and optionally the azithromycin is at between about 50 mg to 2000 mg per dose or per day), optionally as a single or a divided dose, and optionally formulated and administered as an inhalant or a mist (optionally using a nebulizer, nasal spray or equivalent), optionally formulated as an aerosol, spray, mist, liquid or powder, optionally formulated as an aerosol, spray, mist, liquid or powder, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is formulated with and/or administered with chloroquine (or ARALEN™), chloroquine phosphate, chloroquine diphosphate and/or hydroxychloroquine (optionally, PLAQUENIL™) with or without zinc (optionally a zinc sulphate, acetate, gluconate or picolinate or any zinc salt), and optionally this combination is administered weekly, or every two week, or one every 5 to 28 days, as a prophylactic, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered alone in the morning (AM), and an antibiotic (optionally doxycycline) and/or a chloroquine (optionally, ARALEN™), chloroquine phosphate, chloroquine diphosphate and/or hydroxychloroquine (optionally, PLAQUENIL™) is administered in the afternoon and/or evening, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered alone for 1, 2, 3, 4, 5, 6, 7, 8, 9, 10 or up to 20 or more days, followed by administration of an antibiotic (optionally doxycycline) for a corresponding period of days, and optionally repeating the cycle of dosaging, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is formulated or administered with:
  (i) at least one antibiotic (wherein optionally the antibiotic is doxycycline(optionally, DORYX™, DOXYHEXA™, DOXYLIN™) (optionally formulated or administered at a dosage of between about 25 mg to 600 mg per dose or per day), or azithromycin (optionally, ZITHROMAX™, or AZITHROCIN™, optionally dosaged at between about 50 mg to about 2000 mg per dose or per day, optionally an oral extended-release formulation of azithromycin, or ZMAX™) (optionally formulated or administered at a dosage of between an about 50 mg to 2000 mg);
  (ii) chloroquine (or ARALEN™), chloroquine phosphate, chloroquine diphosphate and/or hydroxychloroquine (optionally, PLAQUENIL™) (optionally formulated or administered at a dosage of between an about 10 mg to 2000 mg per day);
  (iii) a zinc (optionally a zinc sulphate, acetate, gluconate or picolinate or any zinc salt) optionally formulated or administered at a dosage of between about 1 mg to 250 mg; and/or
  (iv) at least one vitamin, and optionally the at least one vitamin comprises: vitamin C optionally formulated or administered at a dosage of between about 500 to 5000 units (U) per dose, and/or Vitamin D (or cholecalciferol) optionally formulated or administered at a dosage of between about 3,000 to 100,000 units per day, or between about 10,000 to 50,000 units a day, and optionally the avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin is administered or formulated alone or in combination with any of the above (i) to (iv) (for example, at least one antibiotic, chloroquine (or ARALEN™), chloroquine phosphate, chloroquine diphosphate and/or hydroxychloroquine (optionally, PLAQUENIL™), zinc or any zinc salt and/or at least one vitamin are formulated (and administered) as oral formulations (for example, as tablets, capsules, gels or geltabs), injectable formulations, powders (for example, for inhalation or for addition to an ingestible liquid) or liquids (for example, for ingestion, infusion or injection);

(ee) chloroquine (or ARALEN™), chloroquine phosphate, chloroquine diphosphate and/or hydroxychloroquine (optionally, PLAQUENIL™) alone or with (or formulated with) or in combination with any of (a) to (bb), or chloroquine, chloroquine phosphate, chloroquine diphosphate and/or hydroxychloroquine (optionally, PLAQUENIL™) and oseltamivir (or TAMIFLU™);

(ff) chloroquine (optionally, ARALEN™), chloroquine phosphate, alone or with:
  (i) an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, optionally at a dosage of between about 3 to 340 mg per day, or about 6 mg to 60 mg, or about 10 mg to 80 mg dosages, or about 12 to 50 mg dosages;
  (ii) vitamin D, vitamin D2 (or ergocalciferol), vitamin D3 (or cholecalciferol) optionally at a dosage of between about 3,000 to 100,000 units per day, or between about 10,000 to 50,000 units a day, and/or
  (iii) with (i) and (ii) and zinc (optionally a zinc sulphate, acetate, gluconate or picolinate or any zinc salt) optionally at a dosage of between about 1 mg to 250 mg, or (iv) the combination of (iii) also with a tetracycline class drug, wherein optionally the tetracycline class drug comprises doxycycline, or DORYX™, DOXYHEXA™, DOXYLIN™, optionally dosages at between about 25 mg to 600 mg per day or per dose, optionally between about 100 mg to 500 mg, or a between about 200 mg to 400 mg per dose or per day;

(gg) colchicine, or COLCRYS™, MITIGARE™, optionally administered or dosaged at between about 0.5 mg to 20 mg, or about 1 mg to 15 mg, or about 3 mg to mg, or about 4 mg to 6 mg, per day for a period of between about 7 and 21 days, or about 14 days, and optionally also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily);

(hh) a corticosteroid or glucocorticoid class drug such as ciclesonide (or ALVESCO™, OMNARIS™, OMNIAIR™, ZETONNA™ or ALVESCO™) budesonide (optionally RHINOCORT™ or PULMICORT™), prednisolone (or ORAPRED™), methylprednisolone, prednisone (or DELTASONE™ or ORASONE™) or hydrocortisone (or CORTEF™), wherein optionally the corticosteroid or glucocorticoid class drug (optionally ciclesonide) is inhaled, or a selective estrogen receptor modulator (SERM), or toremifene (or FARESTON™), or clomifene or clomiphene (or CLOMID™, SEROPHENE™) wherein optionally the SERM is inhaled;

and optionally the corticosteroid class drug (for example budesonide) is administered by inhalation, for example, in a nebulized form, for example, between about 1 mg to 12 mg per day of budesonide is administered by inhalation, or between about 6 to 80 mg per day of prednisolone is administered orally, or between about 6 to 100 mg per day of prednisone is administered orally, or between about 30 to 400 mg per day of hydrocortisone is administered orally, and optionally the corticosteroid class drug is formulated as a powder or for administration in an inhaler or by nasal spray, or for rectal administration, and optionally the corticosteroid class drug (for example, budesonide) is administered together with or in combination with 10 mg to 80 mg, an antibiotic (optionally azithromycin or a tetracycline class drug, wherein optionally the tetracycline class drug comprises doxycycline, or DORYX™, DOXYHEXA™, DOXYLIN™), zinc or any zinc salt and/or a vitamin (optionally vitamin D or calcifediol, D2 (or ergocalciferol), D3 (or cholecalciferol), C, E, B12, B6);

(ii) an anti-androgen drug, and optionally the anti-androgen drug is bicalutamide, optionally CASODEX™, or dutasteride (or AVODART™), and optionally the anti-androgen drug is a nonsteroidal anti-androgen (NSAA) or an androgen receptor (AR) antagonist, and optionally the NSAA or AR antagonist comprises proxalutamide (or its developmental name GT-0918) (Suzhou Kintor Pharmaceuticals, Inc., a subsidiary of Kintor Pharmaceutical Limited), or flutamide (or niftolide, or EULEXIN™), or bicalutamide (or CASODEX™) or enzalutamide (or XTANDI™), and optionally the anti-androgen drug comprises a 5α-reductase inhibitor, and optionally the 5α-reductase inhibitor comprises finasteride (or PROSCAR™, PROPECIA™, or FINIDE™)

and optionally the anti-androgen drug, or NSAA, or proxalutamide or bicalutamide, is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, epinomectin or abamectin;

and optionally the anti-androgen drug, or NSAA, or bicalutamide, proxalutamide, flutamide or niftolide, bicalutamide, enzalutamide or dutasteride, is administered at dosages of about 50 to 100 mg optionally administered once, twice (BID), three times (TID) or four times a day, or is administered at dosages of about 50 to 100 mg per day, and optionally the anti-androgen drug, or NSAA, or bicalutamide, proxalutamide, flutamide or niftolide, bicalutamide, enzalutamide or dutasteride, is administered with an avermectin class drug, or ivermectin, optionally also administered with hydroxychloroquine, zinc and/or a vitamin (optionally vitamin D (optionally vitamin D2, or ergocalciferol, or Vitamin D3 or cholecalciferol, optionally administered at about 1000 to 4000 ugm/day) or vitamin C, B or A;

and optionally bicalutamide is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and optionally bicalutamide is administered together with or in combination with an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin;

(jj) a hydrocortisone or cortisol (optionally CORTEF™, SOLUCORTEF™), optionally hydrocortisone sodium succinate or hydrocortisone acetate or dexamethasome (optionally DEXTENZA™, OZURDEX™, NEOFORDEX™);

(kk) an alpha-ketoamide (α-ketoamide), wherein optionally the alpha-ketoamide is a structure as described by Zhang et al, J. Med. Chem. 2020, 63, 9, 4562-4578, or Meng et al Chem. Sci. (2019) vol. 10, pg 5156 (optionally the structure KAM-2), and optionally the alpha-ketoamide is formulated or administered as an inhalant or a powder or mist, and optionally formulated or administered with (optionally as an inhalant): an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin; an antibiotic (optionally azithromycin or a tetracycline class drug, wherein optionally the tetracycline class drug comprises doxycycline, or DORYX™, DOXYHEXA™, DOXYLIN™); chloroquine (or ARALEN™), chloroquine phosphate, chloroquine diphosphate and/or hydroxychloroquine (optionally, PLAQUENIL™); zinc or any zinc salt; remdesivir (optionally, GS-5734™, Gilead Sciences); oseltamivir (or TAMIFLU™); and/or, hydrocortisone; or, any combination thereof;

(ll) a compound, drug or formulation that decreases stomach acid production or decreases stomach pH, wherein optionally the compound, drug or formulation comprises famotidine, or PEPCID™, and optionally the famotidine is administered at a dosage of between about 10 to 60 mg per day, or between about 20 to 40 mg per day, and optionally the famotidine is administered is administered with: an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and/or a tetracycline tetracycline class drug, and optionally the tetracycline class drug comprises doxycycline, or DORYX™, DOXYHEXA™, DOXYLIN™;

(mm) a dendrimer, optionally astodrimer sodium (Starpharma, Melbourne, Australia);

(nn) an antihistamine class drug such as azelastine, or ASTELIN™, OPTIVAR™, ALLERGODIL™, brompheniramine, fexofenadine or ALLEGRA™ pheniramine or AVIL™, or chlorpheniramine;

(oo) a selective serotonin reuptake inhibitor (SSRI) class drug, optionally fluvoxamine, or LUVOX™, FAVERIN™, FLUVOXIN™;

(pp) a nicotinic antagonist, a dopamine agonist or a noncompetitive N-Methyl-d-aspartic acid or N-Methyl-d-aspartate (NMDA) antagonist, wherein optionally the nicotinic antagonist, dopamine agonist or noncompetitive NMDA antagonist is 1-adamantylamine or amantadine, or GOCOVRI™, SYMADINE™, SYMMETREL™, optionally administered or dosaged at between about 50 mg to 150 mg, or about 100 mg, per day for a period of between about 7 and 21 days, or about 14 days, and optionally the nicotinic antagonist, dopamine agonist or noncompetitive NMDA antagonist is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally the amantadine is formulated or administered at 100 mg per day for the first two days of treatment, which optionally can then be elevated to 100 mg twice daily, optionally for the next 10 days;

(qq) an immunosuppressive drug, wherein optionally the immunosuppressive drug comprises tocilizumab or atlizumab, or ACTEMRA™, or ROACTEMRA™, or a calcineurin inhibitor (CNI), wherein the CNI comprises ciclosporin (or cyclosporine or cyclosporin), or NEORAL™, or SANDIMMUNE™, or tacrolimus, or PROTOPIC™, or PROGRAF™, and optionally the immunosuppressive drug is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally the calcineurin inhibitor (CNI), wherein the CNI comprises ciclosporin (or cyclosporine or cyclosporin) is formulated combination of CNI (optionally cyclosporine) at a dose of 3 mg/kg (180 mg daily) together with 12 mg ivermectin once, and optionally also plus zinc 50 mg base and doxycycline 100 mg bid, optionally all for 10 days;

(rr) a protein kinase inhibitor, wherein optionally the protein kinase inhibitor is a p38 mitogen-activated protein kinase inhibitor, or ralimetinib, and optionally the protein kinase inhibitor is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily);

(ss) an anti-inflammatory therapy or at least one anti-inflammatory therapy drug, wherein optionally the anti-inflammatory therapy or drug comprises: a sphingosine kinase-2 (SK2) selective inhibitor (optionally, opaganib (optionally, YELIVA™), sirolimus, a JAK1/2/TYK2 inhibitor (optionally ruxolitinib), an anti-CD47 mAb (optionally meplazumab), a cyclooxygenase (COX) (optionally, COX2) inhibitor, a glucocorticoid (optionally a synthetic glucocorticoid, hydrocortisone, dexamethasone (or DEXTENZA™, OZURDEX™, or NEOFORDEX™) or cortisol, or CORTEF™), plitidepsin or dehydrodidemnin B, or APLIDIN™, or a nonsteroidal anti-inflammatory drug (NSAID), wherein optionally the NSAID comprises indomethacin (or indomethacin) or INDOCID™ or INDOCIN™, or naproxen, or NAPROSYN™ or ALEVE™, or a cyclooxygenase inhibitor, or a COX-1 or an COX-2 inhibitor, or aspirin, or ibuprofen or ADVIL™, MOTRIN™ or NUROFEN™, or celecoxib or CELEBREX™, or parecoxib or DYNASTAT™, or etoricoxib or ARCOXIA™, and optionally the anti-inflammatory therapy or anti-inflammatory therapy drug is also administered or formulated with an antibiotic (optionally azithromycin or doxycycline), ivermectin, hydroxychloroquine (optionally, PLAQUENIL™) and/or zinc or any zinc salt (optionally zinc sulfate, optionally at (50 mg daily), and optionally opaganib, or YELIVA™, or opaganib, or YELIVA™ administered or formulated together with an oral and/or inhaled or aerosol chloroquine (or ARALEN™), chloroquine phosphate, chloroquine diphosphate and/or hydroxychloroquine (optionally, PLAQUENIL™), and optionally the opaganib or YELIVA™ is formulated or administered at a dosage of QD (once a day), bid (twice a day) or tid (three times a day) at a dosage of between about 100 to 600 mg per day or per dosage, or at about 100, 200, 300, 400, 500 or 600 mg per day or per dosage, and optionally the opaganib, or YELIVA™ is also administered or formulated with an antibiotic (optionally azithromycin or doxycycline), ivermectin (optionally at 12 mg ivermectin, optionally administered on days 1, 3, 6 and 8), hydroxychloroquine (optionally, PLAQUENIL™) and/or zinc or any zinc salt (optionally zinc sulfate, optionally at (50 mg daily);

(tt) a calcium channel blocker, or verapamil (or ISOPTIN™, CALAN™), or a voltage gated potassium (KCNH2) channel or a voltage gated calcium channel (CACNA2D2) blocker, or amiodarone (or CORDARONE™, NEXTERONE™);

(uu) suramin, or ANTRYPOL™, BAYER 305™, or GERMANIN™

(vv) a peroxisome proliferator-activated receptor (PPAR) agonist, wherein optionally the PPAR agonist comprises fenofibrate, or TRICOR™, FENOBRAT™, FENOGLIDE™, or LIPOFEN™, or a combination of fenofibrate and simvastatin, or CHOLIB™, optionally the PPAR agonist comprises a combination of fenofibrate and pravastatin, or PRAVAFENIX™, or the PPAR agonist comprises bezafibrate, or BEZALIP™, or combination of bezafibrate and chenodeoxycholic acid, or HEPACONDA™, or aluminium clofibrate, or alfibrate, or ciprofibrate, or clinofibrate or LIPOCLIN™, or clofibrate or ATROMID-S™, or clofibride, or gemfibrozil or LOPID™, or ronifibrate, or simfibrate or CHOLESOLVIN™, or any combination thereof, (ww) a synthetic nucleoside analog or derivative, or N4-hydroxycytidine, or a prodrug of N4-hydroxycytidine, optionally molnuvpiravir (Merck), or favipiravir (also known as T-705 or AVIGAN™, or favilavir, Toyama Chemical, Fujifilm, Japan, or FABIFLU™, Glenmark Pharmaceuticals), wherein the synthetic nucleoside analog or derivative, or N4-hydroxycytidine, or the prodrug of N4-hydroxycytidine, optionally molnuvpiravir or favipiravir, is given as between about 10 mg to 3 gm per dose, or between about 10 mg to 3 gm per day, or can be dosed either as a single dose or given one, two, three or four times a day, or is administered at 200 to 800 mg twice daily, or 200, 400, 600 or 800 mg twice daily, or at 200 to 800 mg three times a day, or at 200, 400, 600 or 800 mg three times a day, or is administered at 200 to 800 mg three times a day for between about 2 to 15 days, or for about 2, 3, 4, 5, 6, 7, 8, 9, 10, 11 or 12 days, and optionally when combined with other drugs a lower dosage is used, optionally administered at 100 or 200 mg three times a day for between about 5 to 15 days, or for about 7, 8, 9, 10, 11 or 12 days, and optionally the synthetic nucleoside analog or derivative, or N4-hydroxycytidine, or the prodrug of N4-hydroxycytidine, optionally molnuvpiravir or favipiravir, is administered with an avermectin class drug (optionally ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin), and optionally the synthetic nucleoside analog or derivative, or N4-hydroxycytidine, or the prodrug of N4-hydroxycytidine, optionally molnuvpiravir or favipiravir, is administered with an avermectin class drug (optionally ivermectin) with an antibiotic, and optionally the antibiotic comprises azithromycin, minocycline, amoxicillin, niclosamide, nitazoxanide, hydroxychloroquine or doxycycline), and optionally the synthetic nucleoside analog or derivative, avermectin class drug, and antibiotic are administered together or as separate formulations, and optionally are administered every one, two, three, four or five weeks for between about one month and one year or more;

and optionally molnuvpiravir, ivermectin and hydroxychloroquine are administered together or as separate formulations, and optionally are administered every one, two, three, four or five weeks for between about one month and one year or more;

and optionally the synthetic nucleoside analog or derivative (optionally N4-hydroxycytidine, or the prodrug of N4-hydroxycytidine, optionally molnuvpiravir or favipiravir), and antibiotic (optionally doxycycline or hydroxychloroquine) is administered with zinc (optionally a zinc sulphate, acetate, gluconate or picolinate, or zinc oxide nanoparticles, optionally at a dosage of between about 1 mg to 250 mg, or about 50 mg per day) and/or a vitamin, optionally vitamin C or D), and optionally the synthetic nucleoside analog or derivative, or N4-hydroxycytidine, or the prodrug of N4-hydroxycytidine, optionally molnuvpiravir or favipiravir, is administered with an antibiotic (optionally the antibiotic comprises azithromycin, minocycline, amoxicillin, niclosamide, nitazoxanide, hydroxychloroquine or doxycycline), optionally also administered with zinc (optionally a zinc sulphate, acetate, gluconate or picolinate, or zinc oxide nanoparticles, optionally at a dosage of between about 1 mg to 250 mg, or about 50 mg per day) and/or a vitamin, optionally vitamin C or D, and optionally the anti-androgen drug, or NSAA, or bicalutamide, proxalutamide, flutamide or niftolide, bicalutamide, enzalutamide or dutasteride, is administered with colchicine (or COLCRYS™, MITIGARE™), and optionally also zinc and/or a vitamin (optionally vitamin D (optionally vitamin D2, or ergocalciferol, or Vitamin D3 or cholecalciferol, optionally administered at about 1000 to 4000 ugm/day), or vitamin C, B or A), and optionally the anti-androgen drug, or NSAA, or bicalutamide, proxalutamide, flutamide or niftolide, bicalutamide, enzalutamide or dutasteride, is administered with an antibiotic (optionally azithromycin or doxycycline), and optionally also zinc and/or a vitamin (optionally vitamin D (optionally vitamin D2, or ergocalciferol, or Vitamin D3 or cholecalciferol, optionally administered at about 1000 to 4000 ugm/day), or vitamin C, B or A), and optionally also with hydroxychloroquine;

(xx) an anti-malarial drug, wherein optionally the anti-malarial drug comprises mefloquine (or LARIAM™, MEPHAQUIN™, or MEFLIAM™)

(yy) an antisera or an antibody or antibody or vaccine therapy for treating, preventing or ameliorating a microbial or a viral infection (optionally a coronavirus infection, optionally a COVID-19 infection) or a microbial infection (optionally a protozoan, helminthiasis, insect and/or parasitic infection), and optionally the antibody comprises a monoclonal antibody, and optionally the monoclonal antibody comprises sotrovimab (GlaxoSmithKline and Vir Biotechnology), or casirivimab, imdevimab or casirivimab and imdevimab (REGEN-COV™) (Regeneron), or bamlanivimab oretesevimab or bamlanivimab and etesevimab (Junshi Biosciences), or tocilizumab or ACTEMRA™ or ROACTEMRA™ (Hoffmann-La Roche), and optionally the vaccine comprises tozinamera or COMIRNATY™ (Pfizer), or elasomeran or SPIKEVAX™ (Moderna), or SPUTNIK V™ or Gam-COVID-Vac (Gamaleya Research Institute), or AZD1222 or COVISHIELD™ or VAXZEVRIA™ (Oxford-AstraZeneca), and optionally the antibody or antibody therapy comprises or is contained in a convalescent sera or plasma, and/or (zz) any combination of (a) to (yy), and optionally any of these combinations is administered very 2, 3, 4, 5, 6, 7, 8, 9 or 10 or more days for between about 1 month and one year or more, and optionally any one or several or all of (a) to (zz) with an (or formulated with or formulated as an) inhaled or aerosol formulation such as a powder, spray or a mist or aerosol, and/or formulated with or formulated as an oral, intramuscular (IM) or intravenous (IV) formulation, wherein optionally both the inhaled (or aerosol) and the oral, IV and/or IM formulations are administered simultaneously or sequentially, and optionally the inhaled or aerosol formulation comprises chloroquine (or ARALEN™), chloroquine phosphate, chloroquine diphosphate and/or hydroxychloroquine (optionally, PLAQUENIL™) and/or oral chloroquine (or ARALEN™), chloroquine phosphate, chloroquine diphosphate and/or hydroxychloroquine (optionally, PLAQUENIL™) administered simultaneously or overlapping, and optionally the inhaled or aerosol formulation comprises an avermectin class drug such as ivermectin (optionally STROMECTOL™), moxidectin (optionally CYDECTIN™, EQUEST™, QUEST™), selamectin (optionally STRONGHOLD™), a milbemycin (optionally milbemectin, milbemycin oxime, moxidectin or nemadectin), doramectin (optionally DECTOMAX™), eprinomectin or abamectin, and optionally any one or several or all of (a) to (zz), or any therapeutic combination of drugs or a drug, or a pharmaceutical dosage form as provided herein, are administered orally, intramuscularly, subcutaneously, topically, by use of an enema, intravaginally, or intravenously, or administration is by subcutaneous administration, sublingual administration, inhalation or by aerosol (optionally by inhalation of a liquid, an aerosol, a spray, a mist or a powder), by absorbable patch, by use of an implant, or by use of an enema or a suppository.

In alternative embodiments, the anti-viral drug or medication, or anti-microbial drug, is or comprises: molnupiravir, efavirenz (optionally, SUSTIVA™), tenofovir, emtricitabine and tenofovir, nevirapine (or the combination efavirenz with emtricitabine and tenofovir, or ATRIPLA™), amprenavir (optionally, AGENERASE™), nelfinavir (optionally, VIRACEPT™) and/or remdesivir (optionally, GS-5734™, Gilead Sciences), a viral RNA-dependent RNA polymerase inhibitor, optionally galidesivir, a nucleoside analog reverse-transcriptase inhibitor (NRTI) (optionally abacavir, or ZIAGEN™)

and optionally the anti-viral drug or medication is or comprises an anti-retroviral drug or drug combination, and optionally the anti-retroviral drug or drug combination comprises: darunavir and cobicistat (optionally, REZOLSTA™ or PREZCOBIX™); atazanavir and cobicistat (or EVOTAZ™); abacavir, lamivudine and dolutegravir (TRIUMEQ™); tenofovir (or disoproxil or emtricitabine) and elvitegravir and cobicistat (optionally, STRIBILD™); tenofovir (or disoproxil or emtricitabine) and elvitegravir and cobicistat (COMPLERA™ or EVIPLERA™); molnupiravir, efavirenz (optionally, SUSTIVA™), emtricitabine and tenofovir (ATRIPLA); lamivudine, nevirapine and stavudine (optionally, TRIOMUNE™); atazanavir and cobicistat (optionally, EVOTAZ™); lamivudine and raltegravir (optionally, DUTREBIS™); lamivudine and dolutegravir (or DOVATO™); doravirine, lamivudine and tenofovir (optionally, DELSTRIGO™); or lamivudine, zidovudine and nevirapine (optionally, CUOVIR-N™);

and optionally the additional anti-viral drug or medication, or anti-microbial drug, is formulated with the chloroquine (optionally, ARALEN™), chloroquine phosphate, chloroquine diphosphate, hydroxychloroquine (optionally, PLAQUENIL™), lopinavir, ritonavir (or NORVIR™) and/or oseltamivir or is formulated separately from the chloroquine (optionally, ARALEN™), chloroquine phosphate, chloroquine diphosphate, hydroxychloroquine (optionally, PLAQUENIL™), lopinavir, ritonavir (or NORVIR™) and/or oseltamivir, and optionally the anti-viral drug or medication, or anti-microbial drug, or palliative agent comprises or further comprises: magnesium (Mg, optionally administer intravenously (IV) to maintain a blood concentration of between about 2.0 and 2.4 mmol/l); zinc or any zinc salt (optionally a zinc sulphate, acetate, gluconate or picolinate, optionally administered at about 75 to 100 mg/day or at a dosage of between about 1 mg to 250 mg); at least one vitamin, wherein optionally the at least one vitamin comprises vitamin K, vitamin D or calcifediol (optionally D2 (or ergocalciferol) or Vitamin D3 or cholecalciferol), optionally administered at about 1000 to 4000 ugm/day), vitamin B6 (or pyridoxine), vitamin B12, vitamin E, and/or vitamin C (optionally administered at 500 mg bid); a flavonoid, plant flavonol or quercetin optionally administered at between about 250 to 500 mg bid; atorvastatin, or LIPITOR™, SORTIS™ (optionally administered at between about 40 mg/day to 80 mg/day); or, melatonin, or CIRCADIN™, SLENYTO™ (optionally between about 6 to 12 mg a day, optionally, at night), any of which are optionally given enterally or parenterally.

Anti-Clotting or Blood Thinning Agents

In alternative embodiments for practicing methods as provided herein, to address the possibility of blood clotting, whether the blood clotting is caused by the infectious agent, the administered inactivated or attenuated causative agent of the infection, or the live, viable or infectious causative agent of the infection, and/or the vaccine or for any another reason, an anti-clotting or anti-coagulant or blood thinning drug or agent is also administered, for example, before and/or at the commencement of the vaccination, and optionally is continued for between about 1 to 2 or 1 to 6 weeks after the vaccination, or for the duration of the anti-microbial drug treatment though administration of a second or booster vaccination, and/or for between about 1 to 2 weeks after administration of the second or booster vaccination.

In alternative embodiments, the anti-clotting agent or anti-coagulant or blood thinning drug or agent comprises aspirin, for example between about 100 mg to 500 mg aspirin administered (for example, in the morning, or AM, or MANE) for 2, 3, 4, 5, 6, 7, 8, 9, 10, 11, 12, 13 or 14 or more days commencing on the day of the vaccination or commencing one or two days before the vaccination day.

In alternative embodiments, antiplatelet drugs that can be used include clopidogrel (PLAVIX™), prasugrel (EFFIENT™) and ticagrelor (BRILINTA™).

In alternative embodiments, the anti-clotting or anti-coagulant agent or blood thinning drug or agent comprises: heparin; warfarin (or COUMADIN™); a coumarin; phenprocoumon (or MARCUMAR™); rivaroxaban (XARELTO™); dabigatran (PRADAXA™); apixaban (ELIQUIS™); edoxaban (LIXIANA™) and/or betrixaban (BEVYXXA™)

Vaccines

In alternative embodiments, provided are methods for treating, ameliorating, decreasing the chances of having any adverse effects from, decreasing the severity of adverse effects from, or preventing an infection by administration of an antibiotic and/or an anti-viral drugs and a vaccine directed to a causative agent of the infection, and/or an inactivated or attenuated causative agent of the infection, or a live, viable or infectious causative agent of the infection.

In alternative embodiments, vaccines used to practice methods as provided herein are directed to an exterior-expressed protein of a pathogen, for example, where the pathogen is a bacteria or a virus, for example, the exterior-expressed protein comprises a spike protein of a virus, for example, a spike protein of a coronavirus, for example, a Covid-19 spike protein.

In alternative embodiments, vaccines used to practice methods as provided herein are formulated and administered using any formulations, protocols or techniques known in the art, for example, pharmaceutical formulations or vaccines as provided herein can be administered as peptides, or can be administered in the form of nucleic acids that encode the immunogenic peptides or proteins. In alternative embodiments, vaccines used to practice methods as provided herein comprise orally and intra-nasally administered vaccines.

In alternative embodiments, vaccines used to practice methods as provided herein comprise administration of inactivated pathogen, for example, an inactivated virus (optionally an inactivated whole or entire pathogen (or virus) or substantially a whole or entire pathogen (or virus), for example, an inactivated coronavirus, for example, and inactivated COVID-19 virus, for example, as manufactured by Valneva, France), Sinopharm, or Bharat Biotech. In alternative embodiments, the pathogen (or virus) is inactivated using a chemical, for example, a beta-propiolactone (BPL) or equivalent, or any means used to inactivate a viruses for a vaccine. This type of inactivation can preserve the structure of the pathogen (for example, viral) proteins, as they would occur in nature. This means the immune system will be presented with something similar to what occurs naturally and mount a strong immune response. In alternative embodiments, after being inactivated, the vaccine (or, the inactivated pathogen, or virus) is highly purified. In alternative embodiments, an adjuvant (or any immune stimulant) is added or co-administered to induce a boosted or strong immune response.

In alternative embodiments, vaccines used to practice methods as provided herein are DNA vaccine or RNA vaccines. For example, in alternative embodiments the immunogen-encoding nucleic acid can be a DNA encoding one or more immunogenic peptides or proteins, and the DNA can be carried in an expression vehicle such as a viral vector, for example an adenovirus vector such as an Ad5 or adeno-associated vector (AAV). In alternative embodiments, recombinant adenoviruses as used in vaccines as provided herein can be as described in U.S. patent application no. US 20200399323 A1, which describes for example recombinant adenoviruses including a deletion in or of the E1 region or any deletion that renders the virus replication-defective, for example, the replication-defective virus can include a deletion in one or more of the E1, E3, and/or E4 regions; or, can be as described in U.S. patent application no. US 20190382793 A1, which described how to make recombinant adenoviruses for gene therapy.

In alternative embodiments, the immunogen-encoding nucleic acid can be an RNA, for example, mRNA, which can be formulated in a lipid formulation or a liposome and injected for example intramuscularly (IM), for example using formulations and methods as described in U.S. patent application no. US 20210046173 A1, which describes delivering to a subject (for example, via intramuscular administration) an immunogenic composition that comprises a RNA (for example, mRNA) that comprises an open reading frame (ORF) that comprises (or consists of, or consists essentially of) an immunogenic or antigenic sequence as provided herein; wherein optionally the RNA (or the DNA-carrying expression vehicle) is formulated in a liposome, or a lipid nanoparticle (LNP), or nanoliposome, that comprises: non-cationic lipids comprise a mixture of cholesterol and DSPC, or a PEG-lipid, or PEG-modified lipid, or LNP, or an ionizable cationic lipid; or a mixture of (13Z,16Z)-N,N-dimethyl-2-nonylhenicosa-12,15-dien-1-amine, cholesterol, DSPC, and PEG-2000 DMG. In alternative embodiments, the PEG-lipid is 1,2-Dimyristoyl-sn-glycerol methoxypolyethylene glycol (PEG-DMG), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA), or, the PEG-lipid is PEG coupled to dimyristoylglycerol (PEG-DMG). In alternative embodiments, the LNP comprises 20-99.8 mole % ionizable cationic lipids, 0.1-65 mole % non-cationic lipids, and 0.1-20 mole % PEG-lipid. In alternative embodiments, the LNP comprises an ionizable cationic lipid selected from the group consisting of (2S)-1-({6-[(3))-cholest-5-en-3-yloxy]hexyl}oxy)-N,N-dimethyl-3-[(9 Z)-octadec-9-en-1-yloxy]propan-2-amine; (13Z,16Z)-N,N-dimethyl-3-nonyldocosa-13,16-dien-1-amine; and N,N-dimethyl-1-[(1S,2R)-2-octylcyclopropyl]heptadecan-8-amine; or a pharmaceutically acceptable salt thereof, or a stereoisomer of any of the foregoing. In alternative embodiments, the PEG modified lipid comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In alternative embodiments, the ionizable cationic lipid comprises: 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy) heptadecanedioate (L319), (13Z,16Z)-N,N-dimethyl-3-nonyldocosa-13,16-dien-1-amine, (12Z,15Z)-N,N-dimethyl-2-nonylhenicosa-12,15-dien-1-amine, and N,N-dimethyl-1-[(1S,2R)-2-octylcyclopropyl]heptadecan-8-amine. In one embodiment, the lipid is (13Z,16Z)-N,N-dimethyl-3-nonyldocosa-13,16-dien-1-amine or N,N-dimethyl-1-[(1S,2R)-2-octylcyclopropyl]heptadecan-8-amine, each of which are described in PCT/US2011/052328, the entire contents of which are hereby incorporated by reference. In some embodiments, a non-cationic lipid of the disclosure comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, or mixtures thereof.

Attenuated, or Live, Viable or Infectious Causative Agent of the Infection

In alternative embodiments, provided are methods for treating, ameliorating, decreasing the chances of having any adverse effects from, decreasing the severity of adverse effects from, or preventing an infection, comprising administering to a subject or an individual in need thereof:

(a) at least one antibiotic and/or anti-viral drug capable of killing a causative agent of the infection, or completely or partially inhibiting the ability of the causative agent of the infection to replicate or become infectious or cause pathology in the subject or the individual in need thereof; and, (b) (i) at least one dose of a vaccine directed to the causative agent of the infection upon entry into the vaccinated subject or individual in need thereof,
wherein the vaccine is capable of initiating an immune response in the individual that can substantially or partially kill or neutralize a causative agent of the infection, or the vaccine can completely, substantially or partially inhibit the ability of the causative agent of the infection to replicate, or be infectious, or cause pathology, in the subject or the individual in need thereof, and/or (ii) an inactivated or attenuated causative agent of the infection, or a live, viable or infectious causative agent of the infection, wherein optionally the live causative agent of the infection is a completely or partially attenuated version of the causative agent, wherein at least one dosage of the at least one antibiotic and/or anti-viral drug is administered 1, 2, 3, 4, 5, 6, 7, 8, 9, 10, 11, 12, 13 or 14 or more days before, or on the day of, a first dose of the at least one of a plurality of dosages of the vaccine is administered, or a dose of the inactivated, attenuated causative agent of the infection, or the live, viable or infectious causative agent of the infection.

In alternative embodiments, the causative agent of the infection is or comprises a bacteria, protozoan or a virus, or the causative agent of the infection is or comprises the causative agent of:

a viral infection, optionally a coronavirus, a virus that causes a common cold, an influenza virus (optionally an influenza A, B or C), a hepatitis virus, a rous sarcoma virus (RSV), a Paramyxoviridae or measles virus, a Paramyxovirus or mumps virus, a Herpes simplex virus (HSV), a Cytomegalovirus (CMV), a Rubivirus or rubella virus, an Enterovirus, a viral meningitis, a rhinovirus, a human immunodeficiency virus (HIV), a varicella-zoster or chickenpox virus, an Orthopoxvirus or variola or smallpox virus, an Epstein-Barr virus (EBV), an Adenovirus, a Hantavirus, a Flaviviridae or Dengue virus, a Zika virus, or a chikungunya virus infection, a coronavirus infection, optionally a COVID-19 or a COVID-19 variant infection, or a Middle East respiratory syndrome virus (MERS-CoV) infection;

malaria caused by a parasite of the genus *Plasmodium* (optionally *P. vivax, P. falciparum, P. malariae, P. ovale*, or *P. knowlesi*);

dengue fever or dengue shock syndrome caused by a virus of the Flaviviridae family or a dengue virus;

a Flaviviridae family virus infection or a hepatitis or a hepatocellular carcinoma associated with viral hepatitis caused by a virus of the Flaviviridae family or a virus of the genus Hepacivirus or Hepacivirus C virus or hepatitis C;

filariasis, leprosy or streptocerciasis or an infection caused by a parasite of the superfamily Filarioidea (optionally *Brugia malayi, Brugia timori, Wuchereria bancrofti, Loa loa, Mansonella streptocerca, Mansonella ozzardi*, or *Mansonella* perstans);

leprosy or an infection caused by a parasite of the genus *Mycobacterium* (optionally *M. leprae* or M. lepromatosis);

river blindness or onchocerciasis caused by a parasitic worm or a parasite of the genus *Onchocerca* (optionally *O. volvulus*);

a hookworm or a roundworm infection caused by a parasite of the genus *Ancylostoma* (optionally *A. duodenale* or *A. ceylanicum*) or Necator (optionally *N. americanus*);

trichuriasis or a whipworm infection caused by a parasite of the genus *Trichuris* (optionally *T. trichiura*); roundworm or an *Ascaris* infection that is caused by *Ascaris lumbricoides;* scabies or a mite-carried infection caused by the parasite of the genus *Sarcoptes* (optionally *S. scabiei*);

typhus or an infection caused by a lice or a parasite of the order Phthiraptera (optionally *Pediculus humanus* capitis);

enterobiasis or an infection caused by a pinworm or a parasite of the genus *Enterobius* (optionally *E. vermicularis*); and/or pulicosis or an infection caused by a flea or an insect of the order Siphonaptera or of the genus *Pulex* (optionally *P. irritans*).

In alternative embodiments, the inactivated or attenuated causative agent of the infection, or the live, viable or infectious causative agent of the infection is administered orally or by inhalation. Alternatively, the inactivated or attenuated causative agent of the infection, or the live, viable or infectious causative agent of the infection can be administered by inclusion of the live, viable or infectious causative agent of the infection in a liquid (optionally to be administered as a drink or in drops such as nasal drops), a tablet, a lozenge, an aerosol, spray, or mist formulation that is inhaled or administered nasally or orally (optionally, by a puffer of a nebulizer), or the inactivated or attenuated causative agent of the infection, or the live, viable or infectious causative agent of the infection is formulated in a liquid (optionally the liquid is a sterile saline) solution which is ingested or gargled by the individual in need thereof.

In alternative embodiments, the source of the inactivated or attenuated causative agent of the infection, or the administered live, viable or infectious causative agent of the infection can be from an infected individual, such as a human patient, a domesticated, wild or lab animal, or from a lab-grown culture. In alternative embodiments, the source of the administered inactivated or attenuated causative agent of the infection, or the live, viable or infectious causative agent of the infection is from swab or sputum or other biological samples from an infected individual or patient. In alternative embodiments, the sputum or other biological sample from an infected individual or patient is diluted in a water or a saline prior to administrations.

In alternative embodiments, the administered inactivated or attenuated causative agent of the infection, or the live, viable or infectious causative agent of the infection is attenuated (in other words, its ability to cause pathogenesis is completely, substantially or partially abrogated or diminished, for example is genetically deleted or diminished by genomic engineering).

In alternative embodiments, to generate an attenuated (e.g., completed inactivated) version of a causative agent of the infection to be administered, the causative agent of the infection is passaged multiple times in culture (or in vitro) or in an animal (or in vivo), where variants from each passage are selected for a phenotype and/or genotype that has diminished ability to cause pathogenesis.

In alternative embodiments, to generate an attenuated (e.g., completed inactivated, completely non-infectious) version of a causative agent of the infection to be administered, the causative agent of the infection is treated with radiation and/or a chemical. For example, the chemical can be iodine (for example, povidone-iodine or PVP-1, also known as iodopovidone, or BETADINE™, WOKADINE™, PYODINE™), or any complex of polyvinylpyrrolidone and iodine, alcohol and/or formalin.

In alternative embodiments, the causative agent of the infection is rendered inactive, or non-infectious, by exposing the causative agent of the infection to iodine or povidone-iodine or PVP-1 (povidone is also known as polyvinylpyrrolidone (PVP), or 1-vinyl-2-pyrrolidinon-polymere), also known as iodopovidone, or BETADINE™, WOKADINE™, PYODINE™, as in the production of nasodine (Firebrick Pharma Pty Ltd, Australia). Povidone-iodine is a chemical complex of povidone, hydrogen iodide, and elemental iodine or triiodide ($I^{3-}$); and it contains 10% povidone, with total iodine species equaling 10,000 ppm or 1% total titratable iodine, and it works by releasing iodine which results in the death of a range of microorganisms. In alternative embodiment, the causative agent of infection is mixed with PVP-I and water, ethyl alcohol, isopropyl alcohol, polyethylene glycol or glycerol.

In alternative embodiments, the attenuated, or inactivated, causative agent, or live causative agent, is administered with an adjuvant, where the adjuvant can comprise: an inorganic compound such as alum (e.g., potassium alum), an aluminium salt or aluminium hydroxide, aluminium phosphate, or calcium phosphate; an oil such as paraffin oil, propolis or Adjuvant 65; a bacterial product such as killed bacteria of the genus *Bordetella* or *Mycobacterium* or of the species *Bordetella pertussis* or *Mycobacterium bovis*; a plant saponin or soybean extract; a cytokine such as interleukin-1 (IL-1), IL-2 or IL-12; Freund's complete adjuvant or Freund's incomplete adjuvant; and/or, an organic compound such as squalene.

In alternative embodiments, the attenuated, or inactivated, causative agent, or live causative agent, with or without an adjuvant, is administered by nasal spray or nebulizer, or orally for example by lozenge, tablet, capsule or geltab, or by subcutaneous injection, or intramuscularly (IM), or by suppository, or via an implant.

In alternative embodiments, attenuated viruses are made using a live attenuated codon-pair-deoptimized virus approach as described for example in Wang et al PNAS, Jul. 20, 2021, vol. 18 (29) e2102775118; or as described by Coleman et al. Science 320, 1784-1787 (2008), or Cheng et al J. Virol. 89, 3523-3533 (2015), or Gonçalves-Carneiro, mBio 12, e02238-20 (2021).

For example, methods as provided herein comprise administration of the Wang et al, COVI-VAC™ attenuated virus, which was developed by recoding a segment of the viral spike protein with synonymous suboptimal codon pairs (codon-pair deoptimization), thereby introducing 283 silent (point) mutations. As described by Wang et al, synthetic highly attenuated live vaccine is generated by recoding portions of the WT SARS-CoV-2 genome according to the SAVE algorithm of codon-pair bias deoptimization. In addition, the furin cleavage site within the spike protein was deleted from the viral genome for added safety of the vaccine strain. Except for the furin cleavage site deletion, the COVI-VAC and parental SARS-CoV-2 amino acid sequences are identical, ensuring that all viral proteins can engage with the host immune system of vaccine recipients. Attenuated viruses can be generated from viral genomes recover from WT SARS-CoV-2, strain USA-WA1/2020 (GenBank accession No. MN985325).

In alternative embodiments, the inactivated or attenuated causative agent of the infection, or the live, viable or infectious causative agent of the infection, is administered in unit dosages of between about 10 to 50, or 1 to 20, trillion infectious units (or particles, if attenuated), or between about one infectious unit to 10, 20 or 30 billion infection units (or particles, if attenuated).

Hand-Held or Portable Devices

In alternative embodiments, provided are portable, for example, hand-held (or worn around the neck), medical devices, for example, an inhaler, ionizer, asthma puffer or nebulizer, capable of administering an inhalation product comprising a composition or formulation as provided herein or as described herein, for example, an inactivated or attenuated agent of the infection, or a live, viable or infectious causative agent of the infection with or without a vaccine or with or without an adjuvant, or with or without an antimicrobial drug, for example, as described herein.

In alternative embodiments, a portable, for example, hand-held, medical device, for example, inhaler, asthma puffer or nebulizer, as provided herein can administer ionized air or air comprising generated electrons and/or negatively-charged oxygen ions and/or positively-charged ions.

In alternative embodiments, a portable or hand-held medical device as provided herein comprises a cassette, packette, interchangeable disk (for example, for holding a powder) or reservoir (optionally a refillable reservoir) in or on the product of manufacture, or a removable cassette or packette, interchangeable disk (for example, for holding a powder) that can be inserted into a slot or port on the product of manufacture, or a separate reservoir or container operatively linked or joined to the product of manufacture, that comprises a vaccine or or live or attenuated causative agent of invention or a formulation or a medication, for inhalation as provided herein for delivery to a user.

In alternative embodiments, provided is a modified hairdryer-type medical device capable of having an adjustable temperature, adjustable air intake; a provision (or receptacle) for insertion of a drug-containing cassette (optionally providing or delivering a combination of medications, or the live or attenuated causative agents and/or a vaccine as provided herein); and/or warm-to hot air availability (optionally with temperature control) to inhibit viral and bacterial growth.

In alternative embodiments, a medical device as provided herein for inhalation delivery of a live or attenuated causative agent of infection and/or a vaccine as provided herein drug or a medication or combinations thereof to a user is fabricated as a meter-dose inhaler (MDI) (either open or closed mouth MDI), which can comprise a pressurized canister of the drug or medication in a plastic case with a mouthpiece, and a holding chamber having a plastic tube with a mouthpiece, a valve to control mist delivery and a soft sealed end to hold the MDI; the holding chamber can assist delivery of the drug or medication to the nose and/or lungs, for example, as an AEROCHAMBER™ device.

In alternative embodiments, the inhaler or nebulizer is breath activated, for example, as an REDIHALER™ device.

In alternative embodiments, a medical device as provided herein for inhalation delivery of a live or attenuated causative agent of infection and/or a vaccine or a drug or a medication or combinations thereof to a user is fabricated a dry powder inhaler (such as a dry powder disk inhaler, for example, as a DISKUS™ device), optionally having a dose counter window so user can see how many doses are left), for example, where the powder is dose dispensed by (using) a disposable, refillable or replaceable cassette, packette or disk; and the dry powder dispensing can be breath activated, for example, as an AEROLIZER™, FLEXHALER™, PRESSAIR™, DISKUS™, HANDIHALER™, TWISTHALER™, ELLIPTA™, NEOHALER™, RESPICLICK™, ROTAHALER™ or TUBUHALER™ device.

In alternative embodiments, a medical device as provided herein for inhalation delivery of a live or attenuated causative agent of infection, or a vaccine or a drug or a medication or combinations thereof, to a user is fabricated a nebulizer or soft mist inhaler, which can comprise a nebulizer delivery system comprising a nebulizer (for example, a small plastic bowl with a screw-top lid) and a source for compressed air to generate a mist comprising the drug or medication, which also can be dose dispensed using a disposable, refillable or replaceable cassette, packette or disk.

In alternative embodiments, a medical device as provided herein for inhalation delivery of a live or attenuated causative agent of infection, or a vaccine or drug or a medication or combinations thereof to a user is fabricated a dry powder inhaler (such as a dry powder disk inhaler, for example, as a DISKUS™ device), optionally having a dose counter window so user can see how many doses are left), for example, where the powder is dose dispensed by (using) a disposable, refillable or replaceable cassette, packette or disk; and the dry powder dispensing can be breath activated, for example, as an AEROLIZER™, FLEXHALER™, PRESSAIR™, DISKUS™, HANDIHALER™, TWISTHALER™, ELLIPTA™, NEOHALER™, RESPICLICK™, ROTAHALER™ or TUBUHALER™ device.

Products of Manufacture and Kits

Provided are products of manufacture and kits for practicing methods as provided herein; and optionally, products of manufacture and kits can further comprise instructions for practicing methods as provided herein.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About (use of the term "about") can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 75%, 80%, 85%, 90%, 91%, 92%, 93%, 94%, 95%, 96%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention.

A number of embodiments of the invention have been described. Nevertheless, it can be understood that various modifications may be made without departing from the spirit and scope of the invention. Accordingly, other embodiments are within the scope of the following claims.

What is claimed is:

1. A method for treating, ameliorating, decreasing the chances of having any adverse effects from, decreasing the severity of adverse effects from a coronavirus infection, comprising administering to a subject or an individual in need thereof:

(a) an anti-viral drug combination capable of killing a causative agent of the infection, or inhibiting the ability of the causative agent of the infection to replicate or become infectious or cause pathology in the subject or the individual in need thereof wherein the anti-viral drug combination comprises:

(i) 1R,2S5S)-N-[(1S)-1-cyano-2-[(3S)-2-oxopyrrolidin-3-yl]ethyl]-3-[(2S)-3,3-dimethyl-2-(2,2,2-trifluoroacetamido)butanoyl]-6,6-dimethyl-3-azabicyclo[3.1.0]hexane-2-carboxamide, or a compound having the following structure and molecular weight:

PF-07321332

$C_{23}H_{32}F_3N_5O_4$

FW: 499.527

(ii) ritonavir, and (iii) a drug combination comprising (1) ivermectin, (2) doxycycline, and (3) zinc; and, (b) a live, inactivated or attenuated causative agent of the infection, wherein at least one dosage of the anti-viral drug combination is administered 1 or more days before, or on the day of, and/or is administered 1 or more days after, a first dose of the live, inactivated or attenuated causative agent of the infection.

2. The method of claim 1, wherein the doxycycline is dosaged at between about 50 mg to about 2000 mg per dose or per day.

3. The method of claim 1, wherein the zinc comprises or is formulated as: zinc sulphate, zinc acetate, zinc gluconate or zinc picolinate or a zinc salt.

4. The method of claim 1, wherein at least one day before, or on the day of administration of, or at least one day after the first dose of the live, inactivated or attenuated causative agent of the infection is given, the individual in need thereof is administered the anti-viral drug combination.

5. The method of claim 4, wherein the individual in need thereof is administered the anti-viral drug combination on day zero or the day of administration of the live, inactivated or attenuated causative agent of the infection, or day 1, 2, 3, 4, 5, 6, 7, 8, 9, 10, 11, 12, 13 or 14, or one, two, three and/or four weeks after administration of the first dosage of the attenuated and/or the live, inactivated or attenuated causative agent of the infection.

6. The method of claim 1, further comprising administering to a subject or an individual in need thereof:
(a) a booster,
(b) at least one second booster or follow-up administration of: at least one dosage of the live, inactivated or attenuated and causative agent of the infection, is given between about 1 week to one year, or between about two weeks to 9 months, or between about three weeks to 8 months, or between about one month to 7 months, or about 3, 4, 5, or 6 months, after the first administration of the live, inactivated or attenuated causative agent of the infection, or
(c) a third booster, wherein on day zero, or at least one day, or about two days, after, administration of a second or an additional booster dose of the live, inactivated or attenuated causative agent of the infection, is given, and the individual in need thereof is administered an additional dose of the anti-viral drug combination.

7. The method of claim 6, wherein the individual in need thereof is administered an additional dose of the anti-viral drug combination on day 1, 2, 3, 4, 5, 6, 7, 8, 9, 10, 11, 12, 13, or 14 after administration of the second or additional or booster dose of the live, inactivated or attenuated causative agent of the infection.

8. The method of claim 7, wherein the anti-viral drug combination is repeatedly administered if plasma ivermectin is not detectable after a first or subsequent administration for about every 1, 2, 3, 4, 5, 6, 7, 8, 9, 10, 11, 12, 13, or 14 or more days for one or 2, 3, 4, 5, or 6 weeks until plasma ivermectin is detectable.

9. The method of claim 1, wherein the anti-viral drug combination, and/or the live, inactivated or attenuated causative agent of the infection, is administered or formulated:
(a) orally or by inhalation, or is administered by inclusion in a liquid;
(b) as a drink or in drops, wherein optionally the drops comprise nasal drops;
(c) in a mist formulation;
(d) as a tablet, a capsule, a gel, a geltab, a powder, a lozenge, an aerosol, spray, or mist formulation that is inhaled or administered nasally or orally;
(e) by or using a puffer or a nebulizer; or
(f) in a liquid, wherein optionally the liquid is a sterile saline solution which is ingested or gargled by the individual in need thereof.

10. The method of claim 1, wherein the live, inactivated attenuated causative agent of the infection is administered in unit dosages of between about 10 to 50 trillion infectious units or particles, or between about one infectious unit or particle to 10, 20 or 30 billion infection units or particles.

11. The method of claim 1, wherein:
(a) after the first administration of the live, inactivated or attenuated causative agent of the infection, IgM, IgG and/or IgA levels in the individual in need thereof is tested and measured qualitatively and/or quantitatively, and if levels of the measured IgM, IgG and/or IgA are low, a second or additional dosage or administration of the live, inactivated or attenuated causative agent of the infection is given, or
(b) after the first administration of the live, inactivated or attenuated and/or the live, viable or infectious causative agent of the infection levels of the measured IgM, IgG and/or IgA are measured at between about 7 to 21 days, or at 14 and 20 days.

12. The method of claim 1, wherein the individual in need thereof is a human or an animal, or a domestic, farm or zoo animal.

13. The method of claim 1, wherein the
(i) 1R,2S,5S)-N-[(1S)-1-cyano-2-[(3S)-2-oxopyrrolidin-3-yl]ethyl]-3-[(2S)-3,3-dimethyl-2-(2,2,2-trifluoroacetamido)butanoyl]-6,6-dimethyl-3-azabicyclo[3.1.0]hexane-2-carboxamide, or a compound having the following structure and molecular weight:

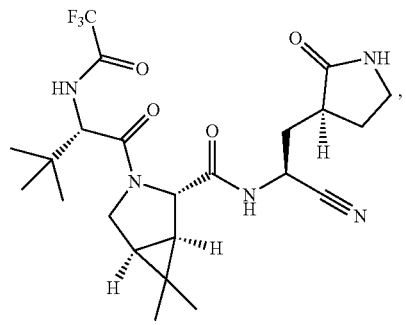

PF-07321332
$C_{23}H_{32}F_3N_5O_4$
FW: 499.527

(ii) ritonavir, and
(iii) a drug combination comprising
(1) ivermectin,
(2) doxycycline, and
(3) zinc,
are formulated together, or separately, or are formulated together or separately in or as a liquid, or are administered as a drink or in drops, or are administered as nasal drops or in a mist, a tablet, a capsule, a gel, a geltab, a powder, a lozenge, an aerosol or spray.

14. The method of claim 1, wherein the anti-viral drug combination is formulated in or as a pharmaceutical dosage form, or is formulated to be administered orally, intramuscularly, subcutaneously, topically, by use of an enema, intravaginally, or intravenously, or is formulated for subcutaneous administration, sublingual administration, inhalation or by aerosol, by inhalation of a liquid, an aerosol, a spray, a mist or a powder, or is formulated in an absorbable patch, an implant, or an enema or a suppository.

15. The method of claim 1, wherein the:
(a) 1R,2S,5S)-N-[(1S)-1-cyano-2-[(3S)-2-oxopyrrolidin-3-yl]ethyl]-3-[(2S)-3,3-dimethyl-2-(2,2,2-trifluoroacetamido)butanoyl]-6,6-dimethyl-3-azabicyclo[3.1.0] hexane-2-carboxamide, or a compound having the following structure and molecular weight:

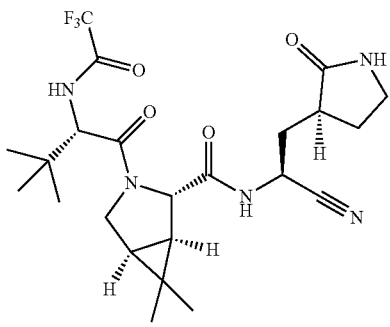

PF-07321332
$C_{23}H_{32}F_3N_5O_4$
FW: 499.527

(b) ritonavir, and
(c) a drug combination comprising
  (1) ivermectin,
  (2) doxycycline, and
  (3) zinc,
  is or are administered:
(a) at a dosage of QD (once a day), bid (twice a day) or tid (three times a day) at a dosage of between about 100 to 600 mg per day or per dosage, or at about 100, 200, 300, 400, 500 or 600 mg per day or per dosage, or
(b) at a dosage of between about 10 mg to 3 gm per dose, or between about 10 mg to 3 gm per day, or 12 mg or 3 mg/kg orally twice daily, or 125 mg orally twice daily or 520 mg/130 mg solution twice per day, or is administered with efavirenz, fosamprenavir, nelfinavir, or nevirapine, or
(c) is dosed either as a single dose or given one, two, three or four times a day, or
(d) at 200 to 800 mg twice daily, or 200, 400, 600 or 800 mg twice daily, or at 200 to 800 mg three times a day, or at 200, 400, 600 or 800 mg three times a day, or is administered at 200 to 800 mg three times a day for between about 2 to 15 days, or for about 2, 3, 4, 5, 6, 7, 8, 9, 10, 11 or 12 days,
(e) for pediatric patients dosage at 16 mg or 4 mg/kg orally twice daily, or
(f) when combined with other drugs a lower dosage, or is administered at 100 or 200 mg three times a day for between about 5 to 15 days, or for about 7, 8, 9, 10, 11 or 12 days.

16. The method of claim 1, wherein the coronavirus infection is or comprises a COVID-19 or a COVID-19 variant infection.

17. The method of claim 1, wherein at least one dosage of the anti-viral drug combination is administered 2, 3, 4, 5, 6, 7, 8, 9, 10, 11, 12, 13 or 14 or more days before, or on the day of, and/or is administered 2, 3, 4, 5, 6, 7, 8, 9, 10, 11, 12, 13 or 14 or more days after, a first dose of the live, inactivated or attenuated causative agent of the infection.

* * * * *